United States Patent
Galvin

(10) Patent No.: US 10,604,544 B2
(45) Date of Patent: Mar. 31, 2020

(54) METHODS FOR PREPARATION OF BILE ACIDS AND DERIVATIVES THEREOF

(71) Applicant: Intercept Pharmaceuticals, Inc., New York, NY (US)

(72) Inventor: Gabriel M Galvin, San Diego, CA (US)

(73) Assignee: INTERCEPT PHARMACEUTICALS, INC., New York, NY (US)

( * ) Notice: Subject to any disclaimer, the term of this patent is extended or adjusted under 35 U.S.C. 154(b) by 0 days.

(21) Appl. No.: 15/750,683

(22) PCT Filed: Aug. 5, 2016

(86) PCT No.: PCT/US2016/045831
§ 371 (c)(1),
(2) Date: Feb. 6, 2018

(87) PCT Pub. No.: WO2017/027396
PCT Pub. Date: Feb. 16, 2017

(65) Prior Publication Data
US 2018/0222937 A1 Aug. 9, 2018

Related U.S. Application Data

(60) Provisional application No. 62/202,300, filed on Aug. 7, 2015.

(51) Int. Cl.
*C07J 9/00* (2006.01)
*C07J 31/00* (2006.01)

(52) U.S. Cl.
CPC ............... *C07J 9/005* (2013.01); *C07J 9/00* (2013.01); *C07J 31/006* (2013.01)

(58) Field of Classification Search
CPC ....................................................... C07J 9/005
See application file for complete search history.

(56) References Cited

U.S. PATENT DOCUMENTS

| 4,212,940 | A | 7/1980 | Weber et al. |
| 4,230,625 | A | 10/1980 | Despreaux et al. |
| 2013/0261317 | A1 | 10/2013 | Moriarty et al. |
| 2014/0094443 | A1 | 4/2014 | Pellicciari et al. |

FOREIGN PATENT DOCUMENTS

| CN | 105348354 A | * | 2/2016 |
| EP | 0 002 535 A2 | | 6/1979 |

OTHER PUBLICATIONS

Afzal M. et al., "Transformation of chenodeoxycholic acid by thermophilic *Geobacillus stearothermophilus*", Biotechnology and Applied Biochemistry, 2011, vol. 58, p. 250-255.

Chen and Penning, "5β-Reduced steroids and human D4-3-ketosteroid 5β-reductase (AKR1D1)", Steroids, 2014, vol. 83, p. 17-26.

Kawamata J. et al., "A G Protein-coupled Receptor Responsive to Bile Acids", The Journal of Biological Chemistry, 2003, vol. 278, p. 9435-9440.

Patani and LaVoie, "Bioisosterism: A Rational Approach in Drug Design", Chem. Rev. 1996, vol. 96, p. 3147-3176.

Pellicciari R. et al. "Nongenomic actions of bile acids. Synthesis and preliminary characterization of 23- and 6,23-alkyl-substituted bile acid derivatives as selective modulators for the G-protein coupled receptor TGR5", Journal of Medicinal Chemistry, 2007, vol. 50, No. 18, 2007, p. 4265-4268.

Stone D. et al. "Hydroxylation of Desoxycorticosterone with *Neurospa crassa*", 1955, JACS, vol. 77, p. 3926-3927.

Zakelj-Marvic and Belic "Hydroxylation of Steroids with 11α-Hydroxylase of *Rhizopus nigricans*", Journal of Steroid Biochemistry, 1987, vol. 28, p. 197-201.

Li, Y et al. "Bile acid receptors in non-alcoholic fatty liver disease", Biochemical Pharmacology, vol. 86, No. 11, 2013, pp. 1517-1524.

Uekawa, T et al. "Short-step Synthesis of Chenodiol from Stigmasterol", Biosci. Biotechnol. Biochem, vol. 68, No. 6, 2004, pp. 1332-1337.

Pellicciari R et al. "6alpha-Ethyl-Chenodeoxycholic Acid (6-ECDCA), a potent and selective FXR agonist endowed with anticholestatic activity", Journal of Medicinal Chemistry, vol. 45, No. 17, 2002, pp. 3569-3572.

Yu, D. et al. "An improved synthesis of 6α-ethylchenodeoxycholic acid (6ECDCA), a potent and selective agonist for the Farnesoid X Receptor (FXR)", Steroids, 2012, vol. 77, p. 1335-1338.

* cited by examiner

*Primary Examiner* — Matthew P Coughlin
(74) *Attorney, Agent, or Firm* — Michelle Iwamoto-Fan; Intercept Pharmaceuticals, Inc.

(57) ABSTRACT

The present application relates to a method of preparing compounds of Formula (A) or a pharmaceutically acceptable salt, solvate, or amino acid conjugate thereof.

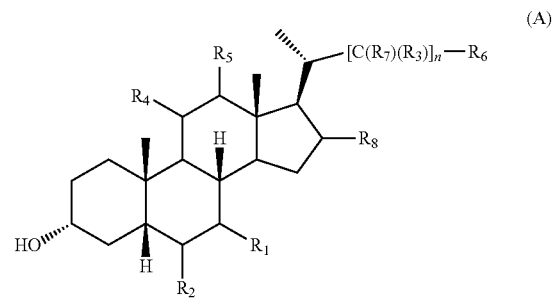

19 Claims, No Drawings

METHODS FOR PREPARATION OF BILE ACIDS AND DERIVATIVES THEREOF

BACKGROUND

Bile acids and bile acid derivatives are useful in the treatment and prevention of diseases. Bile acids have been shown to induce internalization of the TGR5 fusion protein from the cell membrane to the cytoplasm (Kawamata et al., 2003, J. Bio. Chem. 278, 9435). TGR5 is associated with the intracellular accumulation of cAMP and is an attractive target for the treatment of diseases (e.g., obesity, diabetes and metabolic syndrome). Numerous bile acid derivatives are TGR5 agonists, capable of regulating TGR5-mediated diseases and conditions. For example, 23-alkyl-substituted and 6,23-dialkyl-substituted derivatives of chenodeoxycholic acid (CDCA), such as 6α-ethyl-23(S)-methyl-chenodeoxycholic acid, have been reported as potent and selective agonists of TGR5 (Pellicciari, et al., 2007, J. Med. Chem. 50, 4265).

Additionally, a number of bile acid derivatives are Farnesoid X receptor (FXR) agonists, and are able to regulate FXR-mediated diseases and conditions. FXR is a nuclear receptor that functions as a bile acid sensor controlling bile acid homeostasis. FXR is expressed in various organs and shown to be involved in many diseases and conditions, such as liver diseases, lung diseases, renal diseases, intestinal diseases, and heart diseases, and biological processes, including glucose metabolism, insulin metabolism, and lipid metabolism.

Bile acids are often isolated from mammalian organisms that naturally produce them. However, bile acids isolated from such organisms may contain toxins and contaminants. Thus, there are needs for synthetic methods of producing bile acids that do not rely on starting materials of animal origin. The present application addresses these needs.

SUMMARY

The present application relates to a method of preparing a compound of Formula (A):

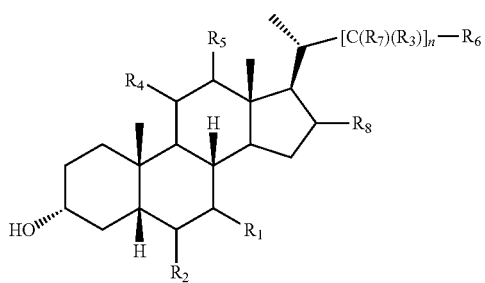

or a pharmaceutically acceptable salt, solvate, or amino acid conjugate thereof, wherein:

$R_1$ is α-OH or an oxo group;
$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;
$R_3$ or $R_7$ are independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;
$R_4$, $R_5$ and $R_8$ are each independently H, α-OH, or β-OH;
$R_6$ is $CO_2H$, $OSO_3H$, $NH_2$, $NHCO_2(CH_2CHCH)phenyl$, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O; and
n is 0, 1, 2 or 3;

comprising the steps of:
(1) converting Compound 1 to Compound 7

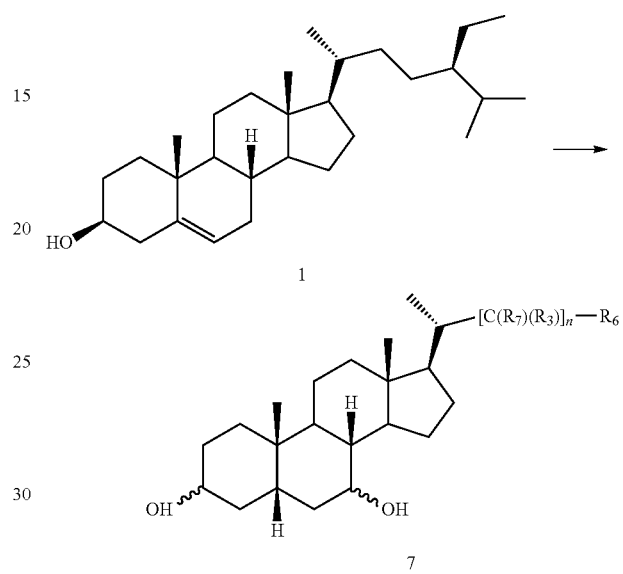

wherein "⁓" indicates that the OH at the C3-position or C7-position is in an α- or β-stereochemistry; and (2) converting Compound 7 to a compound of Formula (A).

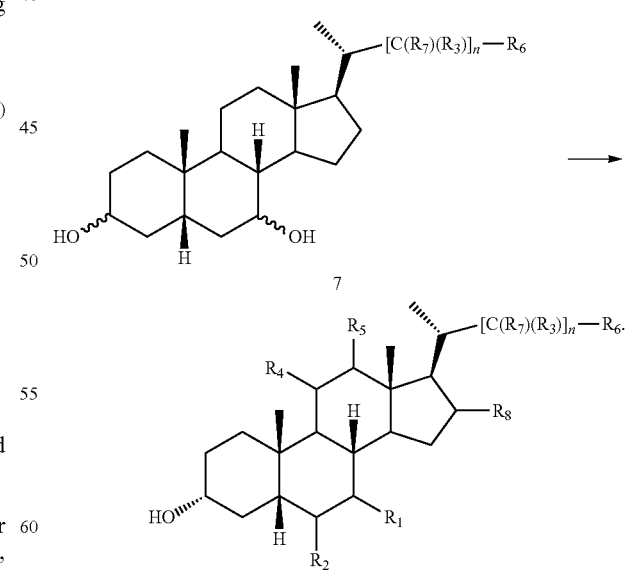

In another aspect of the present invention, a method for preparing a compound of Formula (A) is provided, or a pharmaceutically acceptable salt, solvate, or amino acid conjugate thereof, wherein:

$R_1$ is α-OH or an oxo group;

$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;

$R_3$ or $R_7$ are independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;

$R_4$, $R_5$ and $R_8$ are each independently H, α-OH, or β-OH;

$R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O; and n is 0, 1, 2 or 3;

comprising the steps of:

(1) converting Compound 1 to Compound 2

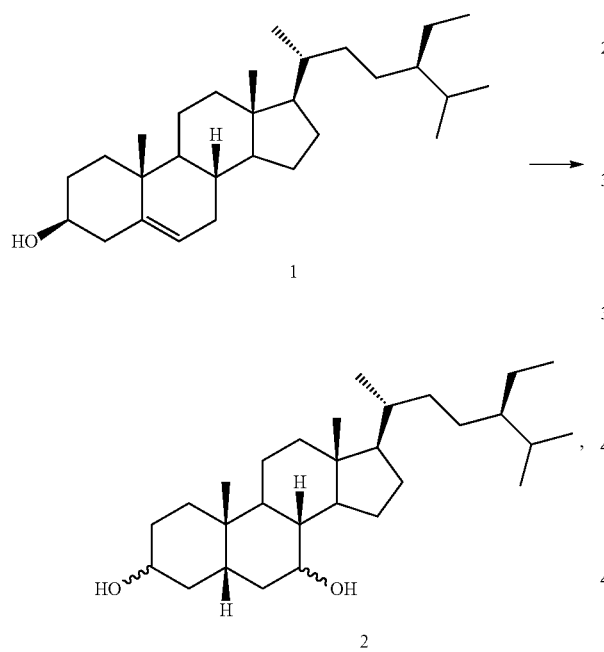

wherein "∿" indicates that the OH at the C3-position or C7-position is in an α- or β-stereochemistry;

(2) converting Compound 2 to Compound 7

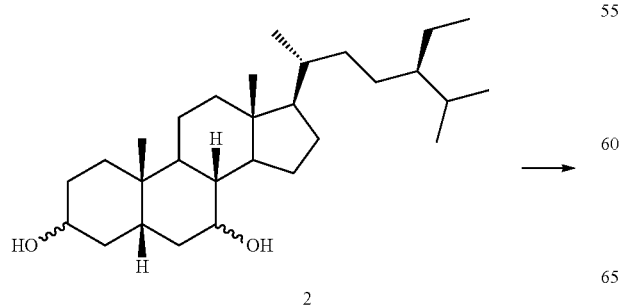

and (3) converting Compound 7 to a compound of Formula (A)

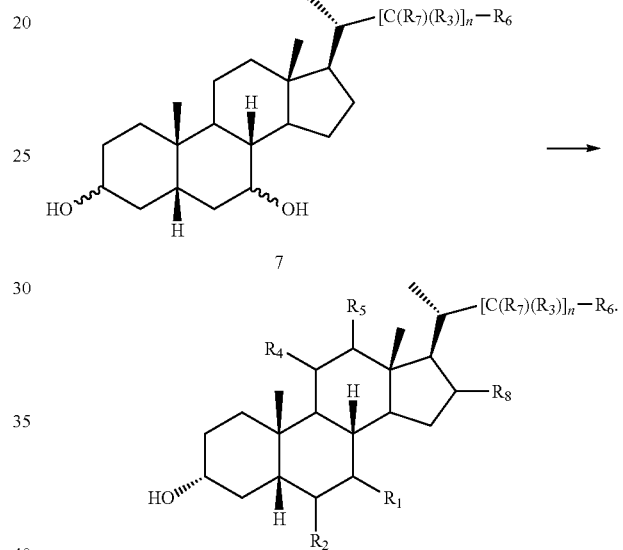

The present application also relates to a method of preparing a compound of Formula (A):

(A)

or a pharmaceutically acceptable salt, solvate, or amino acid conjugate thereof, wherein:

$R_1$ is α-OH or an oxo group;

$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;

$R_3$ and $R_7$ are independently H, F, $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;

$R_4$, $R_5$ and $R_8$ are each independently H, α-OH, or β-OH;

$R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O;

$R_7$ is independently H, F or OH; and n is 0, 1, 2 or 3;

comprising the steps of:

(1) converting Compound 1 to Compound 2

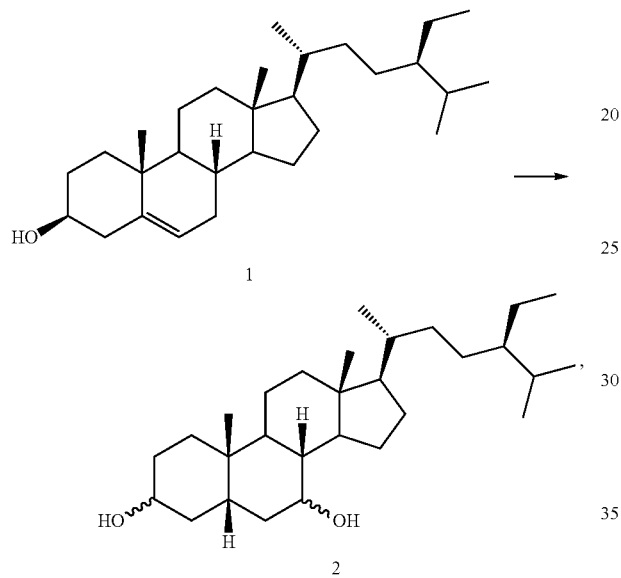

wherein "⁓" indicates that the OH at the C3-position or C7-position is in an α- or β-stereochemistry;

(2) converting Compound 2 to Compound 5

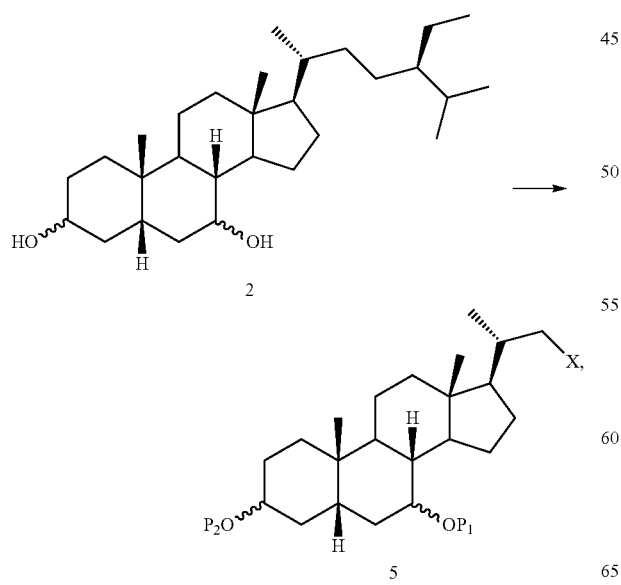

wherein:

X is a leaving group; and $P_1$ and $P_2$ are each independently a protecting group;

(3) converting Compound 5 to Compound 7

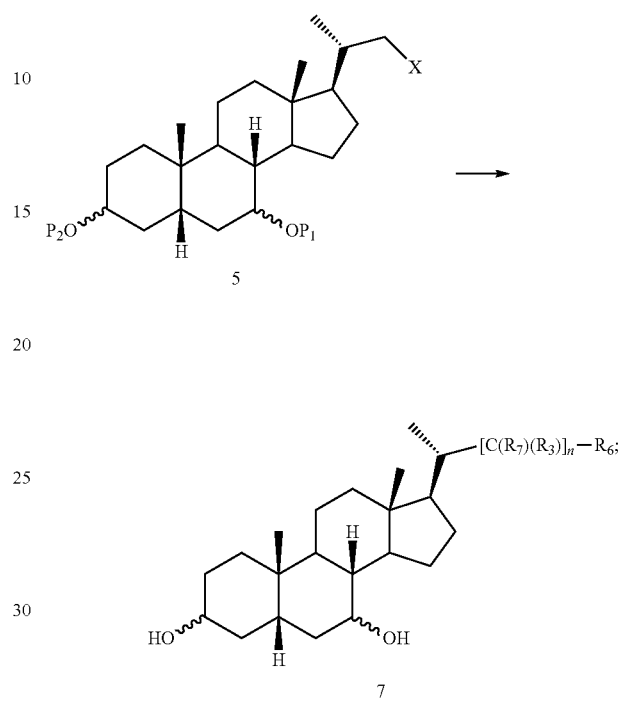

and (4) converting Compound 7 to a compound of Formula (A)

In one embodiment, the compound is Formula (I):

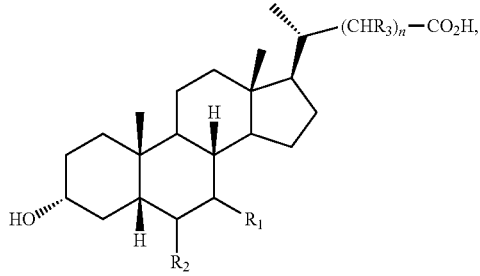

or a pharmaceutically acceptable salt, solvate, or amino acid conjugate thereof, wherein $R_3$ is H or $C_1$-$C_4$ alkyl.

In another embodiment, the compound is Formula (Ia):

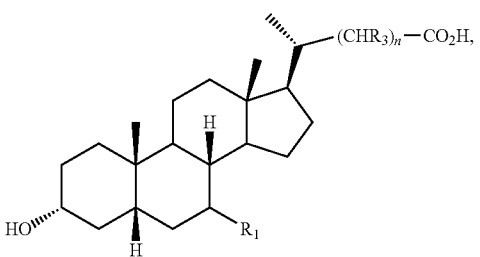

or a pharmaceutically acceptable salt, solvate, or amino acid conjugate thereof, wherein $R_3$ is H or $C_1$-$C_4$ alkyl.

In another embodiment, the compound is Formula (Ib):

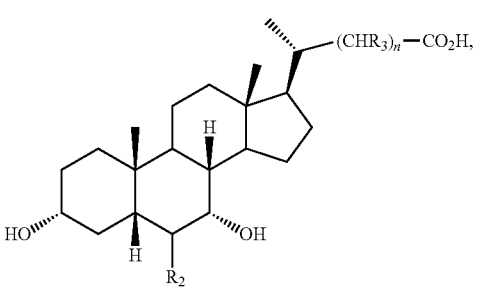

or a pharmaceutically acceptable salt, solvate, or amino acid conjugate thereof, wherein:

$R_2$ is α-$C_1$-$C_3$ alkyl; and $R_3$ is H or $C_1$-$C_4$ alkyl.

In another aspect, the compound is Formula (II):

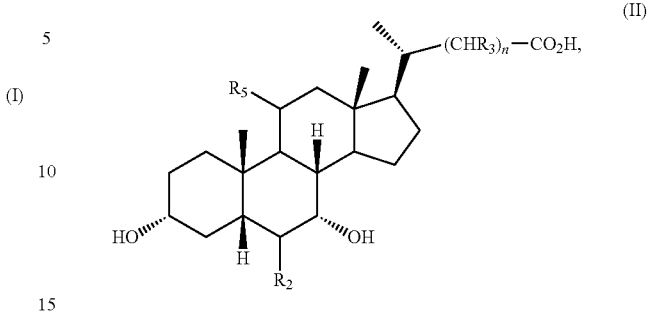

or a pharmaceutically acceptable salt, solvate, or amino acid conjugate thereof, wherein:

$R_2$ is α-$C_1$-$C_3$ alkyl;

$R_3$ is H or $C_1$-$C_4$ alkyl; and $R_5$ is α-OH or β-OH.

In another embodiment, the compound is Formula (III):

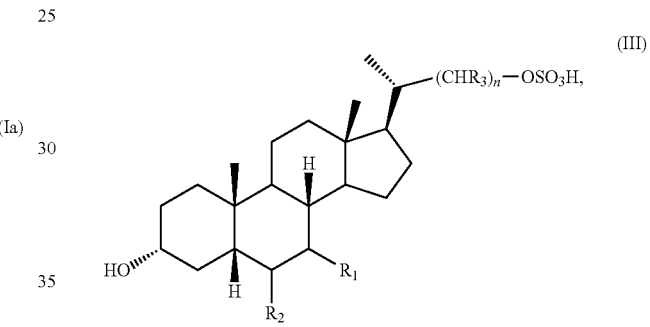

or a pharmaceutically acceptable salt or solvate thereof, wherein:

$R_1$ is α-OH or an oxo group;

$R_2$ is H α-$C_1$-$C_3$ alkyl, cycloalkylmethylene, or cycloalkyl; and $R_3$ is H or $C_1$-$C_4$ alkyl.

In another embodiment, the compound is Formula (IV):

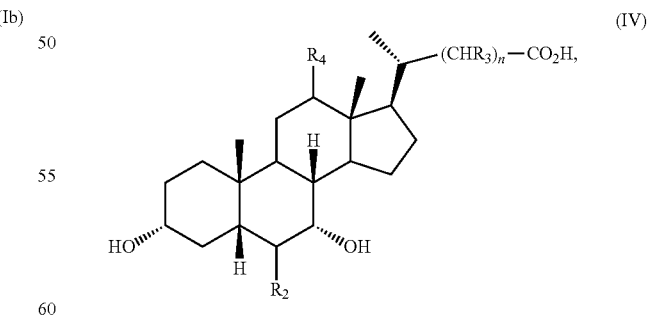

or a pharmaceutically acceptable salt, solvate, or amino acid conjugate thereof, wherein:

$R_2$ is α-$C_1$-$C_3$ alkyl;

$R_3$ is H or $C_1$-$C_4$ alkyl; and $R_4$ is α-OH or β-OH.

In another embodiment, the compound if Formula (V):

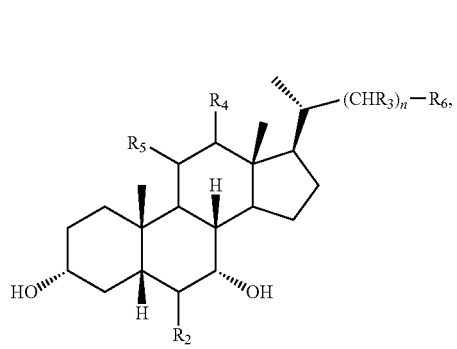

(V)

or a pharmaceutically acceptable salt, solvate, or amino acid conjugate thereof, wherein:
- $R_2$ is H or α-$C_1$-$C_3$ alkyl;
- $R_3$ is H or $C_1$-$C_4$ alkyl;
- $R_4$ and $R_5$ are each independently H, α-OH or β-OH; and
- $R_6$ is an optionally substituted 5-member heterocycle comprising 1-4 heteroatoms selected from N, S and O.

The present application further relates to a compound having the structure:

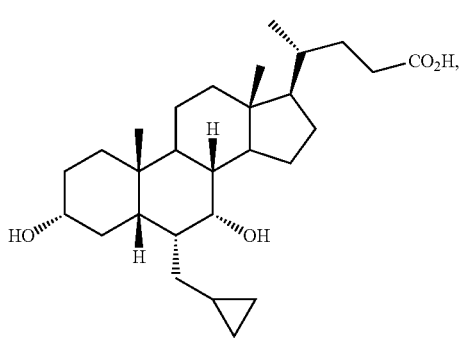

or a pharmaceutically acceptable salt, solvate or amino acid conjugate thereof.

The present application relates to a compound produced by a method of preparing a compound of Formula (A), wherein the compound is

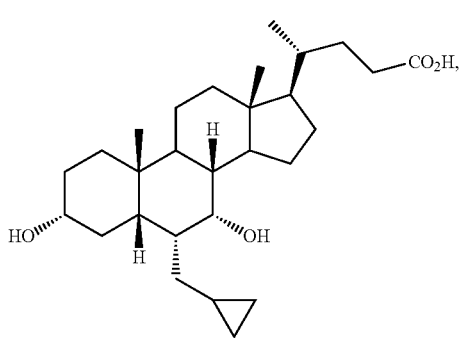

or a pharmaceutically acceptable salt, solvate or amino acid conjugate thereof.

The present application relates to a pharmaceutical composition comprising a compound having the structure:

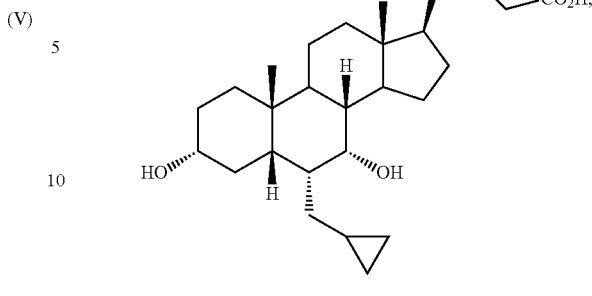

or a pharmaceutically acceptable salt, solvate or amino acid conjugate thereof and at least one pharmaceutically acceptable excipient.

DETAILED DESCRIPTION

The present application is directed to the synthesis of bile acids (BAs) from a plant sterol, such as, but not limited to, β-sitosterol, stigmasterol, brassicasterol or campesterol. More specifically, the present application relates to the synthesis of bile acid derivatives, such as, without limitation, chenodeoxycholic acid (CDCA), ketolithocholic acid (KLCA), 6-$C_1$-$C_3$ alkyl CDCA (e.g., obeticholic acid), and 11-hydroxy obeticholic acid, other useful intermediates thereof and related compositions from the aforementioned plant sterols. The bile acids prepared by the methods of the present application advantageously do not rely on starting materials from mammalian organisms, which may contain toxins and contaminants.

Methods of Synthesis

The present application relates to a method of preparing a compound of Formula (A):

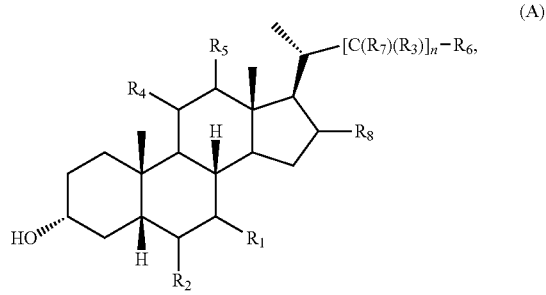

(A)

or a pharmaceutically acceptable salt, solvate, or amino acid conjugate thereof, wherein:
- $R_1$ is α-OH or an oxo group;
- $R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;
- $R_3$ or $R_7$ are independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;
- $R_4$, $R_5$ and $R_8$ are each independently is H, α-OH, or β-OH,
- $R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, CONH(CH$_2$)$_2$OSO$_3$H, or an optionally substituted 5-member heterocycle comprising 1-4 heteroatoms selected from N, S and O; and n is 0, 1, 2 or 3;

comprising the steps of:

(1) converting Compound 1 to Compound 7

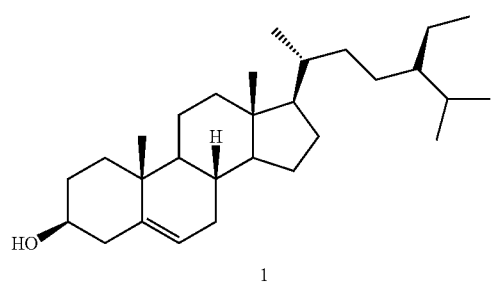

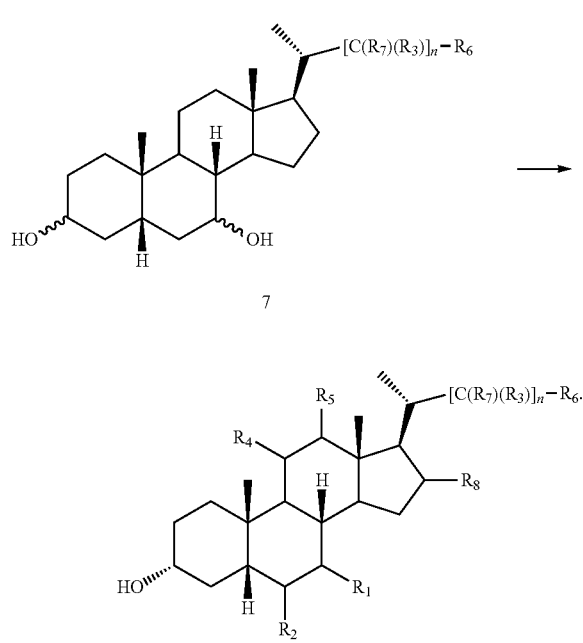

wherein "〜" indicates that the OH at the C3-position or C7-position is in an α- or β-stereochemistry; and (2) converting Compound 7 to a compound of Formula (A).

The present application also relates to a method of preparing a compound of Formula (A):

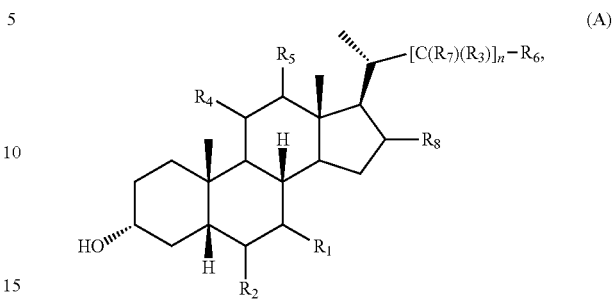

or a pharmaceutically acceptable salt, solvate, or amino acid conjugate thereof, wherein:

$R_1$ is α-OH or an oxo group;

$R_2$ is H, F, α-C$_1$-C$_3$ alkyl optionally substituted with F or OH, α-C$_1$-C$_3$ alkoxy, α-C$_2$-C$_3$ alkenyl or alkynyl, cycloalkylmethylene, or cycloalkyl;

$R_3$ or $R_7$ are independently H, F, or C$_1$-C$_4$ alkyl optionally substituted with F or OH, or $R_3$ or $R_7$ taken together with another $R_3$ or $R_7$ on an adjacent carbon atom forms a substituted or unsubstituted C$_1$-C$_6$ carbocyclic or heterocyclic ring;

$R_4$, $R_5$ and $R_8$ are each independently is H, α-OH, or β-OH, $R_6$ is CO$_2$H, OSO$_3$H, NH$_2$, NHCO$_2$(CH$_2$CHCH)phenyl, NHCO$_2$CH$_2$CH$_3$, C(O)NHOH, C(O)NH(CH$_2$)$_2$OH, CONH(CH$_2$)$_2$OSO$_3$H, or an optionally substituted 5-member heterocycle comprising 1-4 heteroatoms selected from N, S and O; and n is 0, 1, 2 or 3;

comprising the steps of:

(1) converting Compound 1 to Compound 2

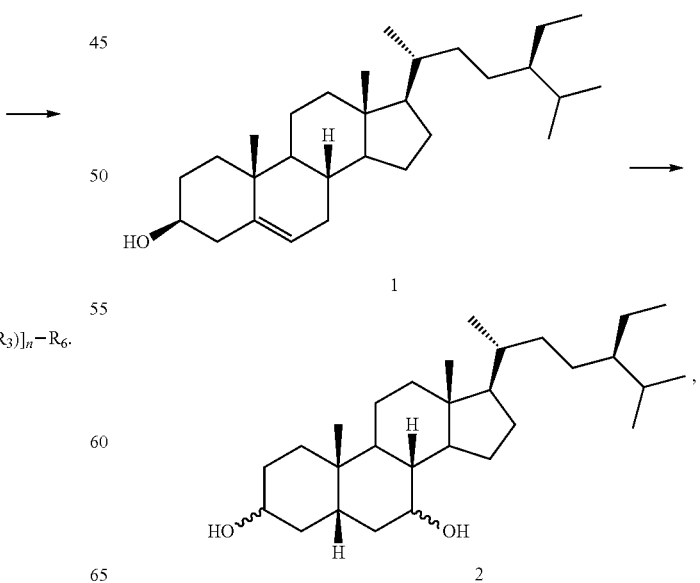

wherein "〰" indicates that the OH at the C3-position or C7-position is in an α- or β-stereochemistry;

(3) converting Compound 2 to Compound 7

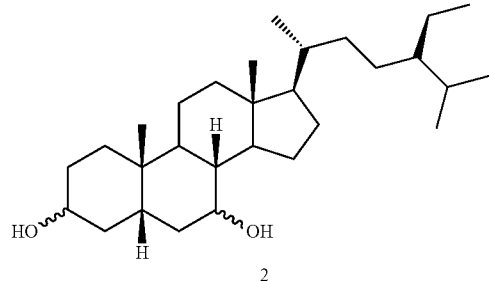

2

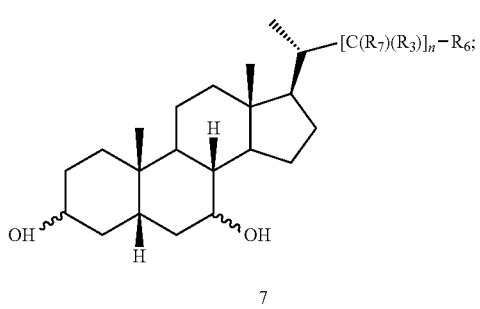

7 and (3) converting Compound 7 to a compound of Formula (A)

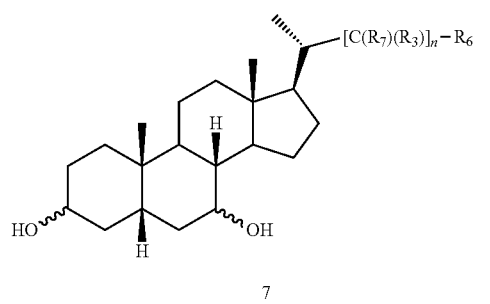

7

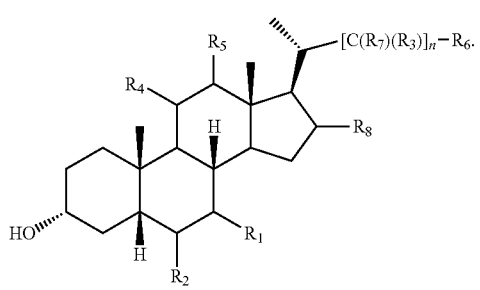

The present application further relates to a method of preparing a compound of Formula (A):

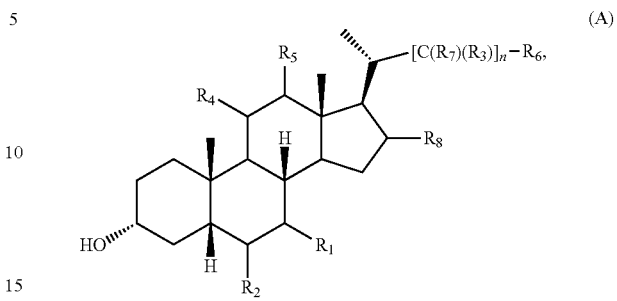

(A)

or a pharmaceutically acceptable salt, solvate, or amino acid conjugate thereof, wherein:

$R_1$ is α-OH or an oxo group;

$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;

$R_3$ or $R_7$ are independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;

$R_4$, $R_5$ and $R_8$ are each independently is H, α-OH, or β-OH, $R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O; and n is 0, 1, 2 or 3;

comprising the steps of:

(1) converting Compound 1 to Compound 2

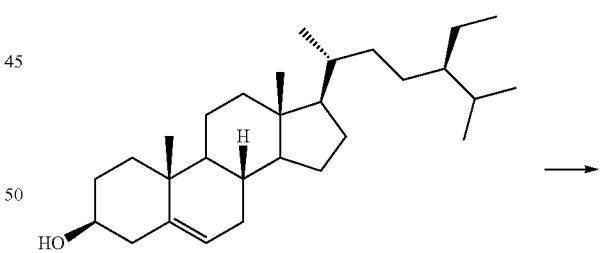

1

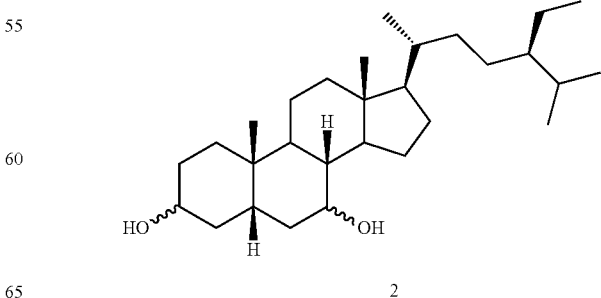

2 wherein " ~~~ " indicates that the OH at the C3-position or C7-position is in an α- or β-stereochemistry;

(2) converting Compound 2 to Compound 5

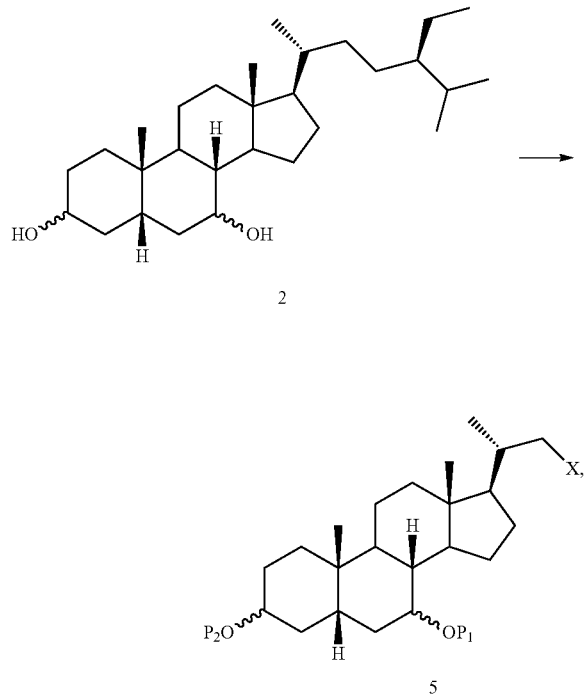

wherein:

X is a leaving group; and $P_1$ and $P_2$ are each independently a protecting group;

(3) converting Compound 5 to Compound 7 and (4) converting Compound 7 to the compound of Formula (A)

In one embodiment, a compound of Formula A is a compound wherein $R_1$ is α-OH. In one embodiment, a compound of Formula A is a compound wherein $R_1$ is an oxo group.

In one embodiment, a compound of Formula A is a compound wherein $R_2$ is H. In one embodiment, a compound of Formula A is a compound wherein $R_2$ is F. In one embodiment, a compound of Formula A is a compound wherein $R_2$ is α-$C_1$-$C_3$ alkyl (e.g., α-methyl, α-ethyl, or α-propyl). In one embodiment, $R_2$ is α-ethyl. In one embodiment, a compound of Formula A is a compound wherein $R_2$ is α-$C_1$-$C_3$ alkyl substituted with F or OH. In one embodiment, a compound of Formula A is a compound wherein $R_2$ is α-$C_1$-$C_3$ alkoxy. In one embodiment, a compound of Formula A is a compound wherein $R_2$ is α-$C_2$-$C_3$ alkenyl or alkynyl. In one embodiment, a compound of Formula A is a compound wherein $R_2$ is cycloalkyl. In one embodiment, a compound of Formula A is a compound wherein $R_2$ is cyclopropyl. In one embodiment, a compound of Formula A is a compound wherein $R_2$ is cyclobutyl. In one embodiment, a compound of Formula A is a compound wherein $R_2$ is cyclopentyl. In one embodiment, a compound of Formula A is a compound wherein $R_2$ is cycloalkylmethylene. In one embodiment, a compound of Formula A is a compound wherein $R_2$ is cyclopropylmethylene. In one embodiment, a compound of Formula A is a compound wherein $R_2$ is cyclobutylmethylene. In one embodiment, a compound of Formula A is a compound wherein $R_2$ is cyclopentylmethylene. In one embodiment, a compound of Formula A is a compound wherein $R_3$ is H. In one embodiment, a compound of Formula A is a compound wherein $R_3$ is F. In one embodiment, a compound of Formula A is a compound wherein $R_3$ is $C_1$-$C_4$ alkyl substituted with F or OH. In one embodiment, a compound of Formula A is a compound wherein $R_3$ taken together with another $R_3$ on an adjacent carbon atom forms a cyclopropyl ring. In one embodiment, a compound of Formula A is a compound wherein $R_3$ is $C_1$-$C_4$ alkyl. In one embodiment, a compound of Formula A is a compound wherein $R_3$ is methyl.

In one embodiment, a compound of Formula A is a compound wherein $R_4$ is H. In one embodiment, a compound of Formula A is a compound wherein $R_4$ is α-OH. In one embodiment, a compound of Formula A is a compound wherein $R_4$ is β-OH.

In one embodiment, a compound of Formula A is a compound wherein $R_5$ is H. In one embodiment, a compound of Formula A is a compound wherein $R_5$ is α-OH. In one embodiment, a compound of Formula A is a compound wherein $R_5$ is β-OH.

In one embodiment, a compound of Formula A is a compound wherein $R_1$ is α-OH, $R_2$ is H, and $R_4$ is H.

In one embodiment, a compound of Formula A is a compound wherein $R_1$ is an oxo group, $R_2$ is H, and $R_4$ is H.

In one embodiment, a compound of Formula A is a compound wherein $R_1$ is α-OH, $R_2$ is α-$C_1$-$C_3$ alkyl (e.g., α-methyl, α-ethyl, or α-propyl), and $R_4$ is H. In one embodiment, $R_1$ is α-OH, $R_2$ is α-ethyl, and $R_4$ is H.

In one embodiment, a compound of Formula A is a compound wherein $R_1$ is α-OH, $R_2$ is α-$C_1$-$C_3$ alkyl (e.g., α-methyl, α-ethyl, or α-propyl), and $R_4$ is α-OH. In one embodiment, $R_1$ is α-OH, $R_2$ is α-ethyl, and $R_4$ is α-OH.

In one embodiment, a compound of Formula A is a compound wherein $R_2$ is α-$C_1$-$C_3$ alkyl (e.g., α-methyl, α-ethyl, or α-propyl), and $R_4$ is β-OH. In one embodiment, $R_1$ is α-OH, $R_2$ is α-ethyl, and $R_4$ is β-OH.

In one embodiment, a compound of Formula A is a compound wherein $R_6$ is $CO_2H$. In one embodiment, a compound of Formula A is a compound wherein $R_6$ is $OSO_3H$. In one embodiment, a compound of Formula A is a compound wherein $R_6$ is $NH_2$. In one embodiment, a compound of Formula A is a compound wherein $R_6$ is $NHCO_2(CH_2CHCH)phenyl$. In one embodiment, a compound of Formula A is a compound wherein $R_6$ is $NHCO_2CH_2CH_3$. In one embodiment, a compound of Formula A is a compound wherein $R_6$ is $C(O)NHOH$. In one embodiment, a compound of Formula A is a compound wherein $R_6$ is $C(O)NH(CH_2)_2OH$. In one embodiment, a compound of Formula A is a compound wherein $R_6$ is $CONH(CH_2)_2OSO_3H$. In one embodiment, a compound of Formula A is a compound wherein $R_6$ is an optionally substituted 5-member heterocycle comprising 1-4 heteroatoms selected from N, S and O. In one embodiment, a compound of Formula A is a compound wherein $R_6$ is an optionally substituted 5-member heterocycle comprising 1-2 heteroatoms selected from N and O. In one embodiment, a compound of Formula A is a compound wherein $R_6$ is an optionally substituted 5-member heterocycle comprising 1-2 heteroatoms selected from N and S. In one embodiment, a compound of Formula A is a compound wherein $R_6$ is an optionally substituted 5-member heterocycle comprising 1-2 heteroatoms selected from O and S. In one embodiment, a compound of Formula A is a compound wherein $R_6$ is an optionally substituted 5-member heterocycle comprising 1-3 N atoms. In one embodiment, a compound of Formula A is a compound wherein $R_6$ is an 5-member heterocycle comprising 1-4 heteroatoms selected from N, S and O substituted with $NHS(O)_2CH_3$. In one embodiment, the 5-member heterocycle is 1,2,4-oxadiazolidine. In one embodiment, the 5-member heterocycle is [1,2,4]-oxadiazole-3-one-5yl. In one embodiment, the 5-member heterocycle is tetrazol-5-yl. In one embodiment, the 5-member heterocycle is 1,3,4-oxadiazolyl. In one embodiment, the 5-member heterocycle is thiazolidine-2,4-dionyl. In one embodiment, the 5-member heterocycle is thiazolidine-dionyl.

In one embodiment, a compound of Formula A is a compound wherein $R_7$ is H. In one embodiment, a compound of Formula A is a compound wherein $R_7$ is F. In one embodiment, a compound of Formula A is a compound wherein $R_7$ is OH.

In one embodiment, a compound of Formula A is a compound wherein $R_8$ is H. In one embodiment, a compound of Formula A is a compound wherein $R_8$ is α-OH. In one embodiment, a compound of Formula A is a compound wherein $R_8$ is β-OH.

In one embodiment, a compound of Formula A is a compound wherein n is 0. In one embodiment, a compound of Formula A is a compound wherein n is 1. In another embodiment, a compound of Formula B is a compound wherein n is 2. In one embodiment, a compound of Formula A is a compound wherein n is 3.

In one embodiment, a compound of Formula A is CDCA:

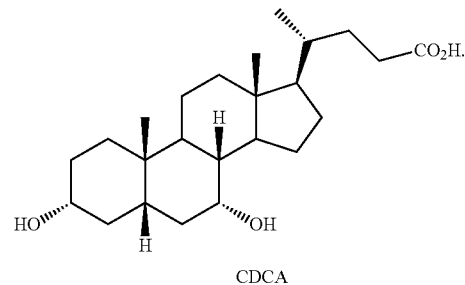

CDCA

In one embodiment, a compound of Formula A is KLCA:

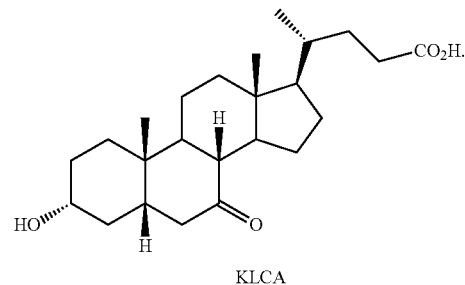

KLCA

In one embodiment, a compound of Formula A is obeticholic acid, or INT-747:

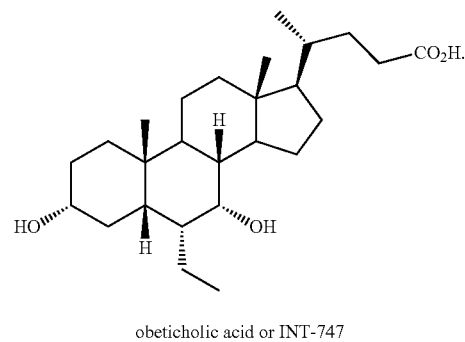

obeticholic acid or INT-747

In one embodiment, a compound of Formula A is 11-β-hydroxy obeticholic acid:

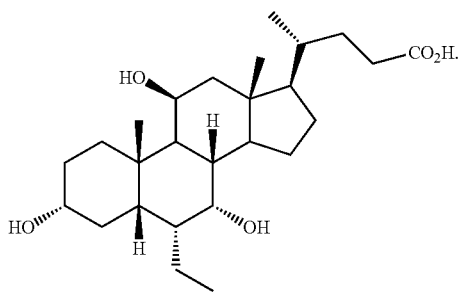

In one embodiment, a compound of Formula A is 3-deoxy 11-β-hydroxy obeticholic acid:

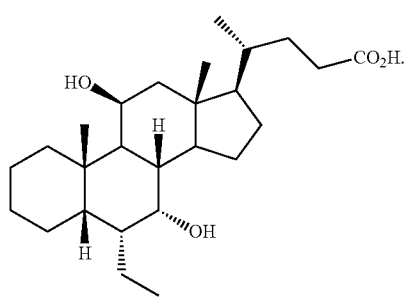

In one embodiment, a compound of Formula A is 6α-ethyl-3α, 7α-23-trihydroxy-24-nor-5β-cholan-23-sulfate:

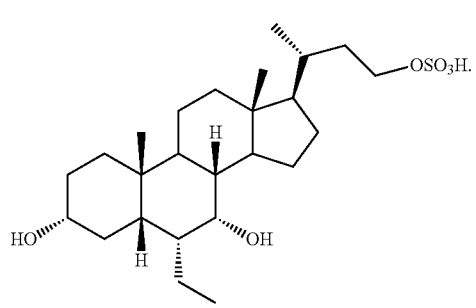

In one embodiment, a compound of Formula A is 6α-ethyl-23(S)-methyl-3α, 7α, 12α-trihydroxy-5β-cholan-24-oic acid:

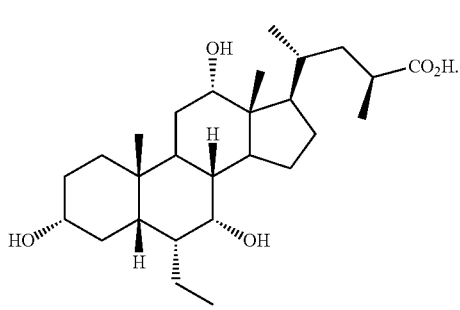

In one embodiment, a compound of Formula A is 6α-CP-MCDCA:

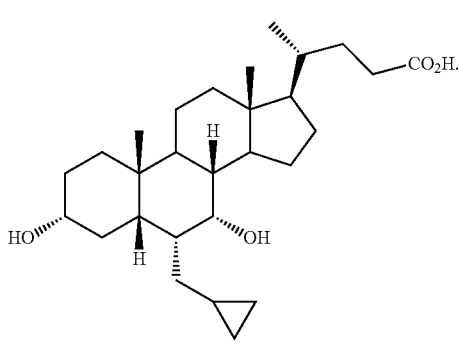

The present application further relates to a compound having the structure:

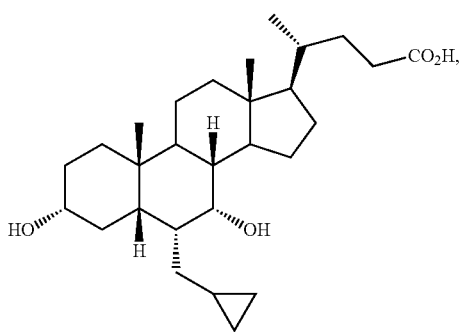

or a pharmaceutically acceptable salt, solvate or amino acid conjugate thereof.

The present application relates to a compound produced by a method of preparing the compound of Formula (A), wherein the compound is

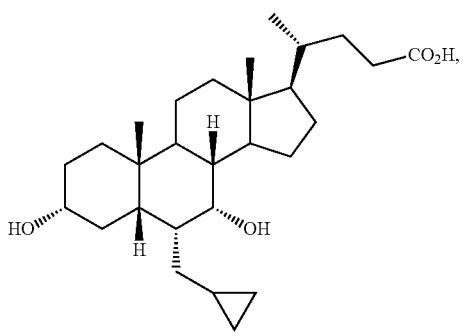

or a pharmaceutically acceptable salt, solvate or amino acid conjugate thereof.

The present application further relates to a pharmaceutical composition comprising a compound having the structure:

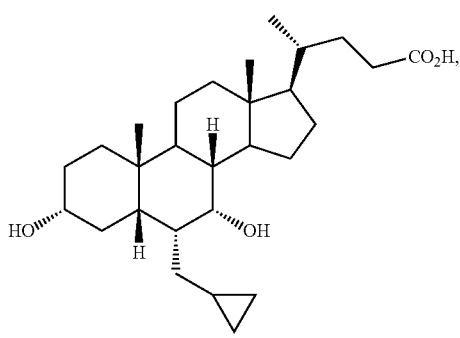

or a pharmaceutically acceptable salt, solvate or amino acid conjugate thereof and at least one pharmaceutically acceptable excipient.

The present application relates to a method of preparing a compound of Formula (I):

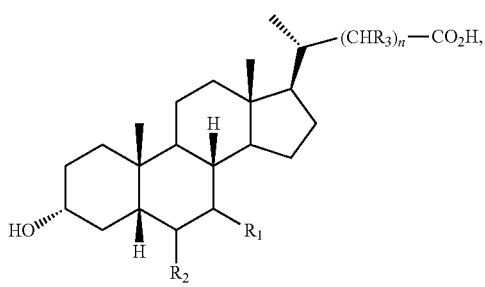

or a pharmaceutically acceptable salt, solvate, or amino acid conjugate thereof, wherein:
$R_1$ is α-OH or an oxo group; and
$R_2$ is H or α-$C_1$-$C_3$ alkyl,
$R_3$ is H or $C_1$-$C_4$ alkyl; and
n is 0, 1, 2 or 3,
comprising the steps described herein, where in one embodiment, a compound of Formula I is a compound wherein $R_1$ is α-OH. In one embodiment, a compound of Formula I is a compound wherein $R_1$ is an oxo group.

In one embodiment, a compound of Formula I is a compound wherein $R_2$ is H. In one embodiment, a compound of Formula I is a compound wherein $R_2$ is α-$C_1$-$C_3$ alkyl (e.g., α-methyl, α-ethyl, or α-propyl). In one embodiment, $R_2$ is α-ethyl.

In one embodiment, a compound of Formula I is a compound wherein $R_1$ is α-OH and $R_2$ is H.

In one embodiment, a compound of Formula I is a compound wherein $R_1$ is an oxo group and $R_2$ is H.

In one embodiment, a compound of Formula I is a compound wherein $R_1$ is α-OH and $R_2$ is α-$C_1$-$C_3$ alkyl (e.g., α-methyl, α-ethyl, or α-propyl). In one embodiment, $R_1$ is α-OH and $R_2$ is α-ethyl.

In one embodiment, a compound of Formula I is a compound wherein $R_3$ is H. In one embodiment, a compound of Formula I is a compound wherein $R_3$ is $C_1$-$C_4$ alkyl. In one embodiment, a compound of Formula I is a compound wherein $R_3$ is methyl.

In one embodiment, a compound of Formula I is a compound wherein n is 1. In one embodiment, a compound of Formula I is a compound wherein n is 2. In one embodiment, a compound of Formula I is a compound wherein n is 3. In one embodiment, a compound of Formula I is CDCA:

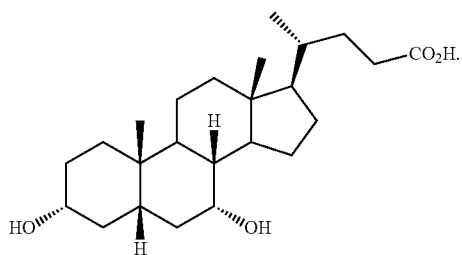

CDCA

In one embodiment, a compound of Formula I is KLCA:

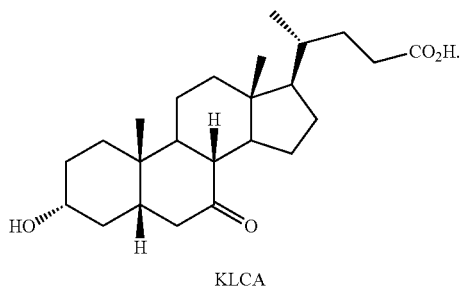

KLCA

In one embodiment, a compound of Formula I is obeticholic acid, or INT-747:

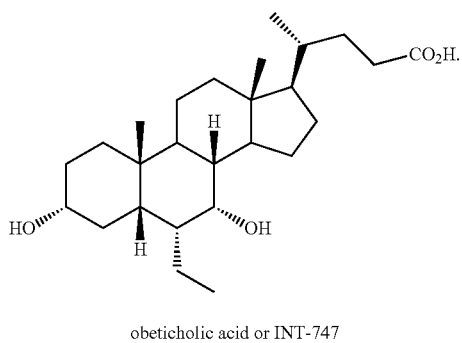

obeticholic acid or INT-747

The present application relates to a method of preparing a compound of Formula (Ia):

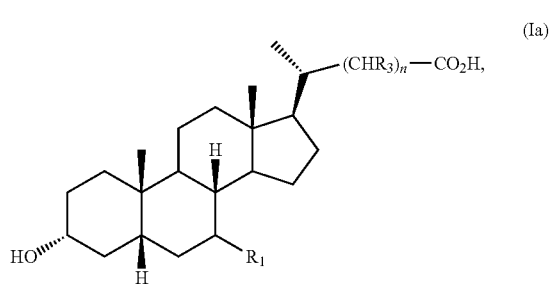

or a pharmaceutically acceptable salt, solvate, or amino acid conjugate thereof, wherein $R_1$ is α-OH or an oxo group;

$R_3$ is H or $C_1$-$C_4$ alkyl; and n is 0, 1, 2 or 3;

comprising the steps defined herein, wherein, in one embodiment, a compound of Formula Ia is a compound wherein $R_1$ is α-OH. In one embodiment, a compound of Formula Ia is a compound wherein $R_1$ is an oxo group. In one embodiment, a compound of Formula I is a compound wherein $R_3$ is H. In one embodiment, a compound of Formula Ia is a compound wherein $R_3$ is $C_1$-$C_4$ alkyl. In one embodiment, a compound of Formula Ia is a compound wherein $R_3$ is methyl.

In one embodiment, a compound of Formula Ia is a compound wherein n is 1. In one embodiment, a compound of Formula Ia is a compound wherein n is 2. In one embodiment, a compound of Formula Ia is a compound wherein n is 3.

In one embodiment, a compound of Formula Ia is CDCA:

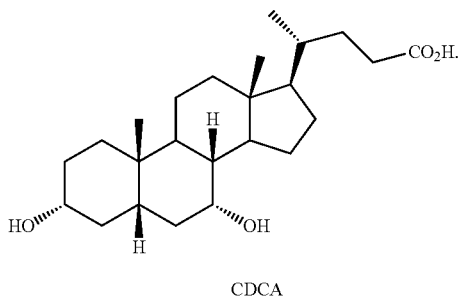

CDCA

In one embodiment, a compound of Formula Ia is KLCA:

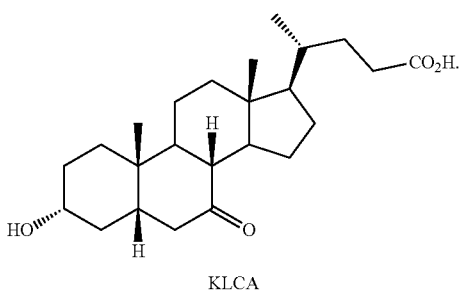

KLCA

The present application relates to a method of preparing a compound of Formula (Ib):

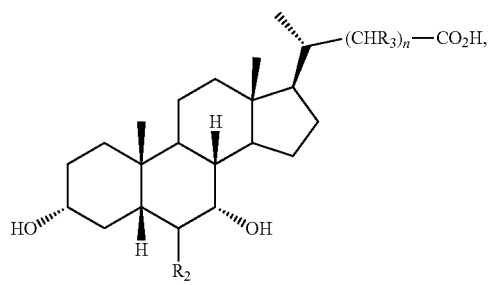

or a pharmaceutically acceptable salt, solvate, or amino acid conjugate thereof, wherein $R_2$ is α-$C_1$-$C_3$ alkyl;

$R_3$ is H or $C_1$-$C_4$ alkyl; and n is 0, 1, 2 or 3;

comprising the steps as defined herein, wherein:

in one embodiment, a compound of Formula Ib is a compound wherein $R_2$ is α-methyl, α-ethyl, or α-propyl. In one embodiment, $R_2$ is α-ethyl.

In one embodiment, a compound of Formula Ib is a compound wherein $R_3$ is H. In one embodiment, a compound of Formula Ib is a compound wherein $R_3$ is $C_1$-$C_4$ alkyl. In one embodiment, a compound of Formula Ib is a compound wherein $R_3$ is methyl.

In one embodiment, a compound of Formula Ib is a compound wherein n is 1. In one embodiment, a compound of Formula Ib is a compound wherein n is 2. In one embodiment, a compound of Formula Ib is a compound wherein n is 3.

In one embodiment, a compound of Formula Ib is obeticholic acid, or INT-747:

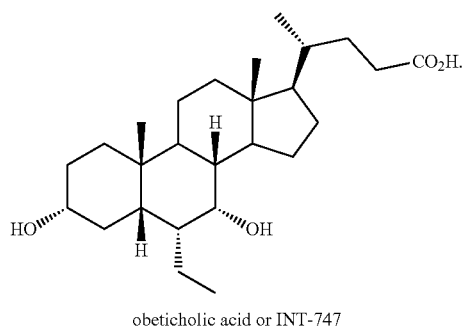

obeticholic acid or INT-747

The present application relates to a method of preparing a compound of Formula (II):

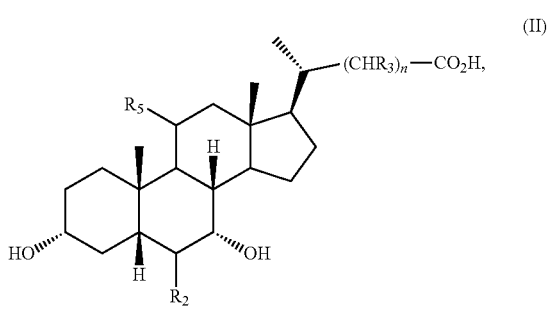

or a pharmaceutically acceptable salt, solvate, or amino acid conjugate thereof, wherein:

$R_2$ is α-$C_1$-$C_3$ alkyl;

$R_3$ is H or $C_1$-$C_4$ alkyl;

$R_5$ is α-OH or β-OH; and n is 0, 1, 2 or 3;

comprising the steps as defined herein, wherein, in one embodiment, a compound of Formula II is a compound wherein $R_2$ is α-$C_1$-$C_3$ alkyl (e.g., α-methyl, α-ethyl, or α-propyl). In one embodiment, $R_2$ is α-ethyl.

In one embodiment, a compound of Formula II is a compound wherein $R_3$ is H. In one embodiment, a compound of Formula II is a compound wherein $R_3$ is $C_1$-$C_4$ alkyl. In one embodiment, a compound of Formula II is a compound wherein $R_3$ is methyl. In one embodiment, a compound of Formula II is a compound wherein $R_5$ is α-OH. In one embodiment, a compound of Formula II is a compound wherein $R_5$ is β-OH.

In one embodiment, a compound of Formula II is a compound wherein n is 1. In one embodiment, a compound of Formula II is a compound wherein n is 2. In one embodiment, a compound of Formula II is a compound wherein n is 3.

In one embodiment, a compound of Formula II is 11-β-hydroxyl obeticholic acid:

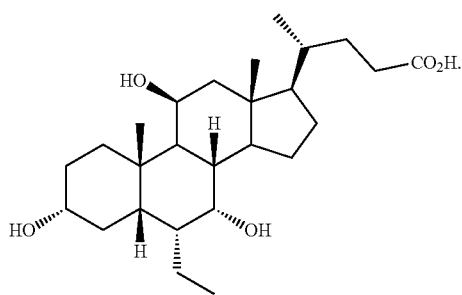

In another embodiment, a compound of Formula II is 3-deoxy 11-β-hydroxy obeticholic acid:

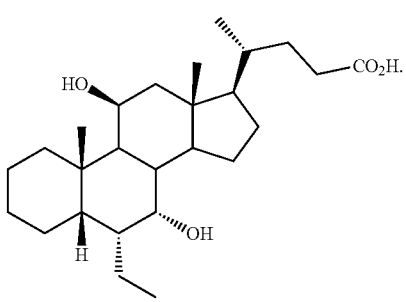 [SMILES: CC[C@H]1[C@@H](O)C2C3CC[C@H]([C@H](C)CCC(=O)O)[C@@]3(C)C[C@H](O)C2[C@@]2(C)CCCC[C@@H]12]

The present application relates to a method of preparing a compound of Formula (III):

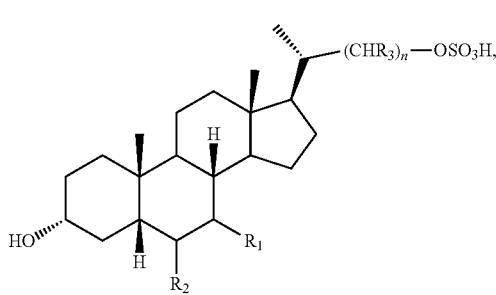

(III)

or a pharmaceutically acceptable salt or solvate thereof, wherein:
$R_1$ is α-OH or an oxo group;
$R_2$ is H, α-$C_1$-$C_3$ alkyl, cycloalkylmethylene, or cycloalkyl;
$R_3$ is H or $C_1$-$C_4$ alkyl; and
n is 0, 1, 2 or 3;

comprising the steps as defined herein, wherein, in one embodiment, a compound of Formula III is a compound wherein $R_1$ is α-OH. In one embodiment, a compound of Formula III is a compound wherein $R_2$ is α-$C_1$-$C_3$ alkyl (e.g., α-methyl, α-ethyl, or α-propyl). In one embodiment, $R_2$ is α-ethyl.

In one embodiment, a compound of Formula III is a compound wherein $R_3$ is H. In one embodiment, a compound of Formula III is a compound wherein $R_3$ is $C_1$-$C_4$ alkyl. In one embodiment, a compound of Formula III is a compound wherein $R_3$ is methyl.

In one embodiment, a compound of Formula III is a compound wherein n is 1. In one embodiment, a compound of Formula III is a compound wherein n is 2. In one embodiment, a compound of Formula III is a compound wherein n is 3.

In one embodiment, a compound of Formula III is 6α-ethyl-3α, 7α-23-trihydroxy-24-nor-5β-cholan-23-sulfate:

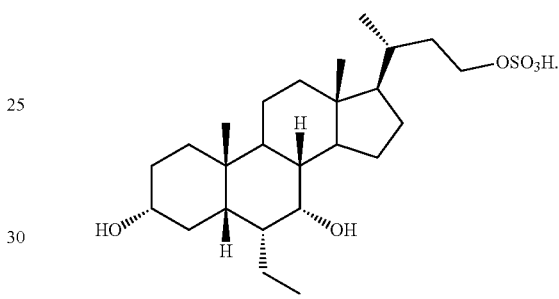

In another embodiment, a compound of Formula III can be prepared via intermediate 5a or 5b. For example, 5a may be alkylated with a cyanide source, followed by hydrolysis of the nitrile to the carboxylic acid. The carboxylic acid and be reduced to the alcohol which can be converted to compounds of Formula III.

The present application relates to a method of preparing a compound of Formula (IV):

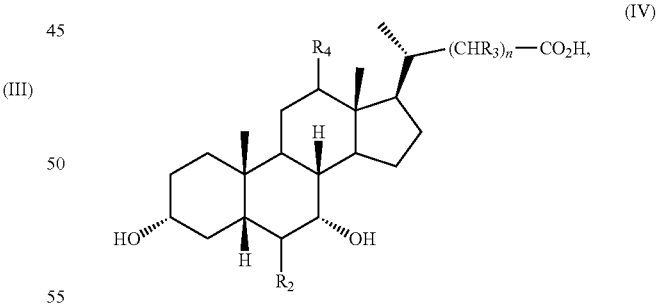

(IV)

or a pharmaceutically acceptable salt, solvate, or amino acid conjugate thereof, wherein:
$R_2$ is α-$C_1$-$C_3$ alkyl;
$R_3$ is H or $C_1$-$C_4$ alkyl;
$R_4$ is α-OH or β-OH; and
n is 0, 1, 2 or 3;

comprising the steps as defined herein, wherein, in one embodiment, a compound of Formula IV is a compound wherein $R_2$ is α-ethyl. In one embodiment, a compound of Formula IV is a compound wherein $R_3$ is H. In one embodiment, a compound of Formula IV is a compound wherein $R_3$ is $C_1$-$C_4$ alkyl. In one embodiment, a compound of Formula IV is a compound wherein $R_3$ is methyl.

In one embodiment, a compound of Formula IV is a compound wherein n is 1. In one embodiment, a compound of Formula IV is a compound wherein n is 2. In one embodiment, a compound of Formula IV is a compound wherein n is 3.

In one embodiment, a compound of Formula IV is 6α-ethyl-23(S)-methyl-3a, 7α, 12α-trihydroxy-5β-cholan-24-oic acid:

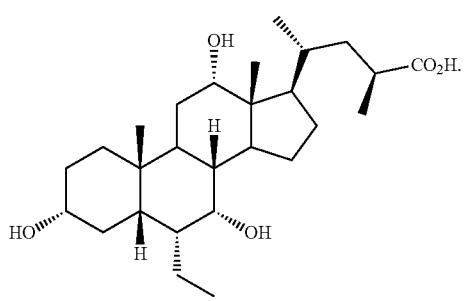

The present application relates to a method of preparing a compound of Formula (V):

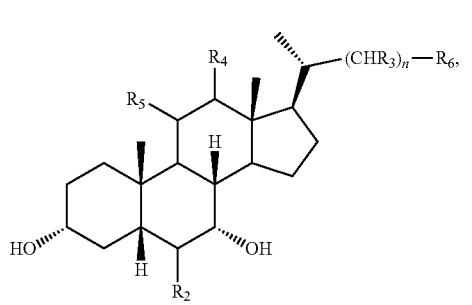

or a pharmaceutically acceptable salt, solvate, or amino acid conjugate thereof, wherein:
$R_2$ is H or α-$C_1$-$C_3$ alkyl;
$R_3$ is H or $C_1$-$C_4$ alkyl;
$R_4$ and $R_5$ are each independently H, α-OH or β-OH; and
$R_6$ is an optionally substituted 5-member heterocycle comprising 1-4 heteroatoms selected from N, S and O; and
n is 0, 1, 2 or 3;
comprising the steps as defined herein, wherein, in one embodiment, a compound of Formula V is a compound wherein $R_3$ is H. In one embodiment, a compound of Formula V is a compound wherein $R_3$ is $C_1$-$C_4$ alkyl. In one embodiment, a compound of Formula V is a compound wherein $R_3$ is methyl.

In one embodiment, a compound of Formula V is a compound wherein $R_4$ or $R_5$ is α-OH. In one embodiment, a compound of Formula V is a compound wherein $R_4$ or $R_5$ is β-OH.

In one embodiment, a compound of Formula V is a compound wherein $R_6$ is an optionally substituted 5-member heterocycle comprising 1-2 heteroatoms selected from N and O. In one embodiment, a compound of Formula V is a compound wherein $R_6$ is an optionally substituted 5-member heterocycle comprising 1-2 heteroatoms selected from N and S. In one embodiment, a compound of Formula V is a compound wherein $R_6$ is an optionally substituted 5-member heterocycle comprising 1-2 heteroatoms selected from O and S. In one embodiment, a compound of Formula V is a compound wherein $R_6$ is an optionally substituted 5-member heterocycle comprising 1-3 N atoms. In one embodiment, a compound of Formula A is a compound wherein $R_6$ is an 5-member heterocycle comprising 1-4 heteroatoms selected from N, S and O substituted with $NHS(O)_2CH_3$. In one embodiment, the 5-member heterocycle is 1,2,4-oxadiazolidine. In one embodiment, the 5-member heterocycle is [1,2,4]-oxadiazole-3-one-5yl. In one embodiment, the 5-member heterocycle is tetrazol-5-yl. In one embodiment, the 5-member heterocycle is 1,3,4-oxadiazolyl. In one embodiment, the 5-member heterocycle is thiazolidine-2,4-dionyl. In one embodiment, the 5-member heterocycle is thiazolidine-dionyl.

In one embodiment, a compound of Formula V is a compound wherein n is 1. In one embodiment, a compound of Formula V is a compound wherein n is 2. In one embodiment, a compound of Formula V is a compound wherein n is 3.

In one embodiment, the conversion of Compound 1 to Compound 7 in the methods described herein (e.g., the methods of preparing a compound of Formula (A), (I), (Ia), (Ib), (II), (III), (IV), or (V)) comprises the steps of:

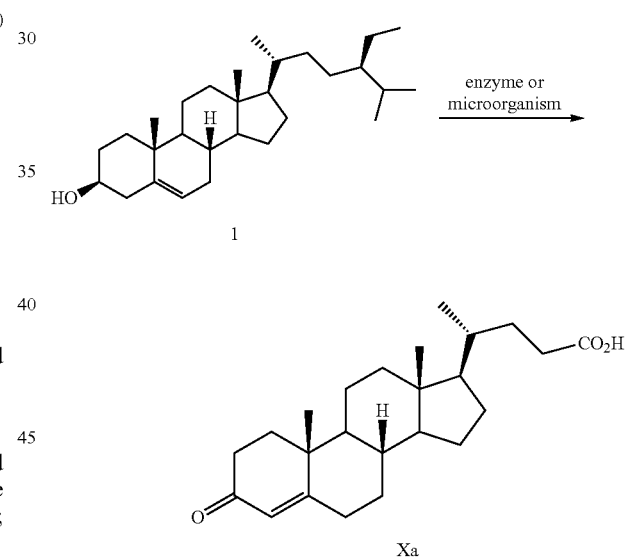

Compound 1 is subjected to enzymatic or microbial oxidation conditions to provide C24 acid with concomitant oxidation at C3 and migration of the C5-C6 olefin to generate Compound Xa.

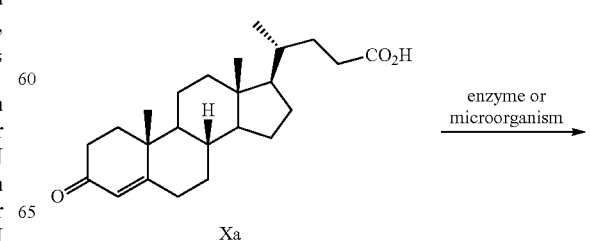

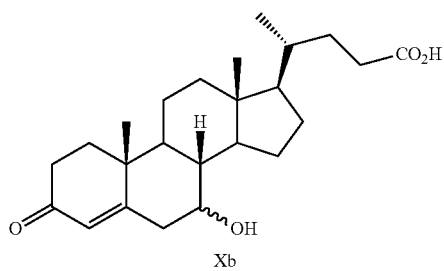

Xb

Compound Xa is further subjected to enzymatic or microbial oxidation conditions to affect hydroxylation at C7 to generate Compound Xb.

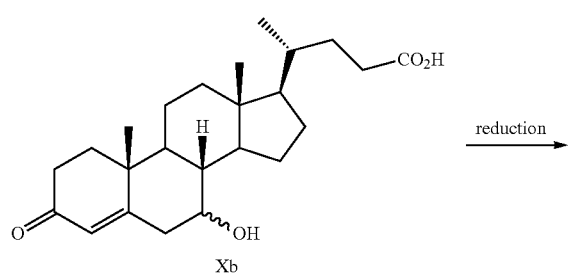

Xb

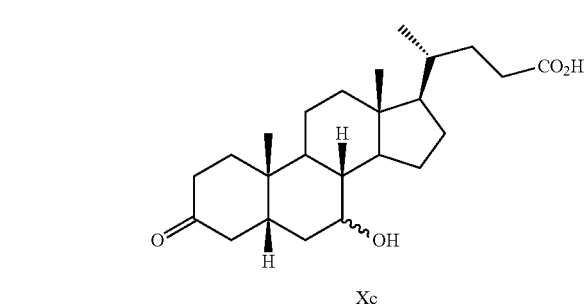

Xc

Compound Xb is subjected to olefin reduction conditions. Compound Xb is hydrogenated in the presence of a palladium catalyst (e.g., Pd/C), platinum catalyst (e.g., PtO$_2$), nickel catalyst (e.g., Raney nickel and Urushibara nickel), or copper catalyst (e.g., Cu/Al$_2$O$_3$) to generate Compound Xc.

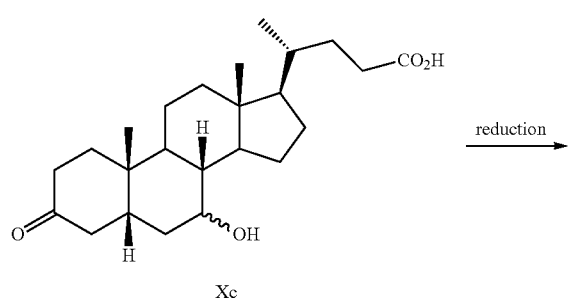

Xc

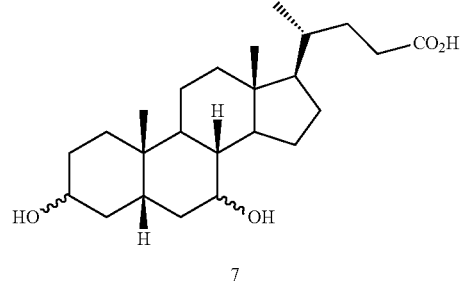

7

Compound Xc is subjected to ketone reduction conditions, thus Compound Xc is contacted with a reducing agent (e.g., NaBH$_4$) to generate Compound 7.

In one embodiment, the conversion of Compound 1 to Compound 2 in the methods described herein (e.g., the methods of preparing a compound of Formula (A), (I), (Ia), (Ib), (II), (III), (IV), or (V)) comprises the steps of:

oxidizing Compound 1a to Compound Ia:

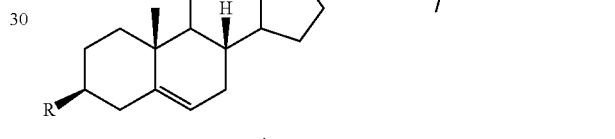

1a

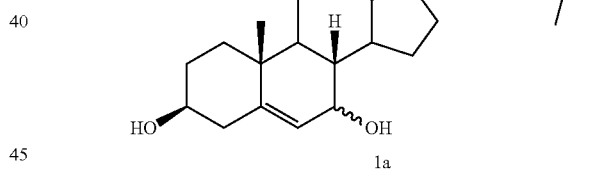

1a wherein:

R is OH or OP$_2$;

P$_2$ is a protecting group; and

"⁓" indicates that the OH at the C7-position is in an α- or β-stereochemistry; reducing Compound Ia to Compound 2b:

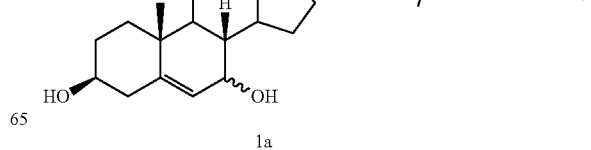

1a

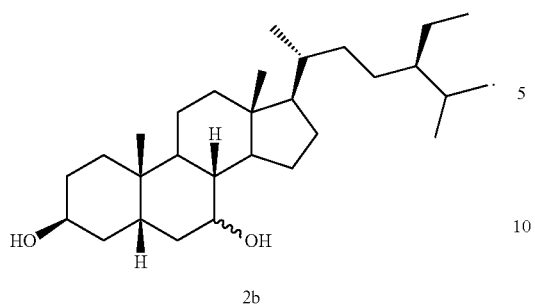

2b

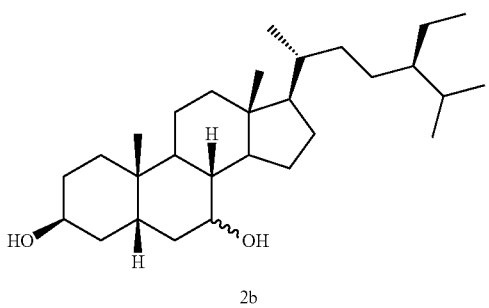

2b wherein "⁓" indicates that the OH at the C7-position is in an α- or β-stereochemistry.

In one embodiment, the conversion of Compound 1 to Compound 2 in the methods described herein (e.g., the methods of preparing a compound of Formula (A), (I), (Ia), (Ib) (II), (III), (IV), or (V)) comprises the steps of:

selectively oxidizing Compound 1 to Compound IIa:

In one embodiment, the conversion of Compound 1 to Compound 2 in the methods described herein (e.g., the methods of preparing a compound of Formula (A), (I), (Ia), (Ib) (II), (III), (IV), or (V)) comprises the steps of:

reducing Compound 1 to Compound IIIa:

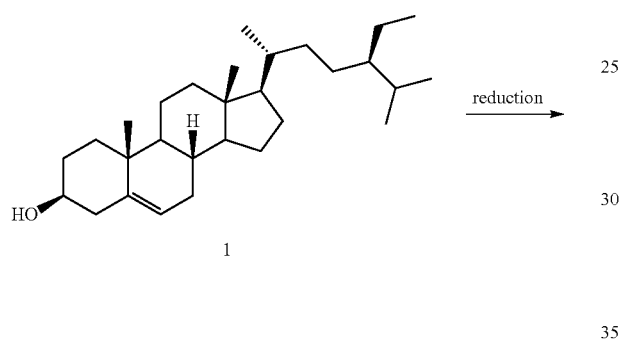

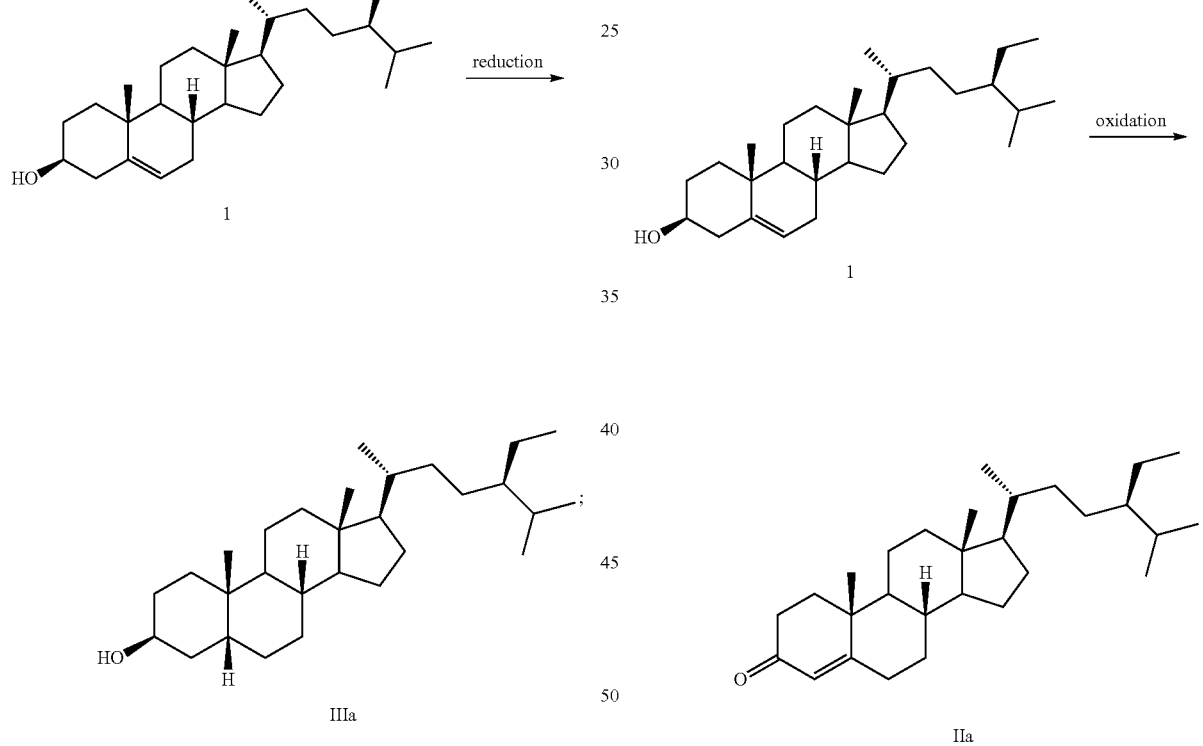

and selectively oxidizing Compound IIIa to Compound 2b:

selectively oxidizing Compound IIa to Compound IIb

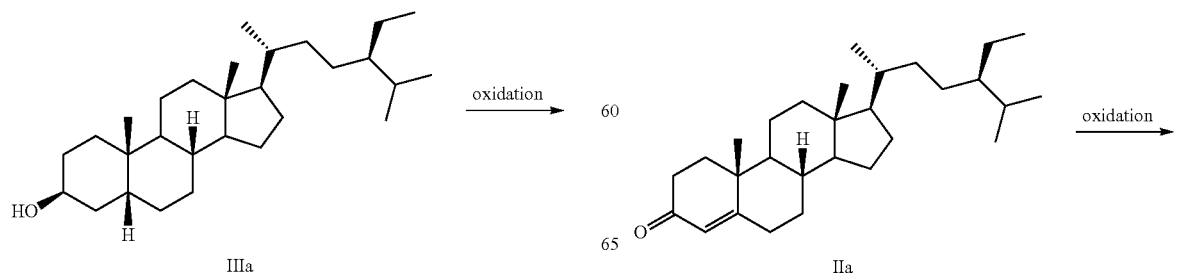

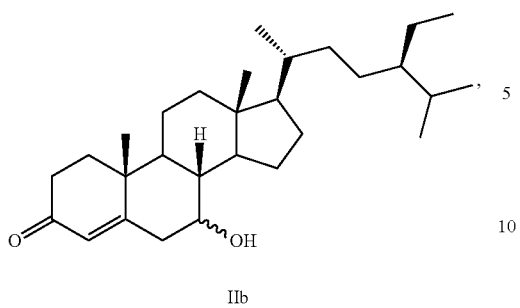

IIb wherein " ~ " indicates that the OH at the C7-position is in an α- or β-stereochemistry;

selectively reducing Compound IIb to Compound IIc:

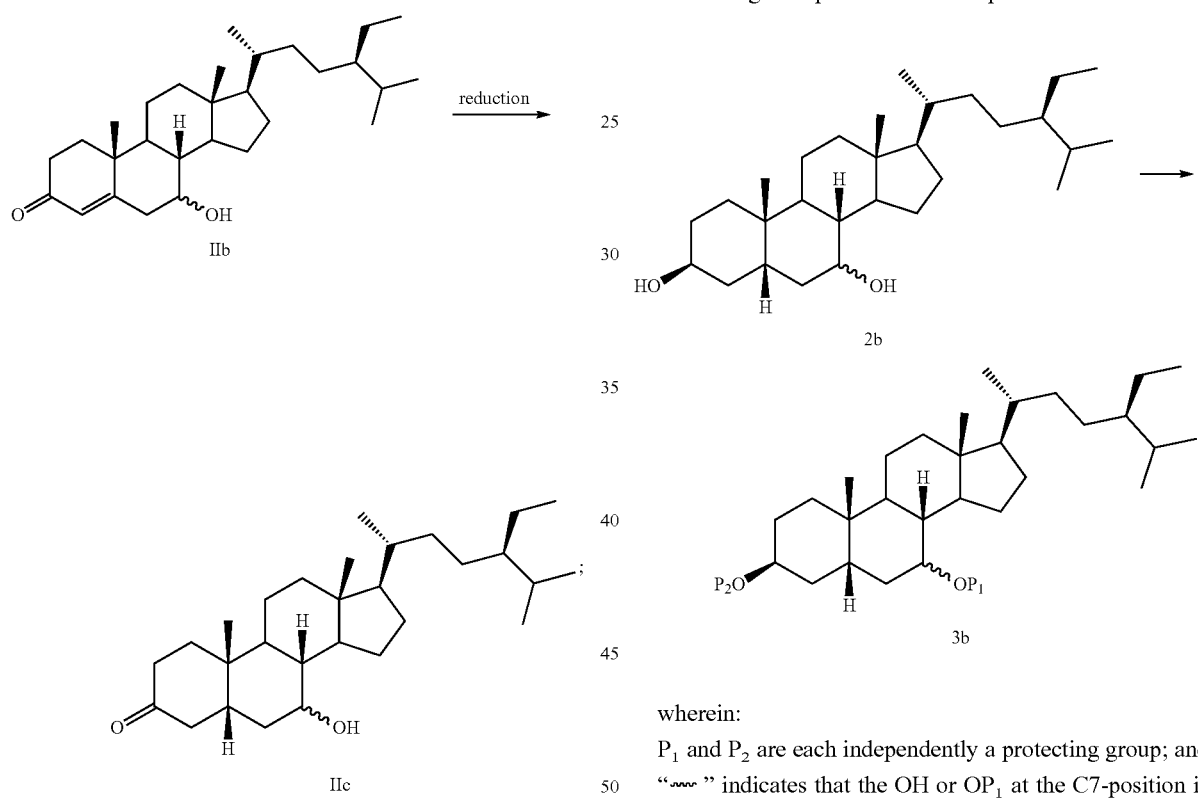

and
reducing Compound IIc to Compound 2a:

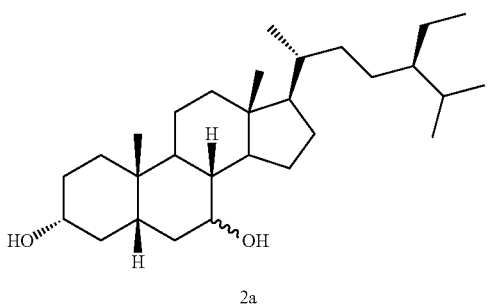

2a

In one embodiment, the conversion of Compound 2 to Compound 5 in the methods described herein (e.g., the methods of preparing a compound of Formula (A), (I), (Ia), (Ib), (II), (III), (IV), or (V)) comprises the steps of:

converting Compound 2b to Compound 3b:

wherein:

$P_1$ and $P_2$ are each independently a protecting group; and

" ~ " indicates that the OH or $OP_1$ at the C7-position is in an α- or β-stereochemistry.

In an alternative scheme, oxidation and protection at C3 and C7 are carried out prior to side chain degradation to the C24 acid and migration of the C5-C6 olefin.

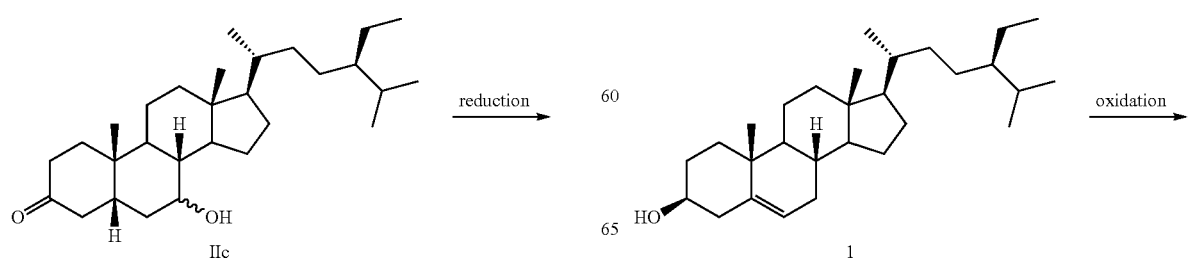

-continued

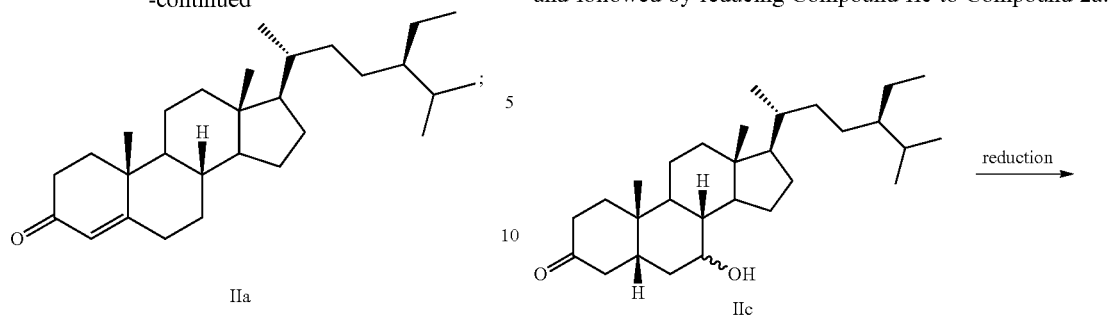

Compound 1 is oxidized at C3 to the corresponding ketone (Compound IIa). Thereafter, Compound IIa is further oxidized to Compound IIb

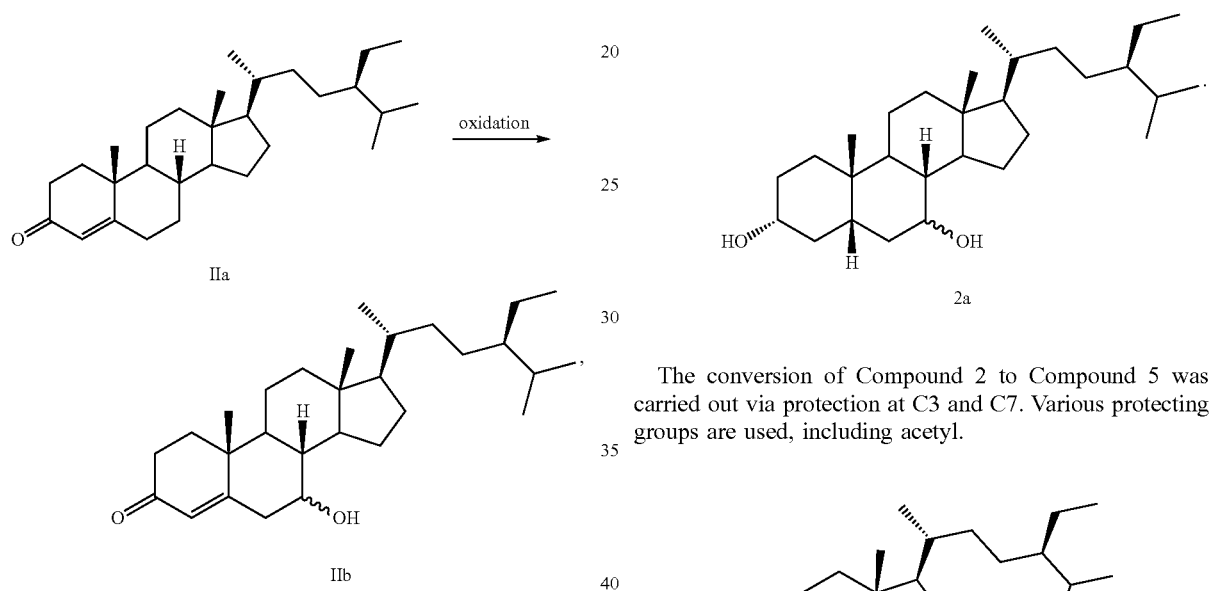

Compound IIb is then selectively reduced to Compound IIc:

and followed by reducing Compound IIc to Compound 2a:

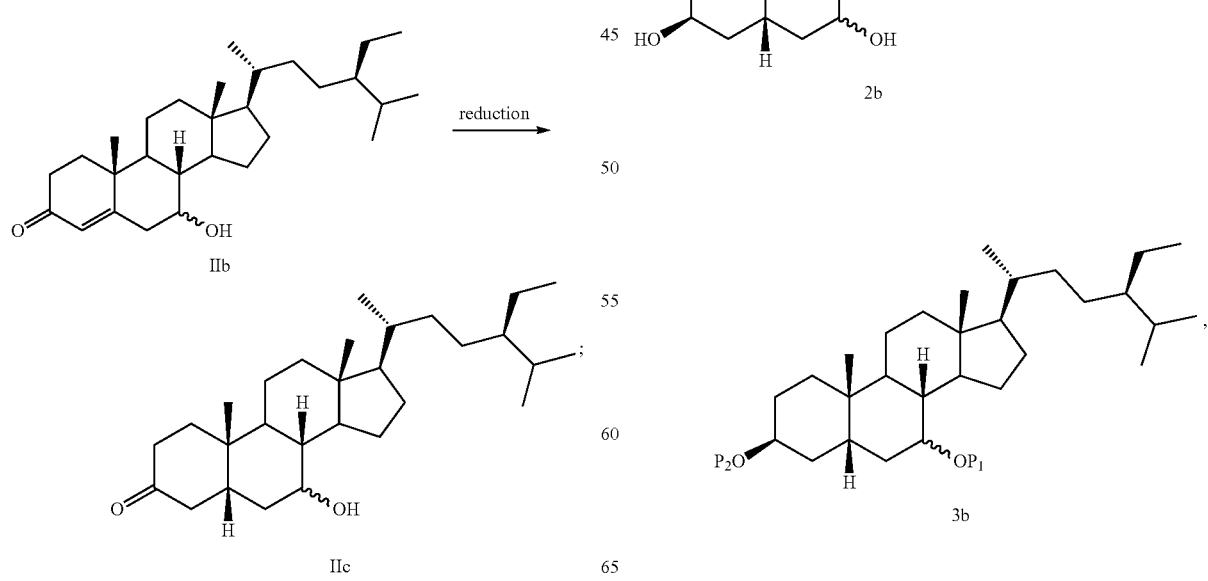

The conversion of Compound 2 to Compound 5 was carried out via protection at C3 and C7. Various protecting groups are used, including acetyl.

Compound 3b is then subjected to enzymatic or microbial oxidation conditions to generate Compound Ya.

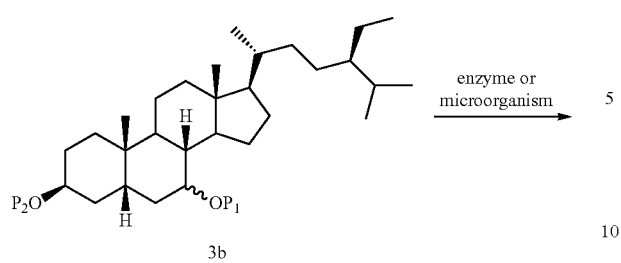

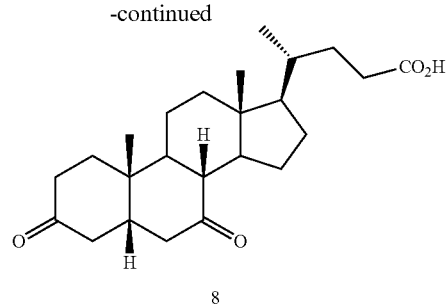

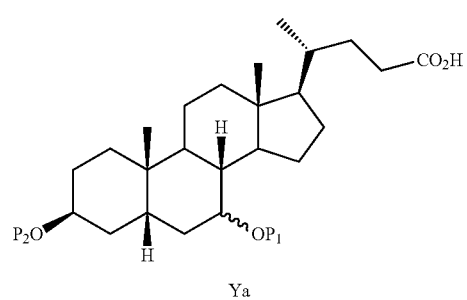

Compound Ya is subjected to deprotection conditions for removal of the $P_1$ and $P_2$ protecting groups to generate Compound 7b.

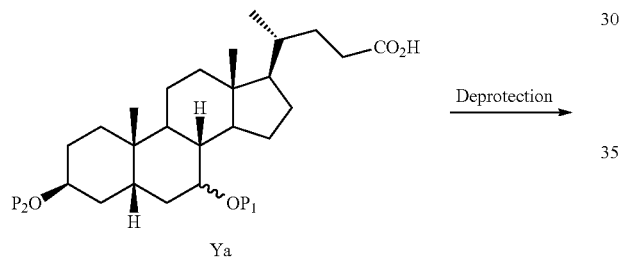

Compound 7b is subjected to oxidation conditions (e.g., NaOCl) to generate Compound 8.

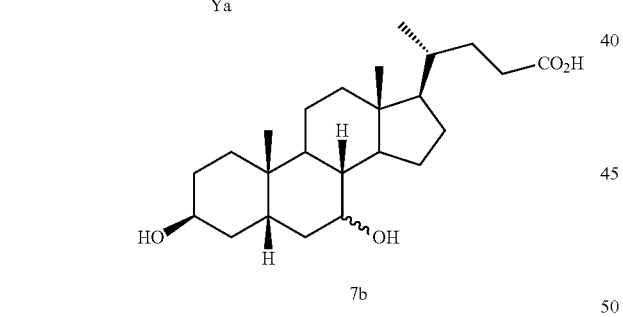

Compound 8 is subjected to ketone reduction conditions (e.g., $NaBH_4$) to generate Compound 9. In one embodiment, the conversion of Compound 1 to Compound 2 in the methods described herein (e.g., the methods of preparing a compound of Formula (A), (I), (Ia), (Ib) (II), (III), (IV), or (V)) comprises the steps of:

reducing Compound 1 to Compound IIIa:

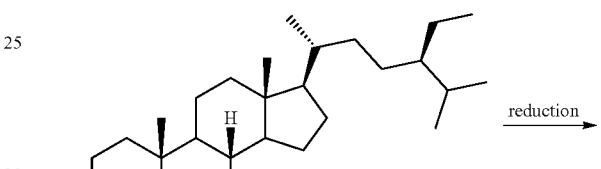

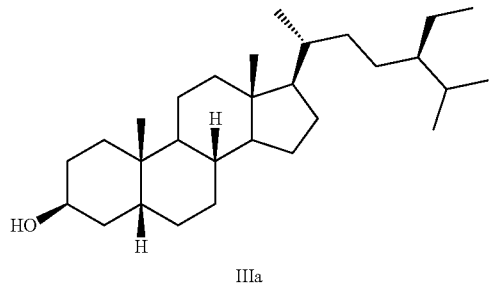

and selectively oxidizing Compound IIIa to Compound 2b:

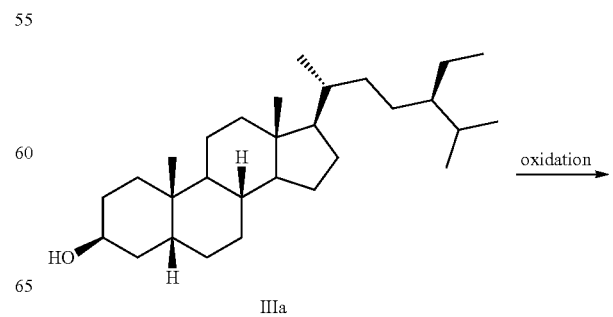

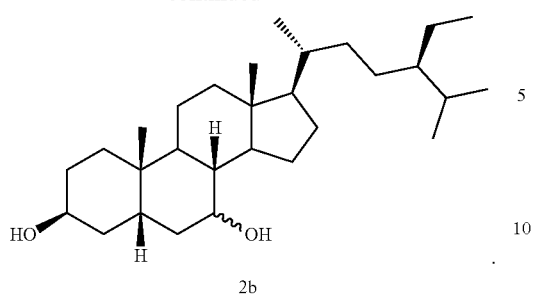

2b wherein " ~ " indicates that the OH at the C7-position is in an α- or β-stereochemistry.

In one embodiment, the conversion of Compound 1 to Compound 2 in the methods described herein (e.g., the methods of preparing a compound of Formula (A), (I), (Ia), (Ib), (II), (III), (IV), or (V)) comprises the steps of:

selectively oxidizing Compound 1 to Compound IIa:

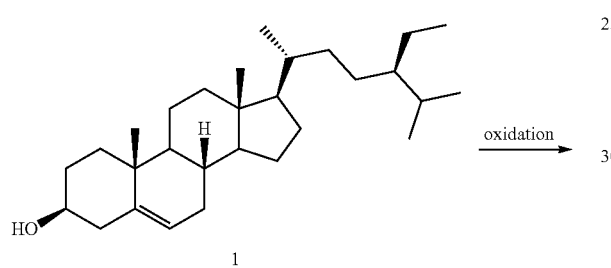

1

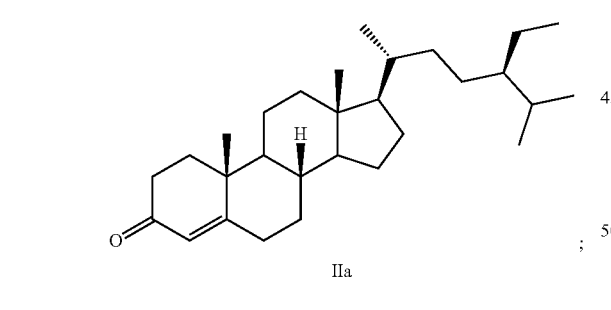

IIa selectively oxidizing Compound IIa to Compound IIb

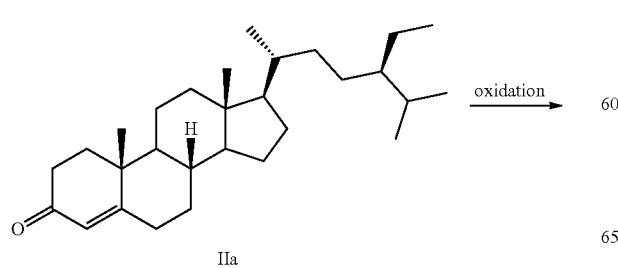

IIa

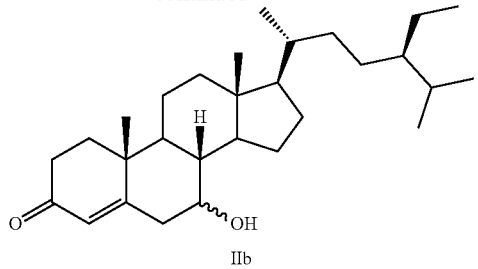

IIb wherein " ~ " indicates that the OH at the C7-position is in an α- or β-stereochemistry;

selectively reducing Compound IIb to Compound IIc:

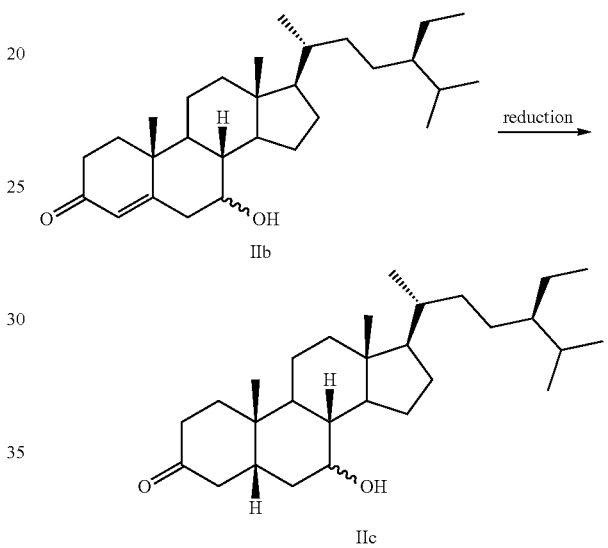

IIb

IIc and reducing Compound IIc to Compound 2a:

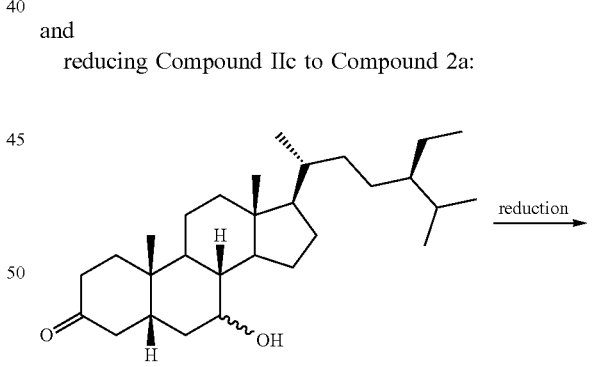

IIc

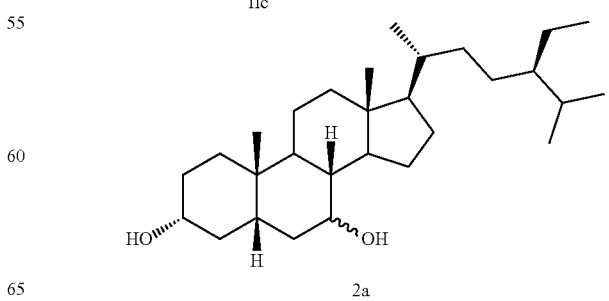

2a

In one embodiment, the conversion of Compound 2 to Compound 5 in the methods described herein (e.g., the methods of preparing a compound of Formula (A), (I), (Ia), (Ib), (II), (III), (IV), or (V)) comprises the steps of:

converting Compound 2b to Compound 3b:

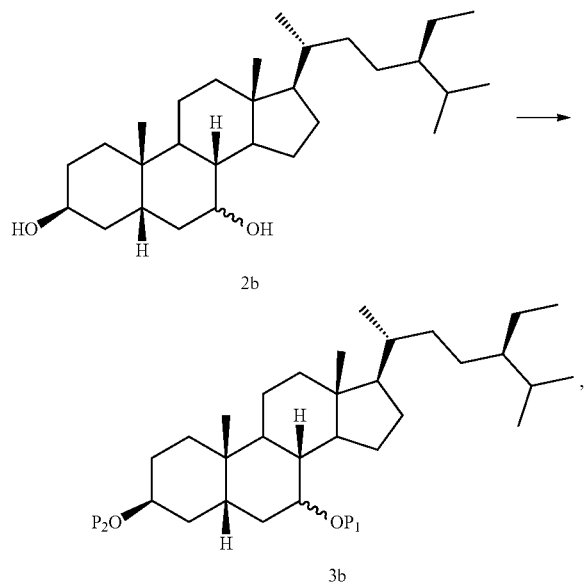

wherein:

P$_1$ and P$_2$ are each independently a protecting group; and

"⁓" indicates that the OH or OP$_1$ at the C7-position is in an α- or β-stereochemistry; converting Compound 3b to Compound 4b by way of intermediate 4b':

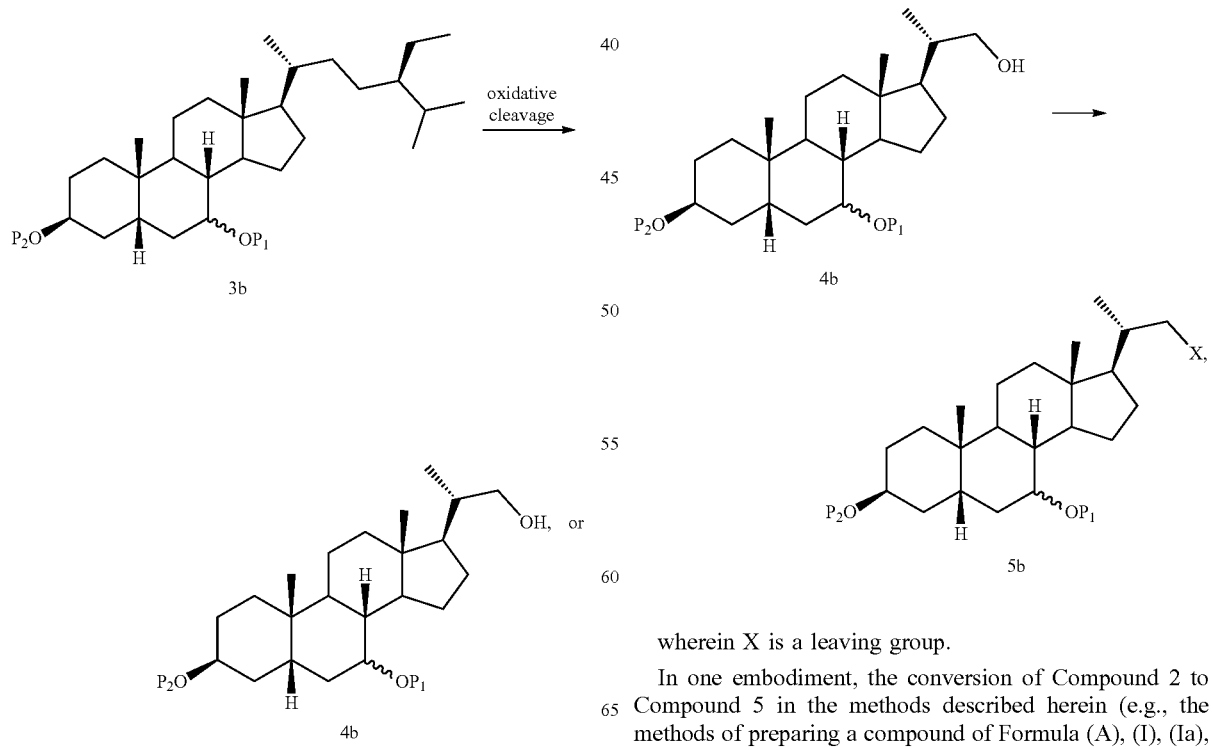

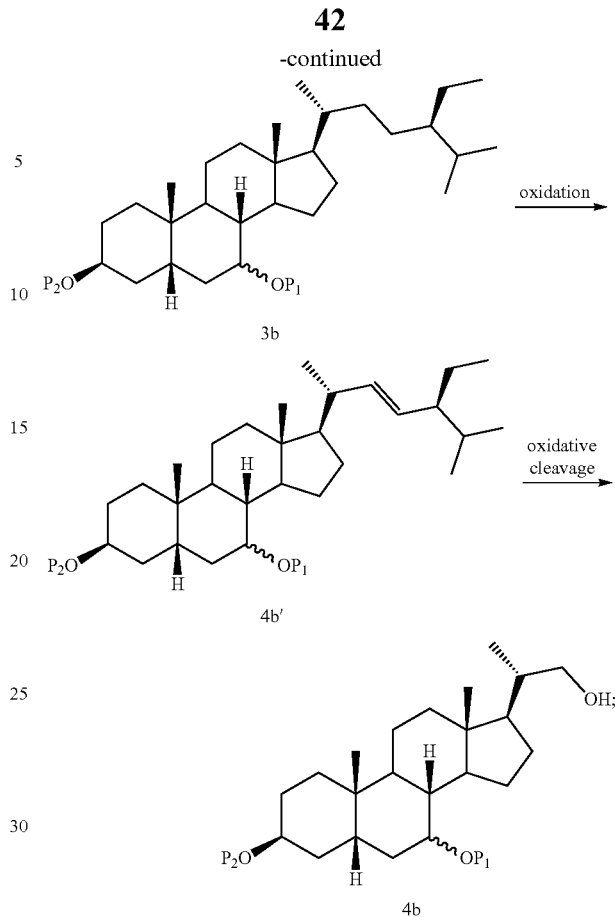

converting Compound 4b to Compound 5b:

wherein X is a leaving group.

In one embodiment, the conversion of Compound 2 to Compound 5 in the methods described herein (e.g., the methods of preparing a compound of Formula (A), (I), (Ia), (Ib), (II), (III), (IV), or (V)) comprises the steps of:

converting Compound 2a to Compound 3a:

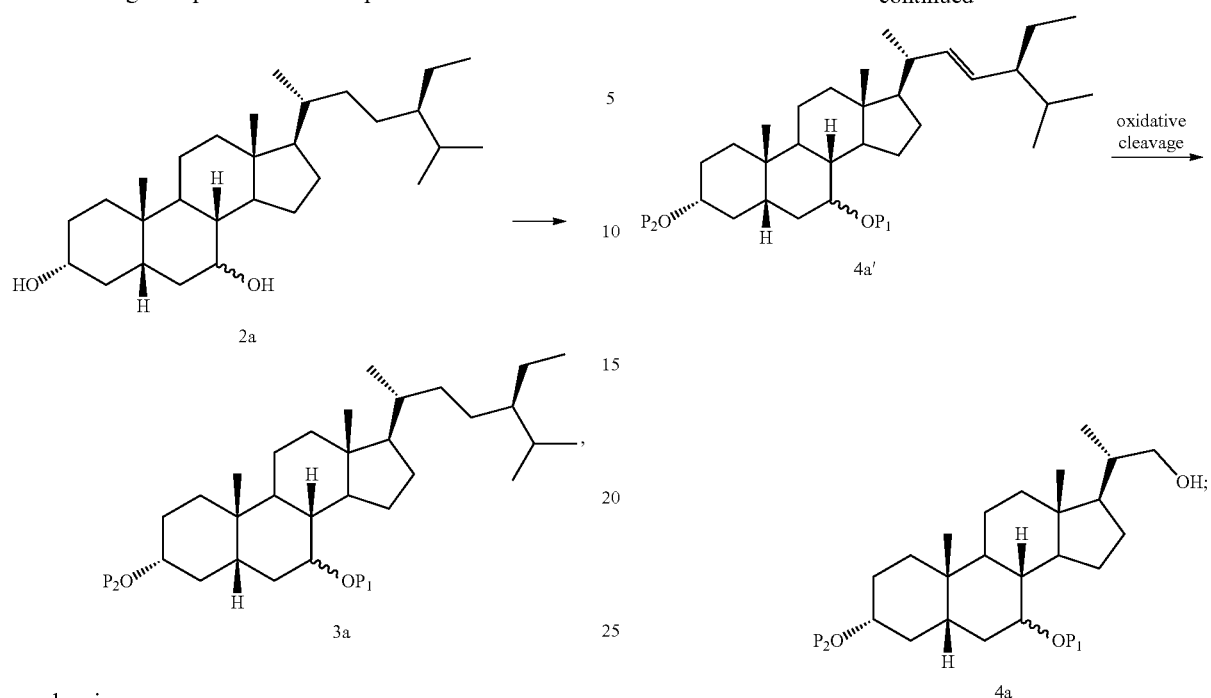

wherein:
P$_1$ and P$_2$ are each independently a protecting group; and
"⁓" indicates that the OH or OP$_1$ at the C7-position is in an α- or β-stereochemistry;
converting Compound 3a to Compound 4a by way of intermediate 4a':

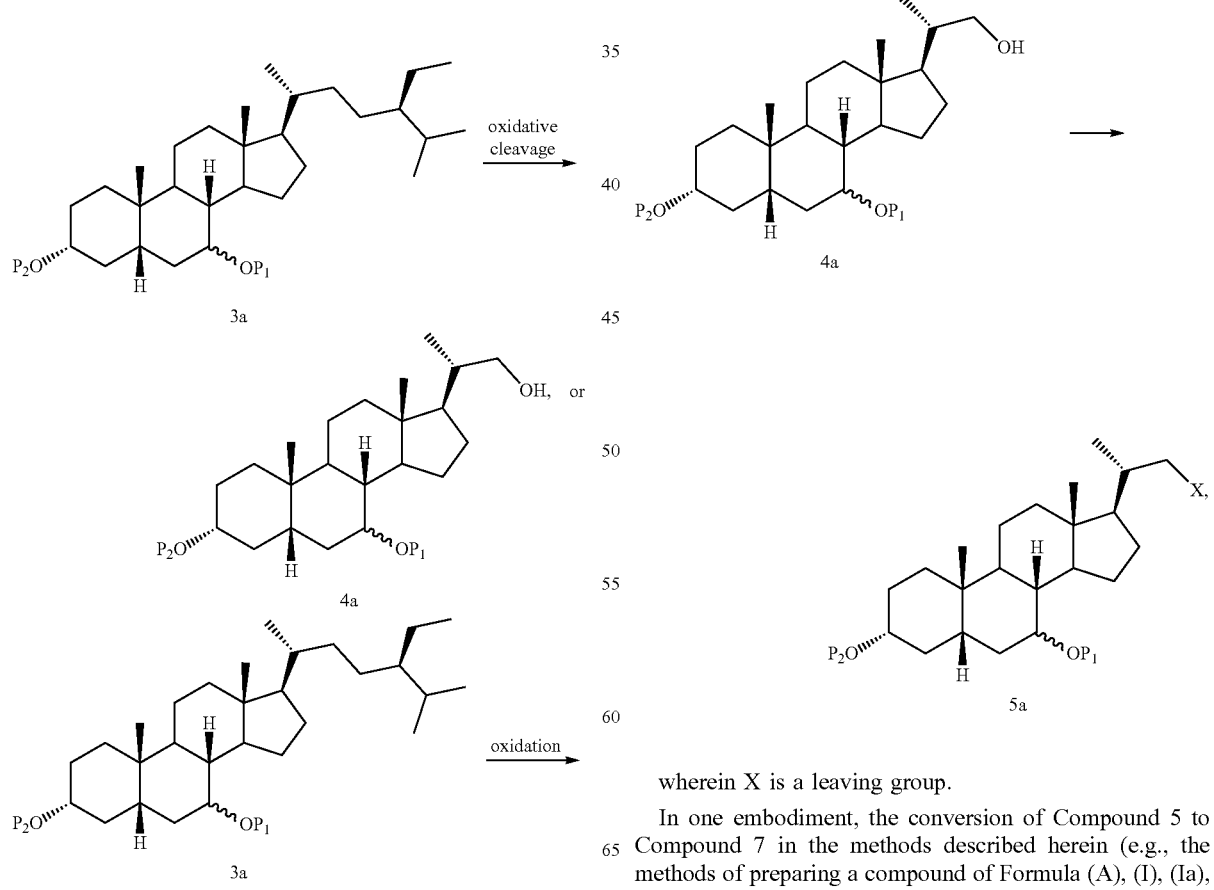

converting Compound 4a to Compound 5a:

wherein X is a leaving group.

In one embodiment, the conversion of Compound 5 to Compound 7 in the methods described herein (e.g., the methods of preparing a compound of Formula (A), (I), (Ia), (Ib), (II), (III), (IV), or (V)) comprises the steps of:

converting Compound 5b to Compound 6b:

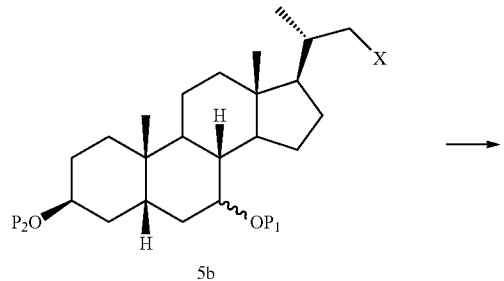

5b converting Compound 5a to Compound 6a:

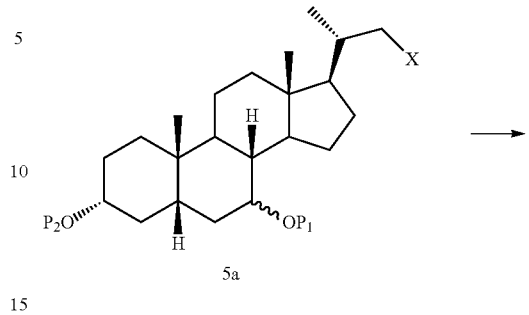

5a

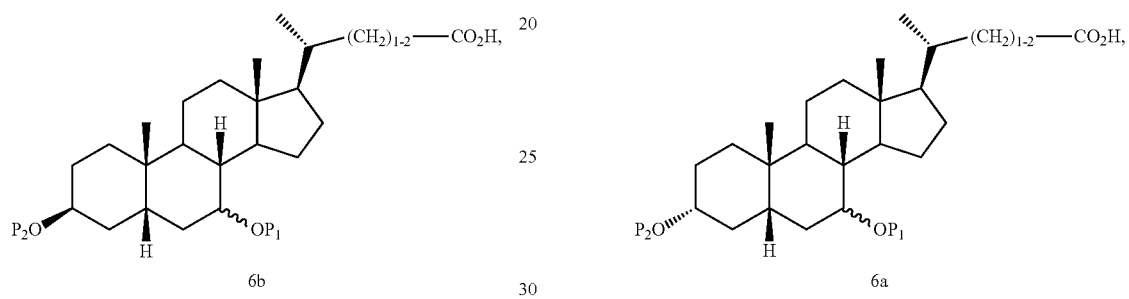

6b

6a wherein:

$P_1$ and $P_2$ are each independently a protecting group; and

" ⁓ " indicates that the OH or $OP_1$ at the C7-position is in an α- or β-stereochemistry; and deprotecting Compound 6b to form Compound 7b:

wherein:

$P_1$ and $P_2$ are each independently a protecting group; and

" ⁓ " indicates that the OH or $OP_1$ at the C7-position is in an α- or β-stereochemistry; and deprotecting Compound 6a to form Compound 7a:

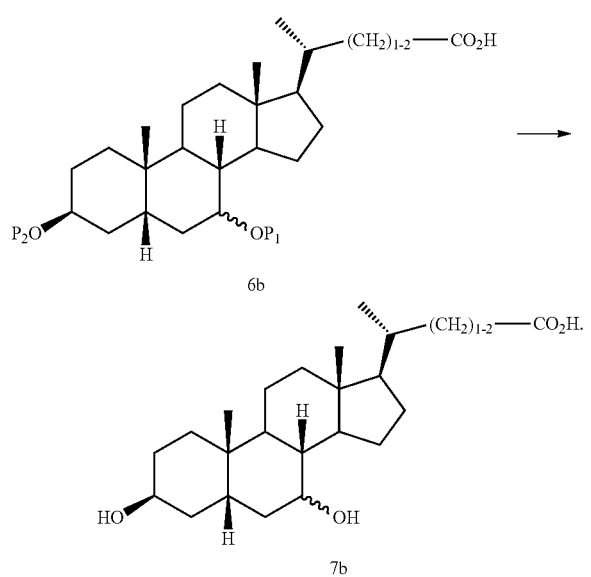

6b

7b

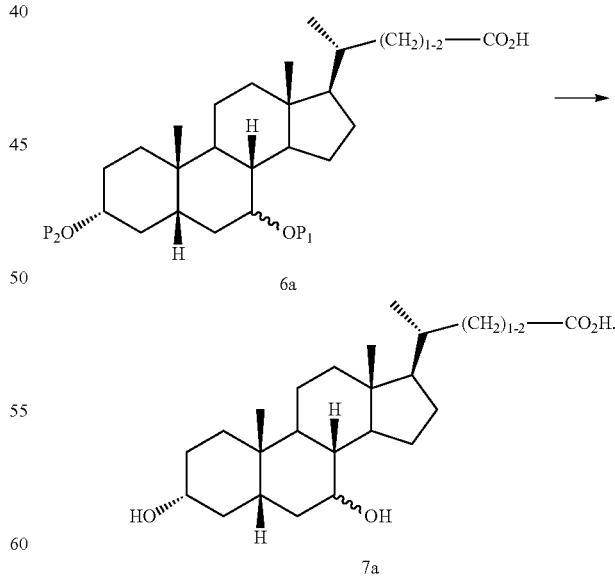

6a

7a

In one embodiment, the conversion of Compound 5 to Compound 7 in the methods described herein (e.g., the methods of preparing a compound of Formula (A), (I), (Ia), (Ib), (II), (III), (IV), or (V)) comprises the steps of:

In one embodiment, the conversion of Compound 7 to a compound of Formula (Ia) in the methods described herein (e.g., the methods of preparing a compound of Formula (A), (I), (Ia), (Ib), (II), (III), (IV), or (V)) comprises the steps of:

oxidizing Compound 7a or Compound 7b to Compound 8:

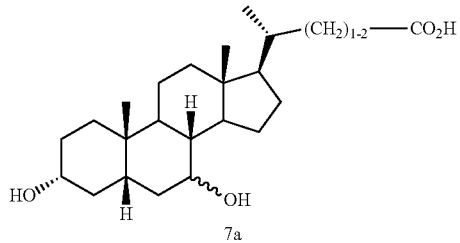
7a

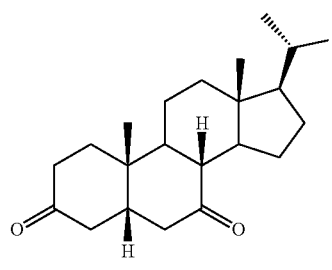
8

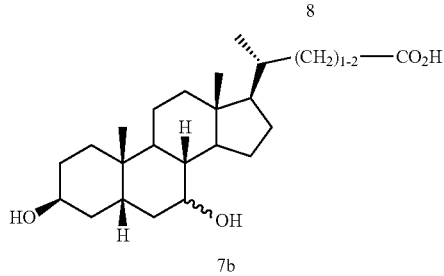
7b

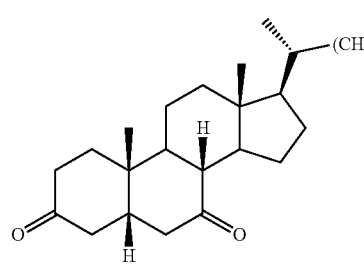
8 wherein " ~~ " indicates that the OH at the C7-position is in an α- or β-stereochemistry; and reducing Compound 8 to Compound 9:

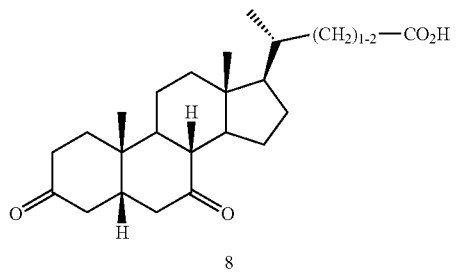
8

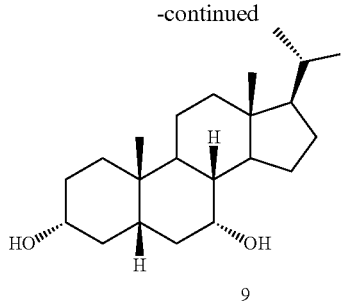
9 and optionally oxidizing Compound 9 to Compound 10:

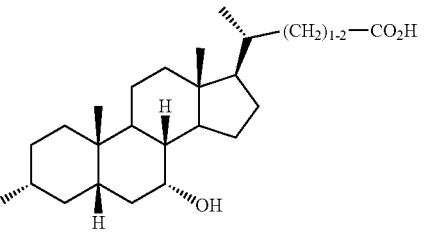
9

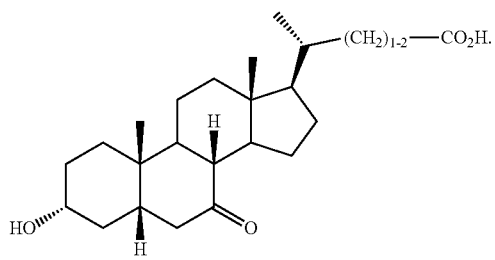
10

In one embodiment, the conversion of Compounds 7a and 7b to a compound of Formula (Ib) in the methods described herein (e.g., the methods of preparing a compound of Formula (A), (I), (Ib), (II), (III), (IV), or (V)) comprises the steps of:

oxidizing Compound 7a or Compound 7b to Compound 8:

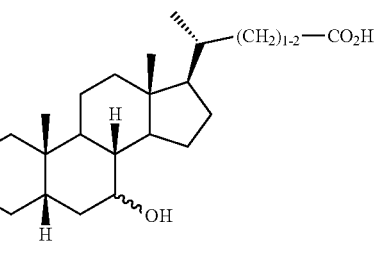
7a

-continued

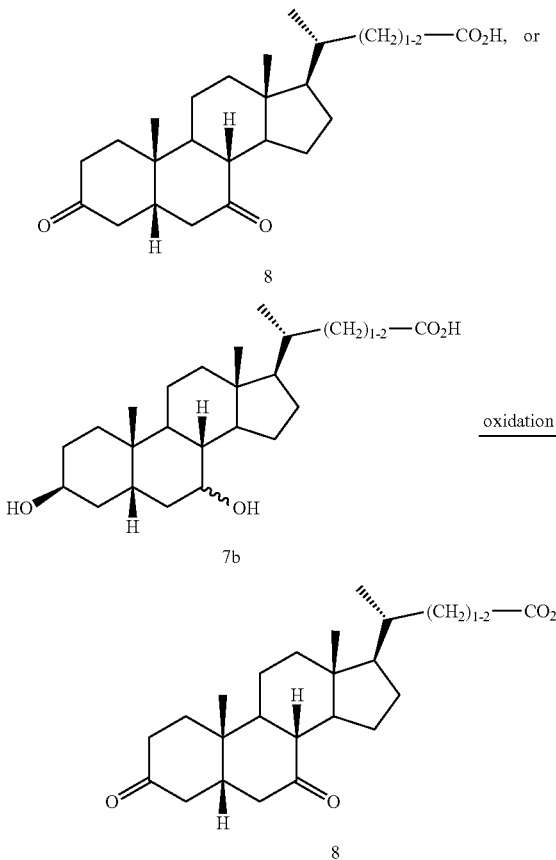

wherein " ～ " indicates that the OH at the C7-position is in an α- or β-stereochemistry; and reducing Compound 8 to Compound 9:

Selectively oxidizing Compound 9 to Compound 10:

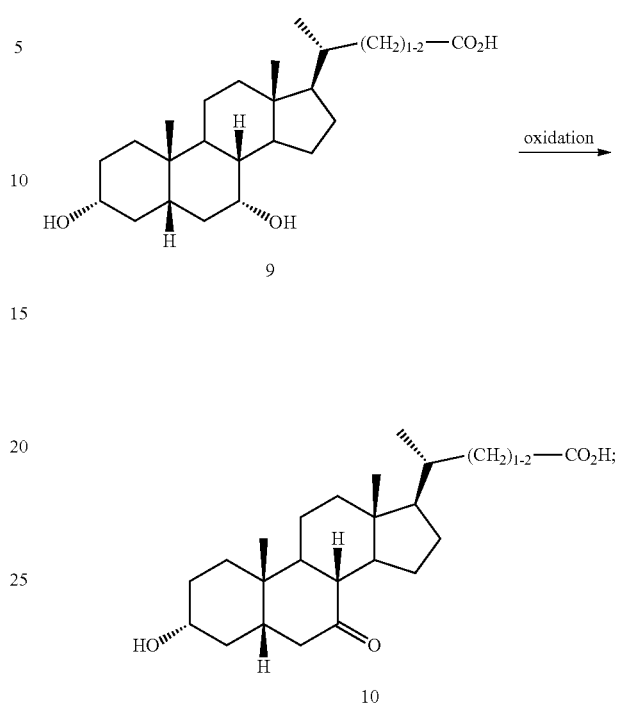

and alkylating Compound 10 to a compound of Formula (Ib):

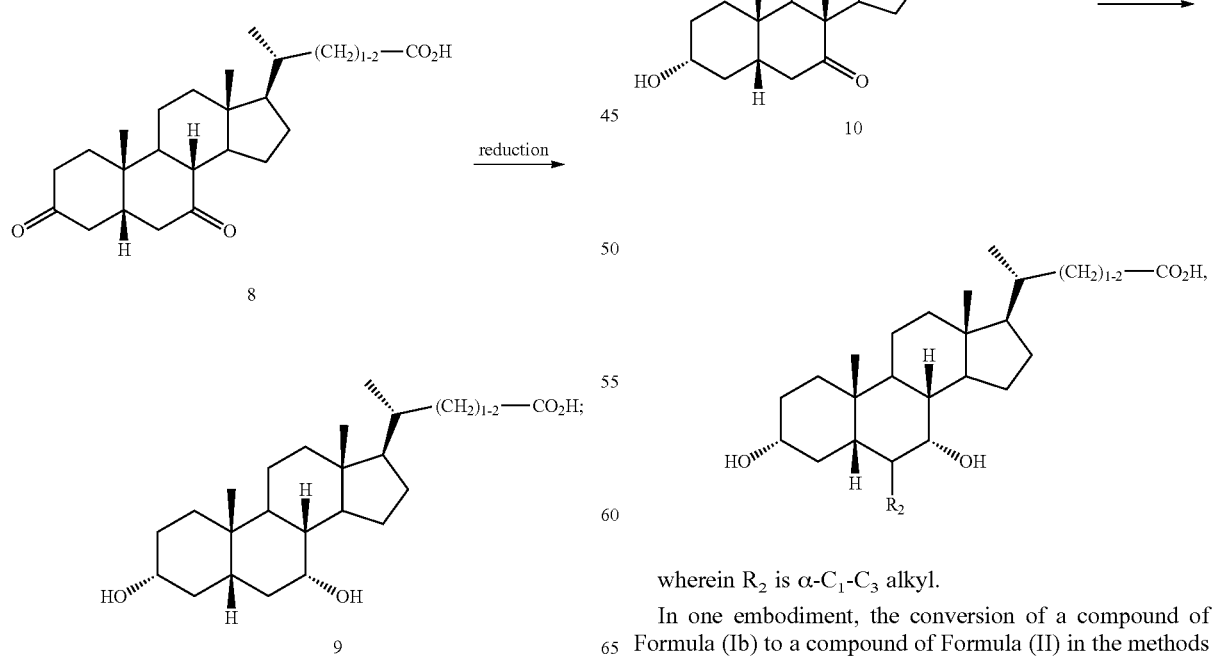

wherein $R_2$ is α-$C_1$-$C_3$ alkyl.

In one embodiment, the conversion of a compound of Formula (Ib) to a compound of Formula (II) in the methods described herein (e.g., the methods of preparing a compound of Formula (A) or (II)) comprises the step of:

oxidizing a compound of Formula (Ib) to a compound of Formula (IIa):

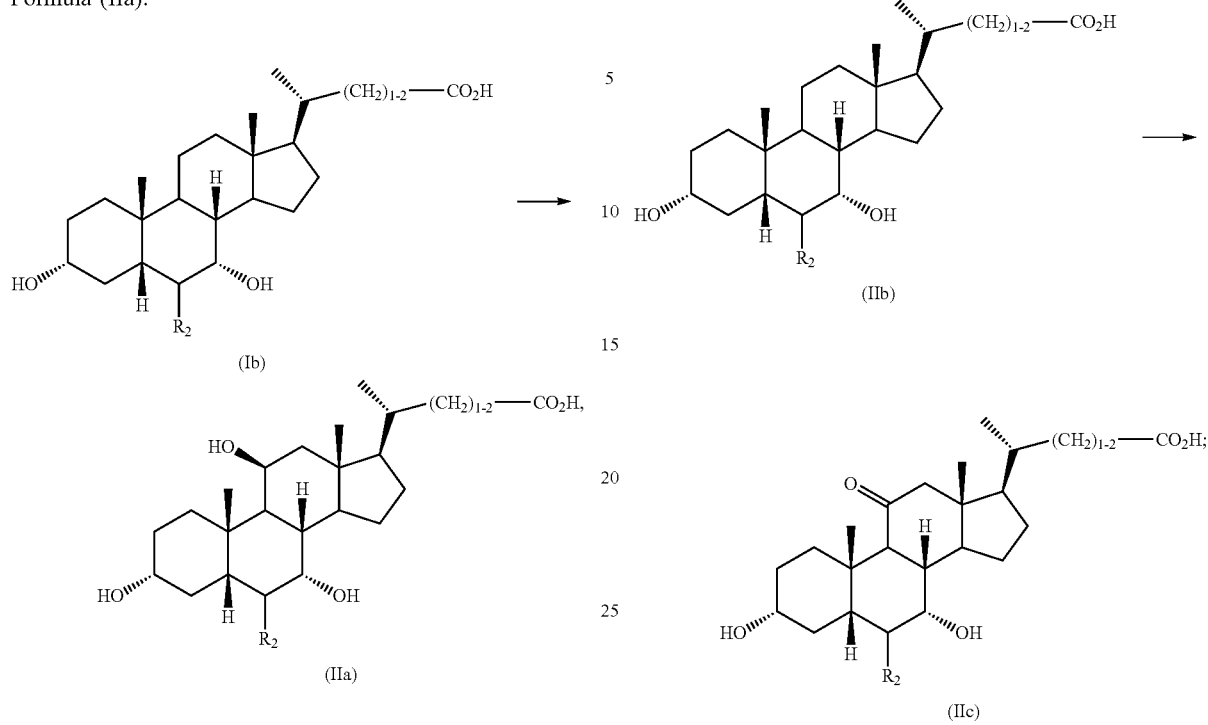

wherein $R_2$ is $\alpha$-$C_1$-$C_3$ alkyl.

In one embodiment, the conversion of a compound of Formula (Ib) to a compound of Formula (II) in the methods described herein (e.g., the methods of preparing a compound of Formula (A), (II), (III), (IV), or (V)) comprises the step of:

oxidizing a compound of Formula (Ib) to a compound of Formula (IIb):

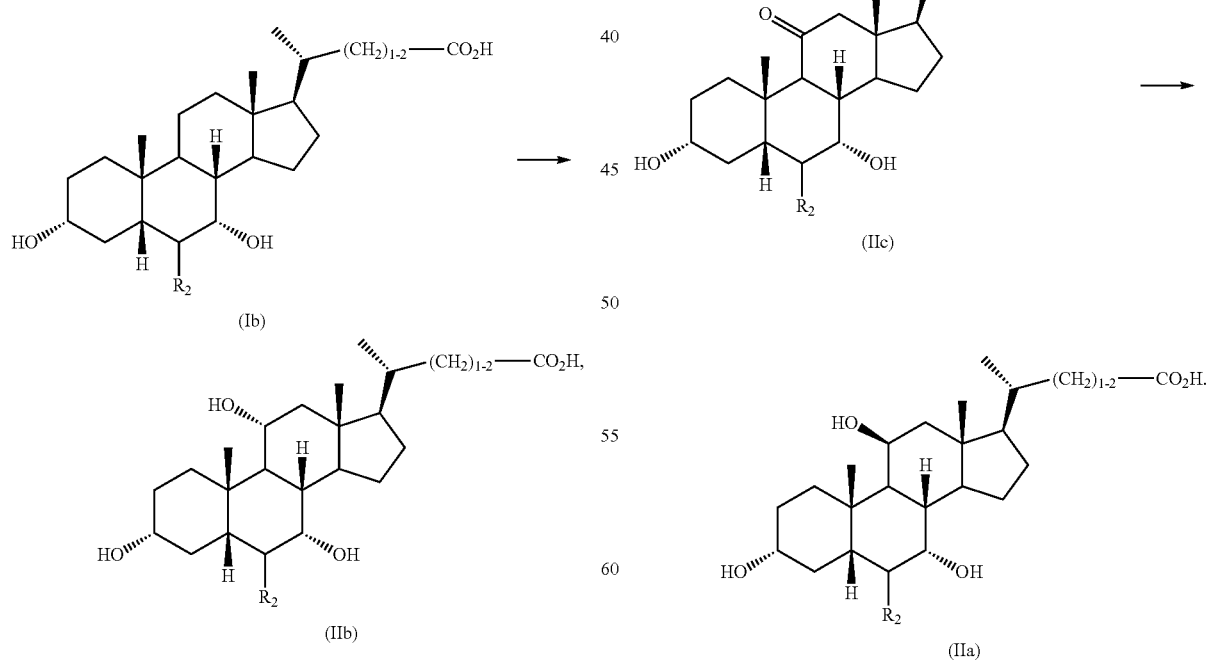

wherein $R_2$ is $\alpha$-$C_1$-$C_3$ alkyl;

optionally selectively oxidizing the compound of Formula (IIb) to a compound of Formula (IIc):

and optionally reducing the compound of Formula (IIc) to a compound of Formula (IIa):

In one embodiment, the oxidation of Compound 1a to Compound Ia:

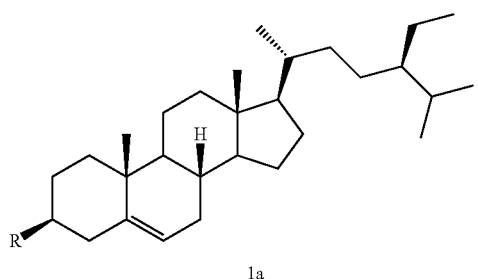

Ia

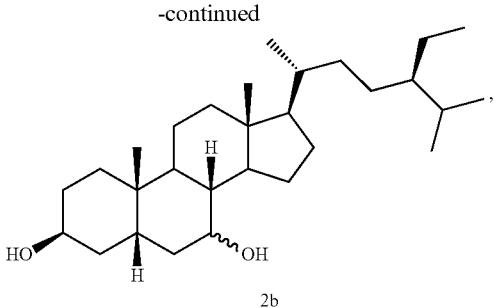

2b or the oxidation of Compound IIa to Compound IIb:

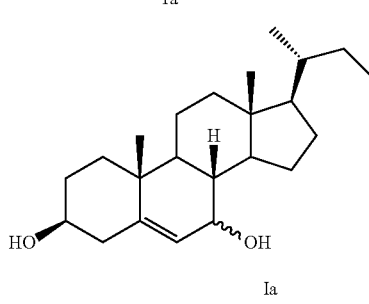

IIa or the oxidation of Compound Xa to Compound Xb:

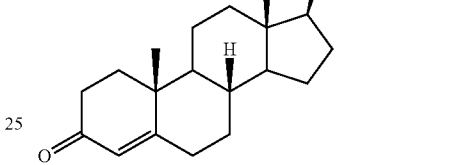

Xa

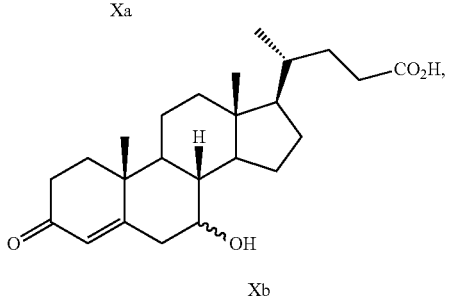

Xb

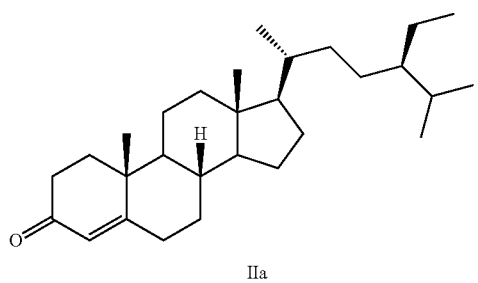

IIb or the oxidation of Compound IIIa to Compound 2b:

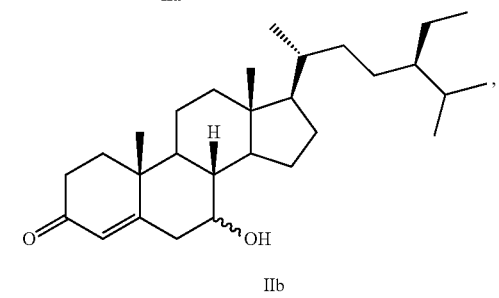

IIIa is catalyzed by a cytochrome P450 monooxygenase (e.g., CYP7A) or other enzyme that is capable of catalyzing a stereoselective oxidation reaction. Reaction conditions relating to the stereoselective enzymatic oxidation of IIa to IIb can be found in several references, e.g. Zakeli-Marvic and Belic, 1987, Journal of Steroid Biochemistry, 28, 197; and Stone, et al., 1955, JACS, 77, 3926. In one embodiment, the catalysis by a cytochrome P450 monooxygenase or other enzyme capable of catalyzing a stereoselective oxidation reaction is conducted by a natural or genetically modified microorganism (e.g., a bacterium, a fungus, an algae, a prokaryotic cell, an eukaryotic cell, an insect cell, or a mammalian cell (e.g., a human cell)) which expresses the cytochrome P450 monooxygenase (e.g., CYP7A) or other enzyme capable of catalyzing a stereoselective oxidation reaction. In one embodiment, the stereoselective oxidative catalysis by a cytochrome P450 monooxygenase or other enzyme is conducted by a microorganism. In one embodiment, the microorganism is selected from the group consisting of *Absidia, Aspergillus, Cephalosporium, Cunningamella, Curvularia, Diplodia Dothideales, Fusarium, Gibberella, Helminthosporium, Hypocreales, Mucor, Mucorales, Rhizopus, Saccharomyces*. In one embodiment, the microorganism is selected from *Cephalosporium aphidicola, Cladosporium herbarum, Colletotrichum lini, Fusarium culmorum, F. moniliforme, F. oxysporum, Mucor piriformis, M. plumbeus, Rhizopus stolonifer, Botryodiplo-* dia theobromae IFO 6469, *Diplodia gossypina* ATCC 28570, DSM 62-678, DSM 62-679, *Botryosphaeria ribis* ATCC 22802, *Botryosphaeria berengeriana* ATCC 12557, and *Botryosphaeria rhodina* CBS 374.54, CBS 287.47 and CBS 306.58. In one embodiment, the microorganism is selected from the Pleosporaceae family (e.g., *Curvularia lunata* VKPM F-981, *Alternaria alternata*, or *Bipolaris sorokiniana* (=*Helminthosporium*)), the Hypocreaceae family (e.g., *Fusarium* sp.), and the Mucoraceae family (e.g., *Rhizopus nigricans*), *Arthrobacter* sp. (e.g., *Arthrobacter polychromogene, Arthrobacter niigatensis, Arthrobacter defluvii*), *Rhodococcus* sp. (e.g., *Rhodococcus pyridinivorans, Rhodococcus erythropolis, Rhodococcus opacus, Rhodococcus ruber, Rhodococcus globerulus, Rhodococcus wratislaviensis*), *Pseudomonas* sp. (e.g., *Pseudomonas syringiae, Pseudomonas fluorescens*), *Lactobacillus* sp. (e.g., *Lactobacillus mesenter, Lactobacillus sake, Lactobacillus farciminis, Lactobacillus kefiri*), *Burkholderia* sp. (e.g., *Burkholderia pyrrocinia, Burkholderia xenovorans, Burkholderia multivorans*), *Xanthobacter* sp. (e.g., *Xanthobacter autotrophicus, Xanthobacter tagetidis*), *Furasium* sp. (e.g., *Fusarium oxysporum*), Chlorophyceae (e.g., *Dunaliella minuta, Coccomyxa elongata, Trebouxia decolorans, Chlorella ellipsoidea, Chlorella saccharophila, Chlorella pringsheimii, Trebouxia* sp., *Dunaliella primolecta*), Prasinophyceae (e.g., *Tetraselmis tetrathele, Tetraselmis chuff, Tetraselmis sueica, Pyramimonas gelidicola*), Cyanobacteria (e.g., *Anacystis nidulans, Fremyella diplosiphon, Cvanidium caldarium, Microcystis aeruginosa, Anabaena cylindrica, Spirulina platensis, Spirulina* sp., *Calothrix* sp., *Nostoc commune*), Chrysophyceae (e.g., *Ochromonas danica, Ochromonas malhamensis, Ochromonas sociabilis*), Xanthophyceae (e.g., *Botrydium granulatum, Monodus subterraneus, Tribonema aequale*), Euglenophyceae (e.g., *Euglena gracilis, Astasia longa*), Bangiophyceae (e.g., *Goniotrichum elegans, Porphyridium cruentum, Porphyridium aeurigeum*), Cryptophyceae (e.g., *Cryptomonas* sp., *Nematochrysopsis roscoffensis*), Raphidophyceae (*Fibrocapsa japonica*), *Chrysochromulina polylepis, Prymnesium patellifera, Ochrosphaera neapolitana, Ochrosphaera verrucosa, Pavlova lutheri, Pavlova lutheri, Emiliania huxleyi, Isochrysis galbana, Isochrysis galbana, Isochrysis* sp., *Isochrysis* sp., *Chrysotila lamellosa, Chrysotila lamellosa, Chrysotila stipitata, Hymenomomas carterae, Coccolithus pelagicus, Nitzschia longissima, Melosira granulats, Thalassionema nitzschoides, Nitzschia frustulum, Chaetoceros simplex, Skeletonema costatum, Thalassiosira fluviatilis, Fragilaria* sp., *Asterionella glacialis, Biddulphia sinensis, Ciclotella nana, Vavicula pelliculosa, Nitzschia closterium, Phaeodactylum tricornutum, Phaeodactylum tricornutum, Stauroneis amphioxys, Nitzschia ovalis, Biddulphia aurita, Chaetoceros* sp., *Thalassiosira pseudonana, Thalassiosira pseudonana, Amphora exigua, Amphora* sp., *Nitzschia alba, Rhizoselenium* spp., *Gonyaulax* spp., *Peridinium foliaceum, Peridinium foliaceum, Gonyaulax diegensis, Pyrocystis lunula, Gonyaulax polygramma, Gymnodinium wilczeki, Glenodinium hallii, Noctiluca milaris, Gymnodinium simplex*, and *Prorocentrum cordatum*. In one embodiment, the microorganism is *Curvularia lunata* VKPM F-981. In one embodiment, R is OH.

In one embodiment, the oxidation of Compound 1a to Compound Ia:

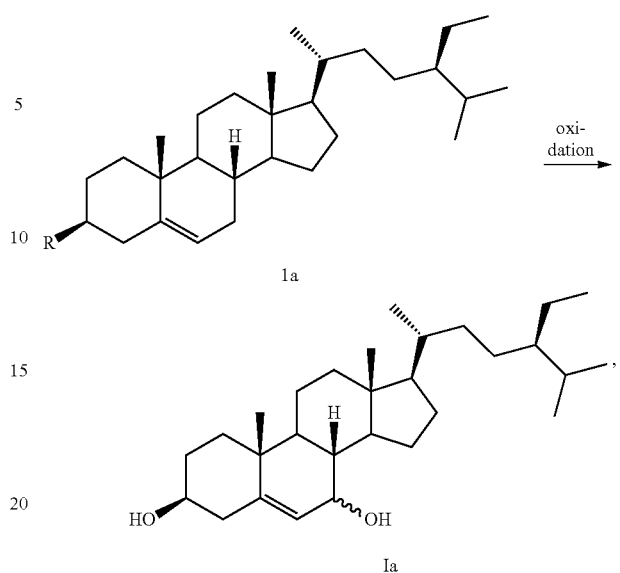

is conducted by reacting Compound 1a with a selective oxidant. In one embodiment, the oxidant is tert-butyl hydroperoxide. In one embodiment, the reaction is conducted via copper allylic oxidation. In one embodiment, the copper allylic oxidation comprises a copper catalyst. In one embodiment, the copper catalyst is selected from CuCl, $CuCl_2$, CuBr, CuI, and Cu(I)O. In one embodiment, the copper catalyst is CuBr. In one embodiment, the copper catalyst is present in the amount of 0.5-5 equiv., 0.5-4 equiv., 0.5-3 equiv., 0.5-2.5 equiv., 1-2.5 equiv., 1.5 to 2.5 equiv., or about 2 equiv. In one embodiment, the oxidation is conducted in the presence of an inert atmosphere. In one embodiment, the oxidation is conducted in the presence of argon. In one embodiment, R is $OP_2$, wherein $P_2$ is a protecting group.

In one embodiment, the reduction of Compound Ia to Compound 2b:

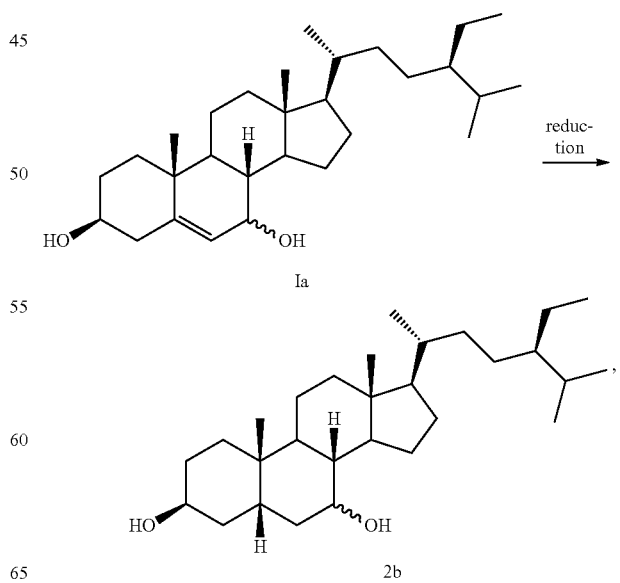

or the reduction of Compound 1 to Compound IIIa:

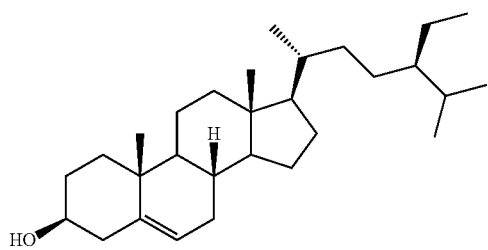

1

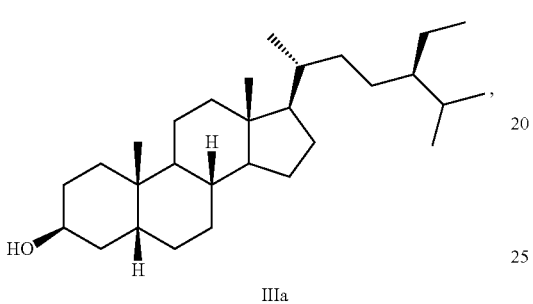

IIIa is conducted via hydrogenation. In one embodiment, the hydrogenation takes place, for example, in the presence of a catalyst. In one embodiment, the catalyst is selected from palladium catalyst (e.g., Pd/C), platinum catalyst (e.g., $PtO_2$), nickel catalyst (e.g., Raney nickel and Urushibara nickel), and copper catalyst (e.g., $Cu/Al_2O_3$), any of which may be used on or in the absence of carbon. In one embodiment, the catalyst may be used homogeneously in a solution.

In one embodiment, the conversion of Compound 1 to Compound IIa:

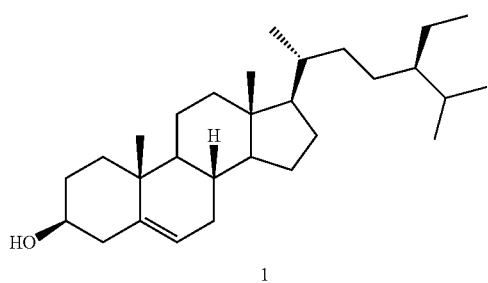

1

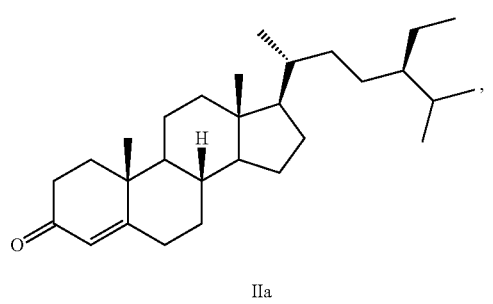

IIa or the oxidation of Compound 7b to Compound 8:

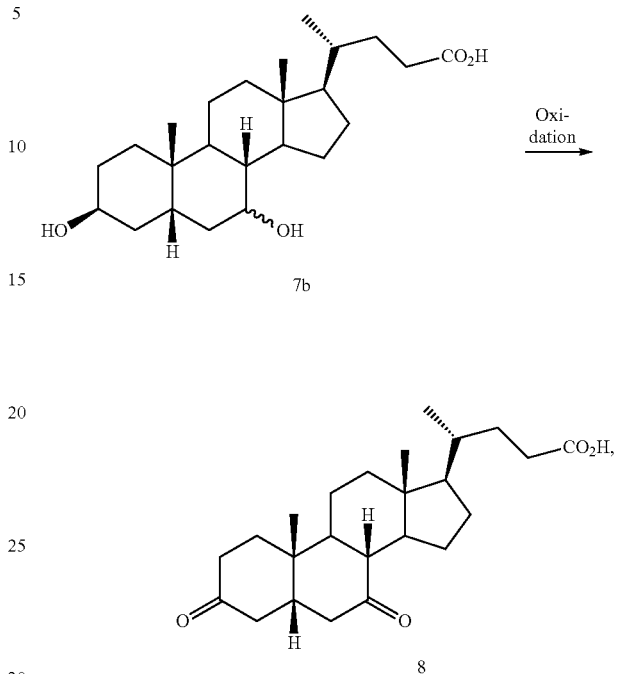

is conducted via enzymatic oxidation. See the procedure set forth in Chen and Penning, 2014, Steroids, 83, 17-26. In one embodiment, the enzymatic oxidation is conducted by a hydroxy-delta-5-steroid dehydrogenase enzyme (HSD3B7).

In one embodiment, the reduction of Compound IIb to Compound IIc:

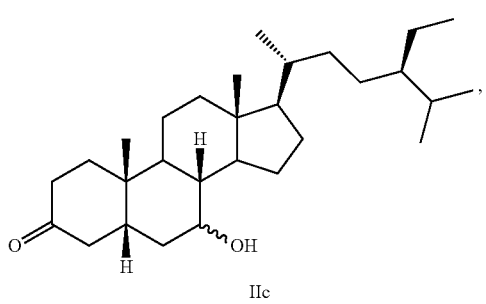

or the reduction of Compound 1 to Compound IIIa:

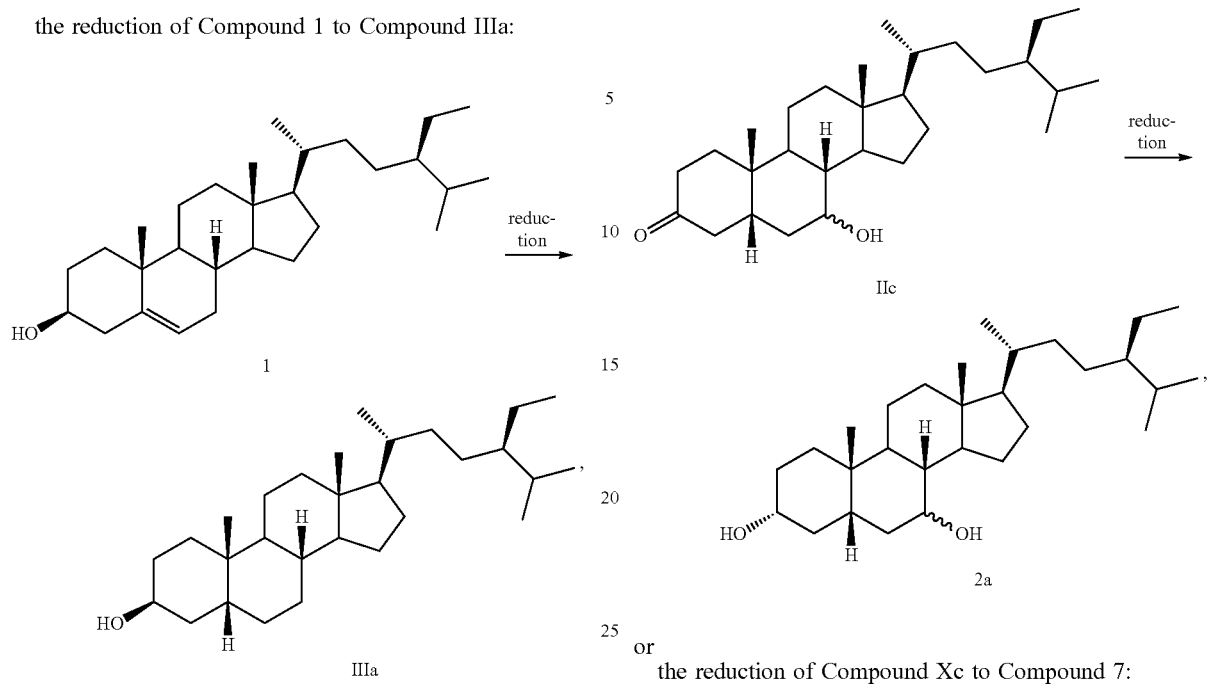

or the reduction of Compound Xb to Xc:

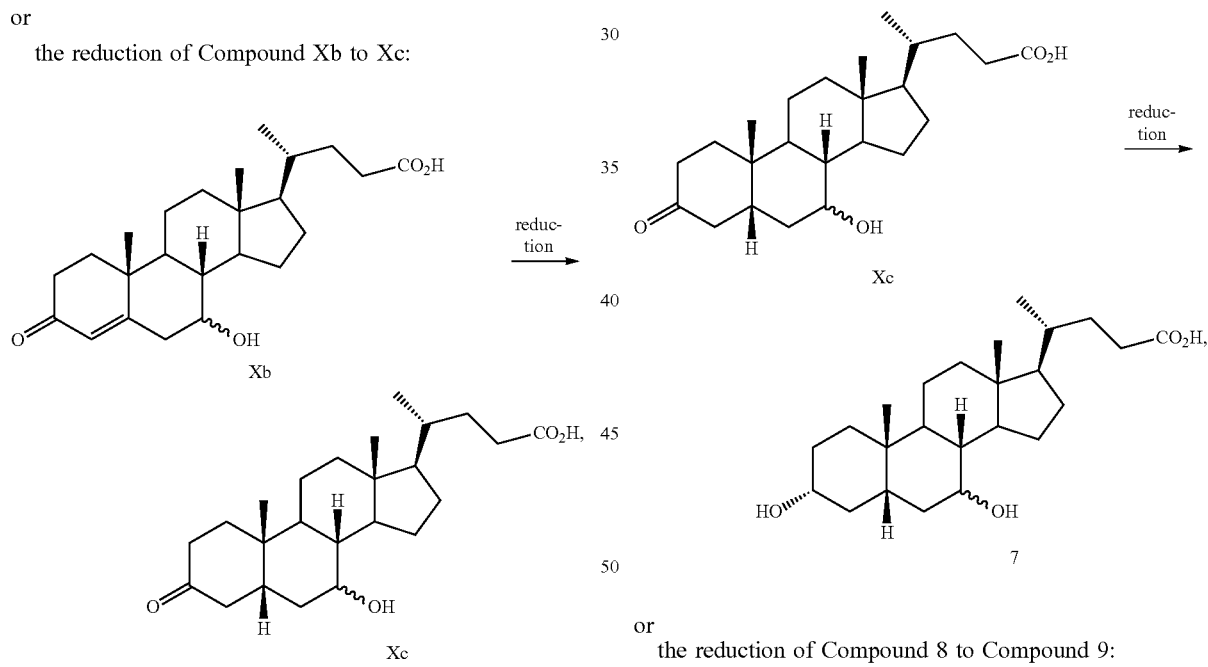

is conducted by a 5β-reductase (e.g., aldo-keto reductase family 1 (AKR1) enzyme). In one embodiment, the 5β-reductase is AKR1D1. In one embodiment, the catalysis by a 5β-reductase is conducted by a natural or genetically modified microorganism (e.g., a bacterium, a fungus, an algae, a prokaryotic cell, an eukaryotic cell, an insect cell, or a mammalian cell (e.g., a human cell)) which expresses the 5β-reductase (e.g., aldo-keto reductase family 1 (AKR1) enzyme).

In one embodiment, the reduction of Compound IIc to Compound 2a:

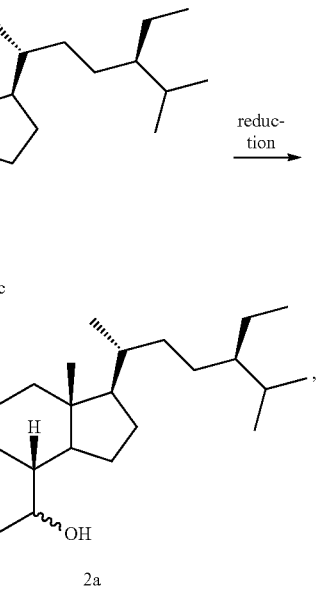

or the reduction of Compound Xc to Compound 7:

or the reduction of Compound 8 to Compound 9:

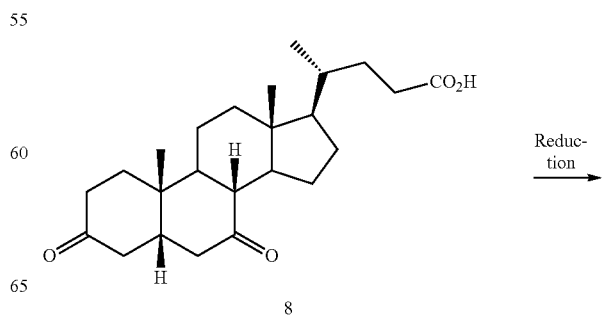

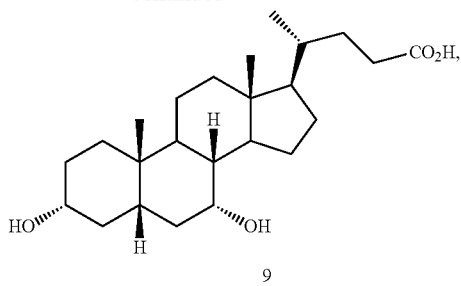

9

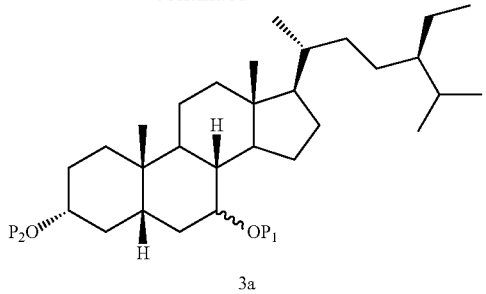

3a is achieved by treating Compound IIc with a reducing agent (e.g., NaBH$_4$, Red-Al, DIBAL-H, LiAlH$_4$, LiBH$_4$, L-Selectride, or K-Selectride).

In one embodiment, the conversion of Compound 2b to Compound 3b:

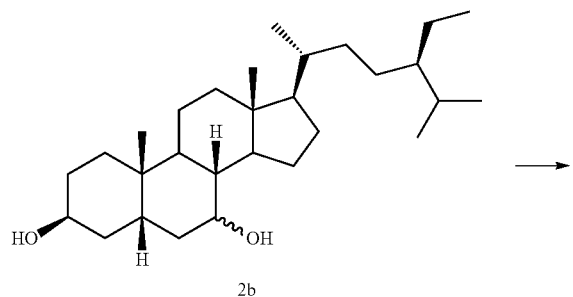

2b

↓

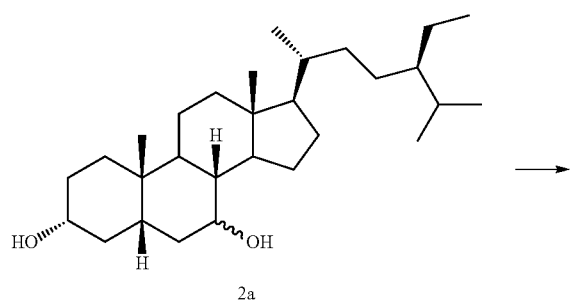

3b or the conversion of Compound 2a to Compound 3a:

2a is achieved by treating Compound 2b or Compound 2a with a protecting group P$_1$ and P$_2$. P$_1$ and P$_2$ can each independently be any protecting group that is stable/non-reactive under the reaction condition (e.g., non-reactive with an agent used in the reaction). In separate embodiments, the Compound 2b or Compound 2a can be treated with acetyl chloride (or a C$_2$-C$_6$ alkyl acid chloride), acetic anhydride, benzoyl chloride, benzoic anhydride, pivaloyl chloride, 3,4-dihydropyran, 2,3-dihydrofuran, chloromethyl ethyl ether, chloromethyl methyl ether, ethyl vinyl ether, p-methoxybenzyl chloride, p-methoxybenzyl trichloroacetimidate, chloromethyl thiomethyl ether, triphenylmethyl chloride, di(p-methoxyphenyl)phenylmethyl chloride, (methoxyphenyl) phenylmethyl chloride, trimethylchorosilane, triethylchlorosilane, triisopropylchlorosilane or tert-butyldimethylchlorosilane to afford Compound 3b or Compound 3a, respectively. In one embodiment, the protecting group is selected from C$_1$-C$_6$ alkoxycarbonyl, aryloxycarbonyl, acetyl, benzoyl, benzyl, pivaloyl, tetrahydropyranyl ether (THP), tetrahydrofuranyl, 2-methoxyethoxymethyl ether (MEM), methoxymethyl ether (MOM), ethoxyethyl ether (EE), p-methoxybenzyl ether (PMB), methylthiomethyl ether, triphenylmethyl (trityl, or Tr), dimethoxytrityl (DMT), methoxytrityl (MMT), and silyl ether. In one embodiment, the silyl ether is selected from trimethylsilyl ether (TMS), triethylsilyl ether (TES), triisopropylsilyl ether (TIPS), tert-butyldimethylsilyl ether (TBDMS), and tert-butyldiphenylsilyl ether (TBDPS). In one embodiment, the protecting group is benzoyl or acetyl.

In one embodiment, the conversion of Compound 3b to Compound 4b via intermediate 4b':

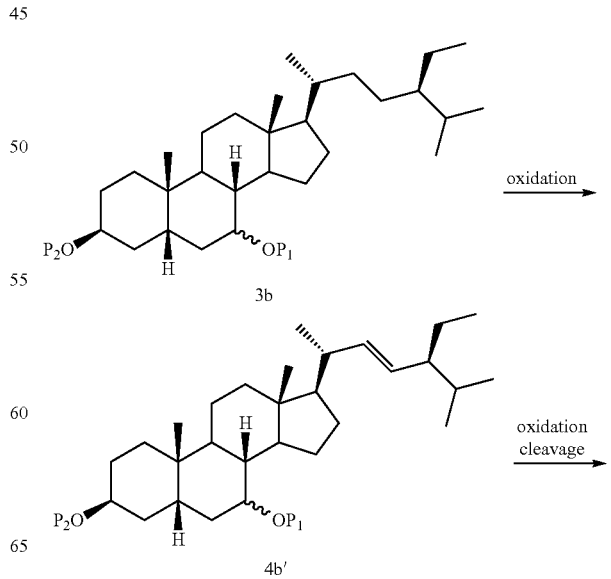

-continued

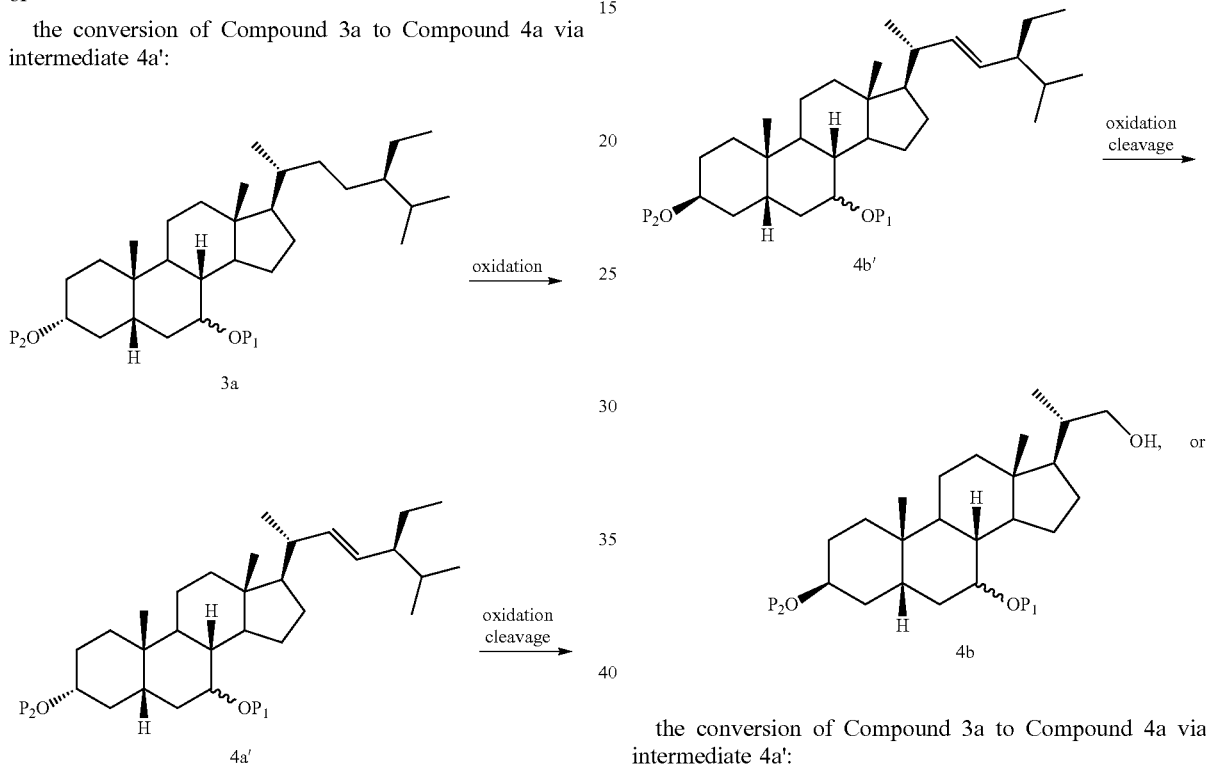

or the conversion of Compound 3a to Compound 4a via intermediate 4a':

is achieved by converting Compound 3b or Compound 3a under microbial conditions by using, for example, a microorganism to yield intermediate Compound 4b' or Compound 4a', which in turn is treated with $RuCl_3/NaIO_4$ or $OsO_4/NaIO_4$, followed by $NaBH_4$.

In one embodiment, the conversion of Compound 3b to Compound 4b via intermediate 4b':

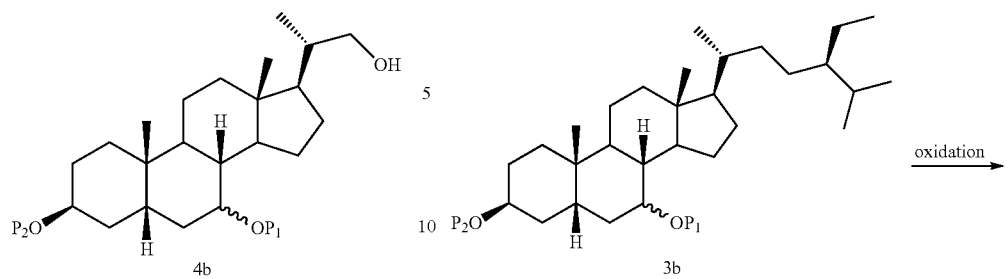

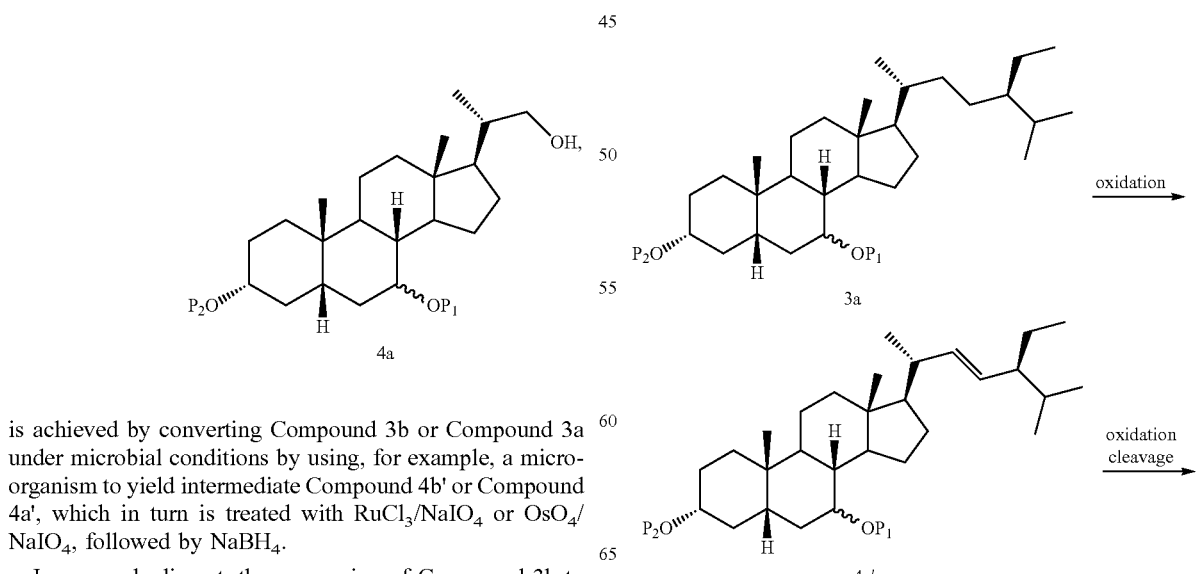

the conversion of Compound 3a to Compound 4a via intermediate 4a':

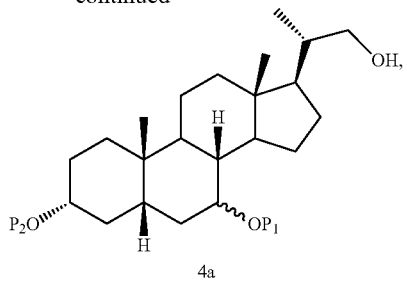

the oxidation of Compound 1 to Compound Xa:

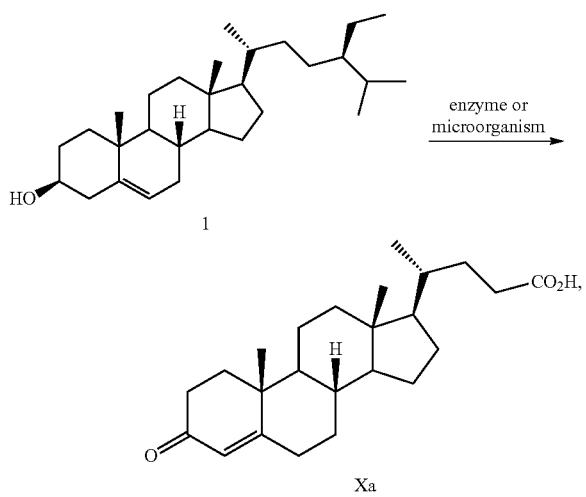

or
the oxidation of Compound 3b to Compound Ya:

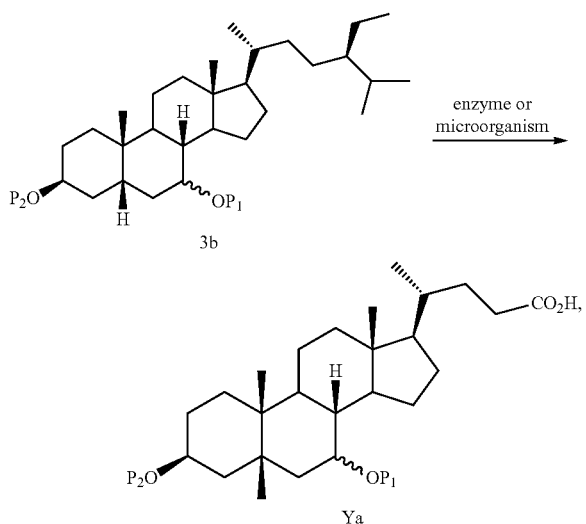

is achieved by first treating Compound 1, Compound Xa, Compound 3b or Compound 3a with a microorganism to form Compound Xa, Compound Xb, Compound 4b' or Compound 4a'. In one embodiment, the microorganism is selected from *Cephalosporium aphidicola, Cladosporium herbarum, Colletotrichum lini, Fusarium culmorum, F. moniliforme, F. oxysporum, Mucor piriformis, M. plumbeus, Rhizopus stolonifer, Botryodiplodia theobromae* IFO 6469, *Diplodia gossypina* ATCC 28570, DSM 62-678, DSM 62-679, *Botryosphaeria ribis* ATCC 22802, *Botryosphaeria berengeriana* ATCC 12557, and *Botryosphaeria rhodina* CBS 374.54, CBS 287.47 and CBS 306.58. In one embodiment, the microorganism is selected from the Pleosporaceae family (e.g., *Curvularia lunata* VKPM F-981, *Alternaria alternata*, or *Bipolaris sorokiniana* (*Helminthosporium*)), the Hypocreaceae family (e.g., *Fusarium* sp.), and the Mucoraceae family (e.g., *Rhizopus nigricans*), *Arthrobacter* sp. (e.g., *Arthrobacter polychromogene, Arthrobacter niigatensis, Arthrobacter defluvii*), *Rhodococcus* sp. (e.g., *Rhodococcus pyridinivorans, Rhodococcus erythropolis, Rhodococcus opacus, Rhodococcus ruber, Rhodococcus globerulus, Rhodococcus wratislaviensis*), *Pseudomonas* sp. (e.g., *Pseudomonas syringiae, Pseudomonas fluorescens*), *Lactobacillus* sp. (e.g., *Lactobacillus mesenter, Lactobacillus sake, Lactobacillus farciminis, Lactobacillus kefiri*), *Burkholderia* sp. (e.g., *Burkholderia pyrrocinia, Burkholderia xenovorans, Burkholderia multivorans*), *Xanthobacter* sp. (e.g., *Xanthobacter autotrophicus, Xanthobacter tagetidis*), *Fusarium* sp. (e.g., *Fusarium oxysporum*), Chlorophyceae (e.g., *Dunaliella minuta, Coccomyxa elongata, Trebouxia decolorans, Chlorella ellipsoidea, Chlorella saccharophila, Chlorella pringsheimii, Trebouxia* sp., *Dunaliella primolecta*), Prasinophyceae (e.g., *Tetraselmis tetrathele, Tetraselmis chui, Tetraselmis sueica, Pyramimonas gelidicola*), Cyanobacteria (e.g., *Anacystis nidulans, Fremyella diplosiphon, Cvanidium caldarium, Microcystis aeruginosa, Anabaena cylindrica, Spirulina platensis, Spirulina* sp., *Calothrix* sp., *Nostoc commune*), Chrysophyceae (e.g., *Ochromonas danica, Ochromonas malhamensis, Ochromonas sociabilis*), Xanthophyceae (e.g., *Botrydium granulatum, Monodus subterraneus, Tribonema aequale*), Euglenophyceae (e.g., *Euglena gracilis, Astasia longa*), Bangiophyceae (e.g., *Goniotrichum elegans, Porphyridium cruentum, Porphyridium aeurigeum*), Cryptophyceae (e.g., *Cryptomonas* sp., *Nematochrysopsis roscoffensis*), Raphidophyceae (*Fibrocapsa japonica*), *Chrysochromulina polylepis, Prymnesium patellifera, Ochrosphaera neapolitana, Ochrosphaera verrucosa, Pavlova lutheri, Pavlova lutheri, Emiliania huxleyi, Isochrysis galbana, Isochrysis galbana, Isochrysis* sp., *Isochrysis* sp., *Chrysotila lamellosa, Chrysotila lamellosa, Chrysotila stipitata, Hymenomomas carterae, Coccolithus pelagicus, Nitzschia longissima, Melosira granulats, Thalassionema nitzschoides, Nitzschia frustulum, Chaetoceros simplex, Skeletonema costatum, Thalassiosira fluviatilis, Fragilaria* sp., *Asterionella glacialis, Biddulphia sinensis, Ciclotella nana, Vavicula pelliculosa, Nitzschia closterium, Phaeodactylum tricornutum, Phaeodactylum tricornutum, Stauroneis amphioxys, Nitzschia ovalis, Biddulphia aurita, Chaetoceros* sp., *Thalassiosira pseudonana, Thalassiosira pseudonana, Amphora exigua, Amphora* sp., *Nitzschia alba, Rhizoselenium* spp., *Gonyaulax* spp., *Peridinium foliaceum, Peridinium foliaceum, Gonyaulax diegensis, Pyrocystis lunula, Gonyaulax polygramma, Gymnodinium wilczeki, Glenodinium hallii, Noctiluca milaris, Gymnodinium simplex*, and *Prorocentrum cordatum*. In one embodiment, Compound 4b' or Compound 4a' is treated with $RuCl_3/NaIO_4$ or $OsO_4/NaIO_4$, followed by $NaBH_4$, to form Compound 4b or Compound 4a.

In one embodiment, the conversion of Compound 4b to Compound 5b:

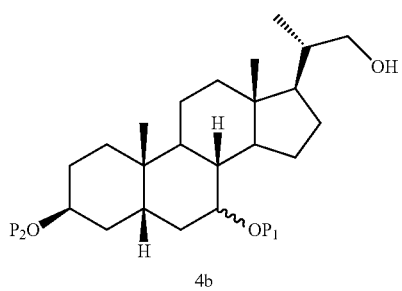

4b

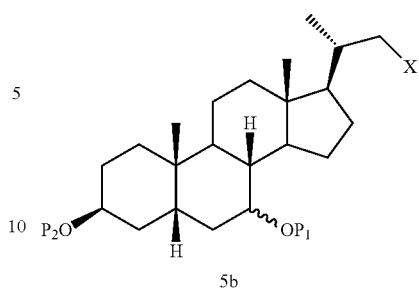

5b

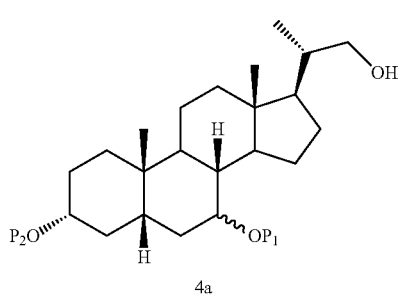

5b

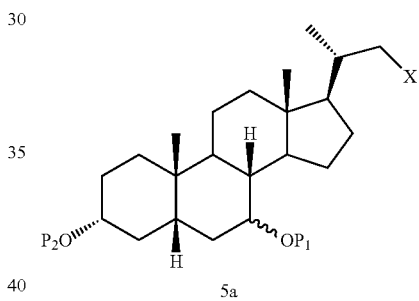

6b or the conversion of Compound 4a to Compound 5a:

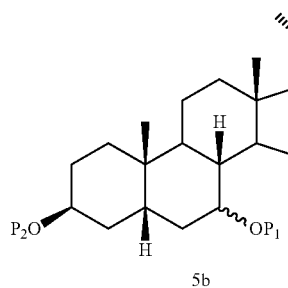

4a

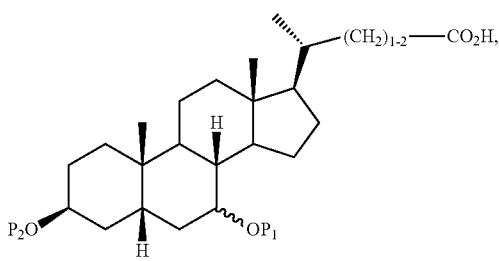

5a

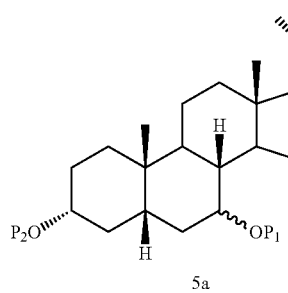

5a or the conversion of Compound 5a to Compound 6a:

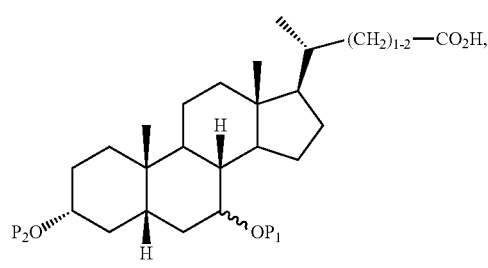

6a comprises treating Compound 4b or Compound 4a with a compound containing a leaving group X, wherein X is $SO_3Me$, $SO_3Ph$, $SO_3CF_3$, Cl, Br, or I. In one embodiment, the compound containing a leaving group is an alkyl halide (e.g., alkyl chloride, alkyl bromide, or alkyl iodide), a p-tolylsulfonate, or an alkylsulfonate. Compound 4a may be treated with $MeSO_2CL$, $PhSO_2CL$, $TolSO_2CL$, $CF_3SO_2Cl$ $SOCl_2$, or $SO_2Br_2$. Alternatively, Compound 4a may be treated with $(CF_3SO_2)_2O$, $POCl_3$ or $POBr_3$.

In one embodiment, the conversion of Compound 5b to Compound 6b:

comprises treating Compound 5b or Compound 5a with a malonate (e.g., dimethyl malonate, diethyl malonate, meldrum's acid, etc.) in the presence of a base to form a diester intermediate, and hydrolyzing the diester intermediate in the presence of an acid or base to form Compound 6b or Compound 6a.

In one embodiment, the conversion of Compound 5b to Compound 6b:

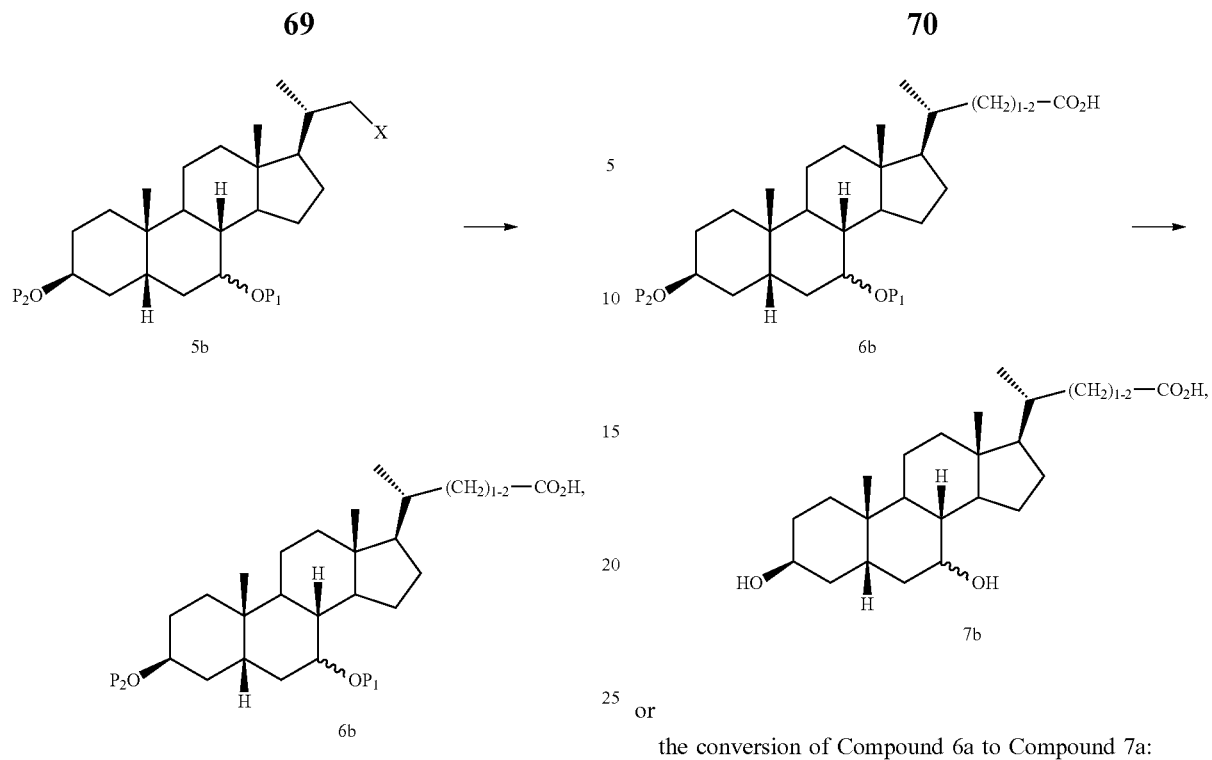

or the conversion of Compound 5a to Compound 6a:

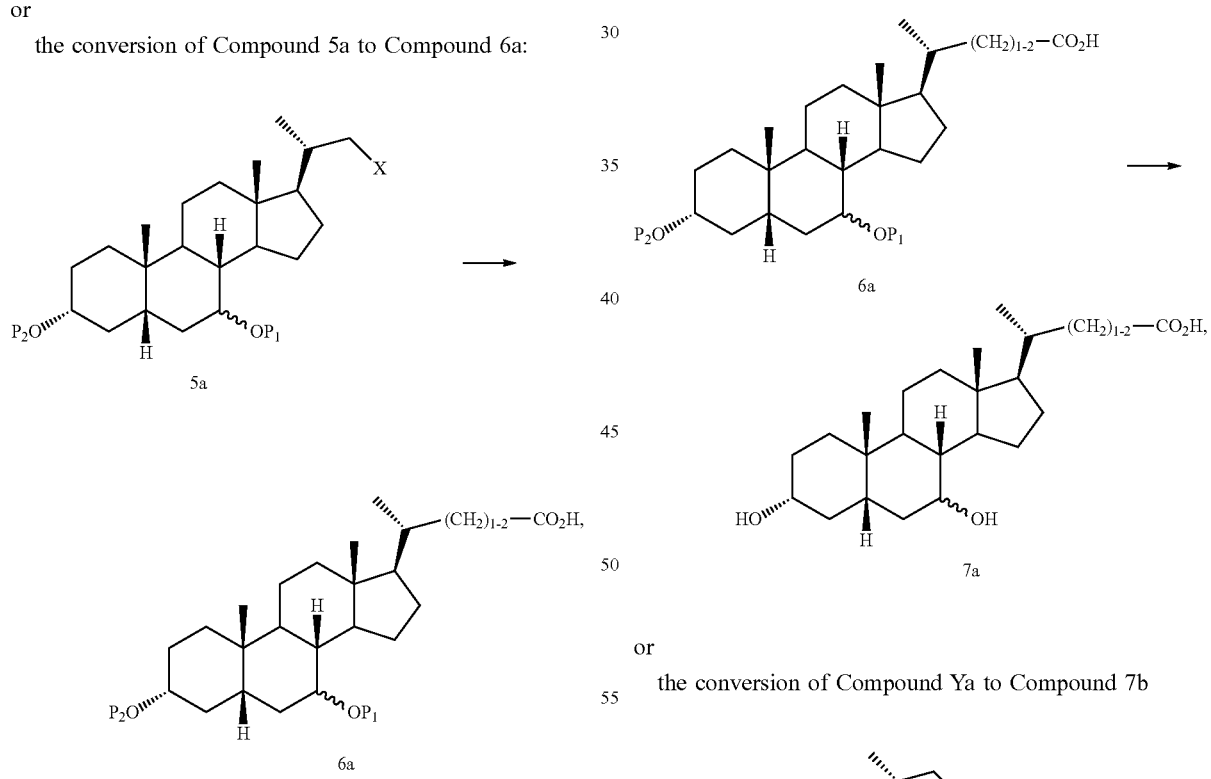

comprises treating Compound 5b or Compound 5a with a cyanide (e.g., NaCN, KCN, acetone cyanohydrin, TMSCN, etc.) to form a nitrile intermediate, and hydrolyzing the nitrile intermediate in the presence of a base (e.g., NaOH or KOH) to form Compound 6b or Compound 6a.

In one embodiment, the conversion of Compound 6b to Compound 7b:

the conversion of Compound 6a to Compound 7a:

or the conversion of Compound Ya to Compound 7b

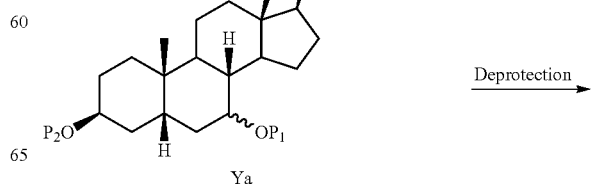

Deprotection

-continued

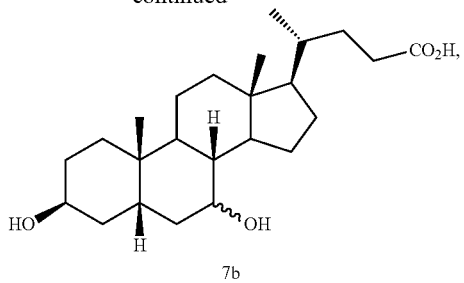

7b comprises deprotecting Compound 6b or Compound 6a to form Compound 7b or Compound 7a. In one embodiment, deprotection of the hydroxyl groups is conducted under an acid condition or a basic condition. In one embodiment, the deprotection is conducted using an acid, such as HCl or $H_2SO_4$. In one embodiment, the deprotection is conducted using a base, such as metal hydroxide (e.g., sodium hydroxide and potassium hydroxide) or carbonate (e.g., sodium carbonate). In one embodiment, the deprotection is conducted using TBAF or $NH_4F$.

In one embodiment, Compound 7b or Compound 7a can be oxidized through known methods to form Compound 8, which in turn, can be reduced through known methods (e.g., treatment with $NaBH_4$) to form Compound 9.

In one embodiment, Compound 9 can be oxidized through known methods to form Compound 10.

In one embodiment, Compound 10 can be alkylated through known methods to form a compound of the present application (e.g., obeticholic acid).

In one embodiment, a compound of Formula (Ib) is oxidized to a compound of Formula (IIa):

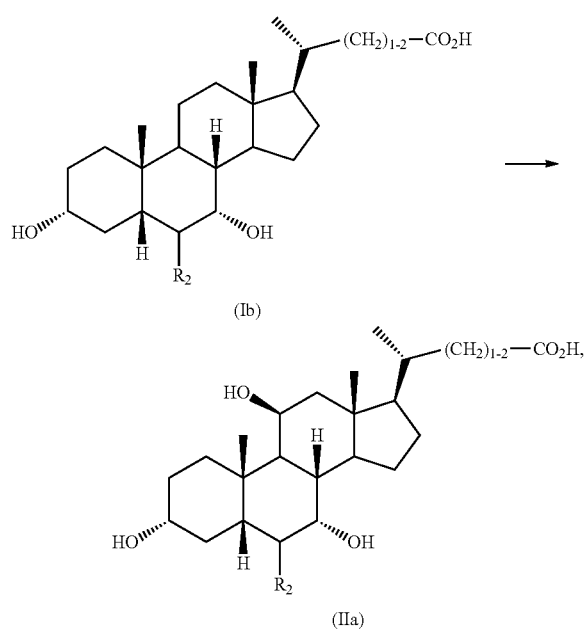

by treating a compound of Formula (Ib) with a 11-β-hydroxylase (e.g., CYP11B1). In one embodiment, the catalysis by a 11-β-hydroxylase is conducted by a natural or genetically modified microorganism (e.g., a bacterium, a fungus, an algae, a prokaryotic cell, an eukaryotic cell, an insect cell, or a mammalian cell (e.g., a human cell)) which expresses the 11-β-hydroxylase (e.g., CYP11B1).

In one embodiment, a compound of Formula (Ib) is oxidized to a compound of Formula (IIa):

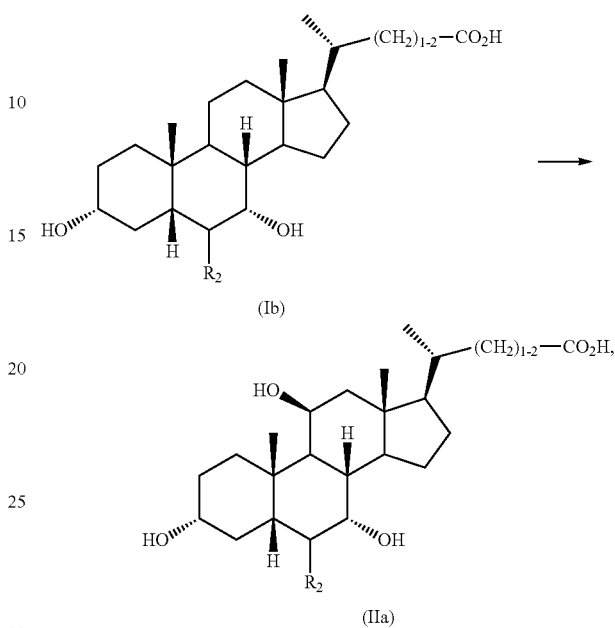

by treating a compound of Formula (Ib) with a microorganism which adds a 11-hydroxyl group. In one embodiment, the microorganism is selected from the group consisting of *Arthrobacter* sp. (e.g., *Arthrobacter polychromogene, Arthrobacter niigatensis, Arthrobacter defluvii*), *Rhodococcus* sp. (e.g., *Rhodococcus pyridinivorans, Rhodococcus erythropolis, Rhodococcus opacus, Rhodococcus ruber, Rhodococcus globerulus, Rhodococcus wratislaviensis*), *Pseudomonas* sp. (e.g., *Pseudomonas syringiae, Pseudomonas fluorescens*), *Lactobacillus* sp. (e.g., *Lactobacillus mesenter, Lactobacillus sake, Lactobacillus farciminis, Lactobacillus kefiri*), *Burkholderia* sp. (e.g., *Burkholderia pyrrocinia, Burkholderia xenovorans, Burkholderia multivorans*), *Xanthobacter* sp. (e.g., *Xanthobacter autotrophicus, Xanthobacter tagetidis*), *Fusarium* sp. (e.g., *Fusarium oxysporum*), *Absidia, Aspergillus, Cephalosporium, Chaetomella, Cunningamella, Curvularia, Diplodia, Dothideales, Epicoccum, Fusarium, Gibberella, Helminthosporium, Hypocreales, Mucor, Mucorales, Rhizopus, Saccharomyces, Spondylocladium, Chlorophyceae* (e.g., *Dunaliella minuta, Coccomyxa elongata, Trebouxia decolorans, Chlorella ellipsoidea, Chlorella saccharophila, Chlorella pringsheimii, Trebouxia* sp., *Dunaliella primolecta*), Prasinophyceae (e.g., *Tetraselmis tetrathele, Tetraselmis chui, Tetraselmis sueica, Pyramimonas gelidicola*), Cyanobacteria (e.g., *Anacystis nidulans, Fremyella diplosiphon, Cvanidium caldarium, Microcystis aeruginosa, Anabaena cylindrica, Spirulina platensis, Spirulina* sp., *Calothrix* sp., *Nostoc commune*), Chrysophyceae (e.g., *Ochromonas danica, Ochromonas malhamensis, Ochromonas sociabilis*), Xanthophyceae (e.g., *Botrydium granulatum, Monodus subterraneus, Tribonema aequale*), Euglenophyceae (e.g., *Euglena gracilis, Astasia longa*), Bangiophyceae (e.g., *Goniotrichum elegans, Porphyridium cruentum, Porphyridium aeurigeum*), Cryptophyceae (e.g., *Cryptomonas* sp., *Nematochrysopsis roscoffensis*), Raphidophyceae (*Fibro-* capsa japonica), *Chrysochromulina polylepis, Prymnesium patellifera, Ochrosphaera neapolitana, Ochrosphaera verrucosa, Pavlova lutheri, Pavlova lutheri, Emiliania huxleyi, Isochrysis galbana, Isochrysis galbana, Isochrysis* sp., *Isochrysis* sp., *Chrysotila lamellosa, Chrysotila lamellosa, Chrysotila stipitata, Hymenomomas carterae, Coccolithus pelagicus, Nitzschia longissima, Melosira granulats, Thalassionema nitzschoides, Nitzschia frustulum, Chaetoceros simplex, Skeletonema costatum, Thalassiosira fluviatilis, Fragilaria* sp., *Asterionella glacialis, Biddulphia sinensis, Ciclotella nana, Vavicula pelliculosa, Nitzschia closterium, Phaeodactylum tricornutum, Phaeodactylum tricornutum, Stauroneis amphioxys, Nitzschia ovalis, Biddulphia aurita, Chaetoceros* sp., *Thalassiosira pseudonana, Thalassiosira pseudonana, Amphora exigua, Amphora* sp., *Nitzschia alba, Rhizoselenium* spp., *Gonyaulax* spp., *Peridinium foliaceum, Peridinium foliaceum, Gonyaulax diegensis, Pyrocystis lunula, Gonyaulax polygramma, Gymnodinium wilczeki, Glenodinium hallii, Noctiluca milaris, Gymnodinium simplex,* and *Prorocentrum cordatum.* In one embodiment, the microorganism is selected from *Cephalosporium aphidicola, Cladosporium herbarum, Colletotrichum lini, Fusarium culmorum, F. moniliforme, F. oxysporum, Mucor piriformis, M. plumbeus, Rhizopus stolonifer, Botryodiplodia theobromae* IFO 6469, *Diplodia gossypina* ATCC 28570, DSM 62-678, DSM 62-679, *Botryosphaeria ribis* ATCC 22802, *Botryosphaeria berengeriana* ATCC 12557, and *Botryosphaeria rhodina* CBS 374.54, CBS 287.47 and CBS 306.58. In one embodiment, the microorganism is selected from the Pleosporaceae family (e.g., *Curvularia lunata* VKPM F-981, *Alternaria alternata*, or *Bipolaris sorokiniana* (*Helminthosporium*)), the Hypocreaceae family (e.g., *Fusarium* sp.), and the Mucoraceae family (e.g., *Rhizopus nigricans*).

In one embodiment, a compound of Formula (Ib) is oxidized to a compound of Formula (IIb):

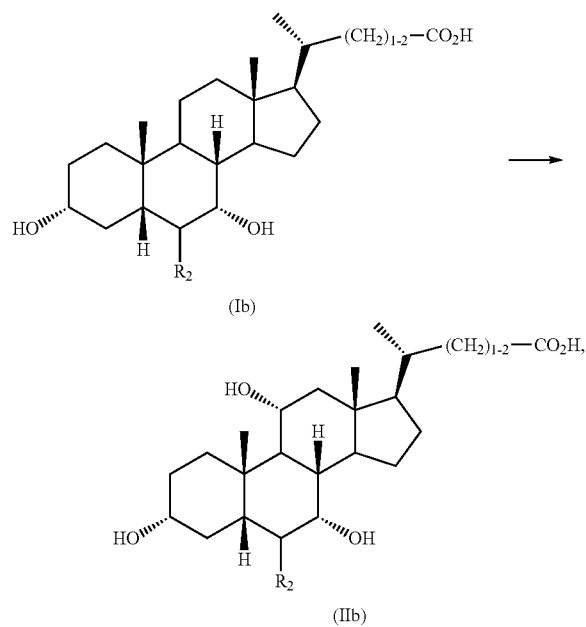

by treating a compound of Formula (Ib) with a microorganism which adds a 11-hydroxyl group. In one embodiment, the microorganism is selected from the group consisting of *Aspergillus ochraceus, Rhizopus nigricans,* or other organisms of the family Mucorales (e.g., *Rhizopus, Mucor,* and *Absidia*).

In one embodiment, the 11-α-hydroxyl in a compound of Formula (IIb) can be oxidized to an oxo group through known methods to form a compound of Formula (IIc).

In one embodiment, the 11-oxo group in a compound of Formula (IIc) can be reduced to 11-β-hydroxyl by treating the compound with a compound containing a hydride group (e.g., $NaBH_4$, $Na(OAc)_3BH$, L-Selectride, Red-Al, etc.).

In one embodiment, a compound of Formula (Ib) is oxidized to a compound of Formula (IIIb):

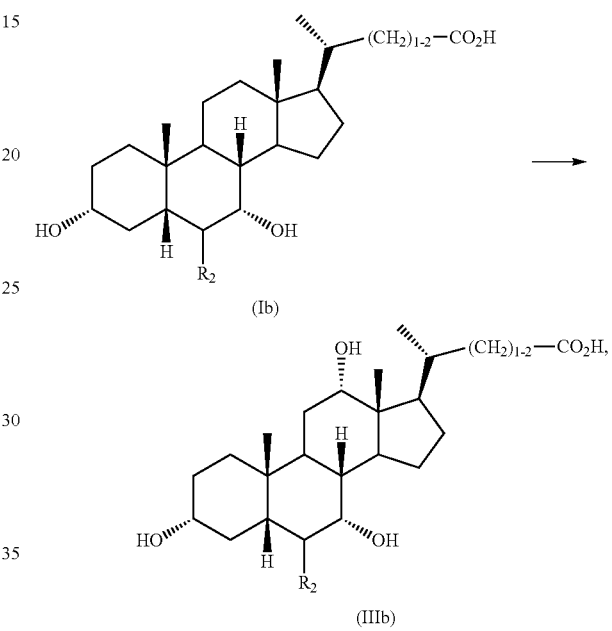

by treating a compound of Formula (Ib) with a thermophile such as *Geobacillus stearothermophilu* which adds a 12-hydroxyl group. See Afzal, et al., 2011, Biotechnology and Applied Biochemistry, 58, 250.

In one embodiment, the method of the present application produces a compound of Formula (A), or a pharmaceutically acceptable salt, solvate, or amino acid conjugate thereof, at least 50%, at least 55%, at least 60%, at least 65%, at least 70%, at least 75%, at least 80%, at least 85%, at least 90%, or at least 95% yield. In one embodiment, the method of the present application produces a compound of Formula (A) at least 65%, at least 70%, at least 75%, at least 80%, at least 85%, at least 90%, or at least 95% yield.

In one embodiment, the method of the present application produces a substantially pure compound of Formula (A), or a pharmaceutically acceptable salt, solvate, or amino acid conjugate thereof. The term "purity" as used herein refers to the amount of compound of Formula (A) based on analytic methods commonly used in the art (e.g., HPLC). Purity is based on the "organic" purity of the compound, and does not include a measure of any amount of water, solvent, metal, inorganic salt, etc. In one embodiment, the purity of the compound of Formula (A) is compared to the purity of the reference standard by comparing the area under the peak in HPLC. In one embodiment, the known standard for purity is a CDCA or related acid reference standard. In one embodiment, the compound of Formula (A) has a purity of greater than about 96%. In one embodiment, the compound of Formula (A) has a purity of greater than about 98%. For example, the purity of the synthesized compound of Formula (A) is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of Formula (A) is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of Formula (A) is 98.0%, 98.5%, 99.0%, 99.5%, 99.6%, 99.7%, 99.8%, or 99.9%. For example, the purity of the synthesized compound of Formula (A) is 98.5%, 99.0%, or 99.5%. In one embodiment, the purity is determined by HPLC.

The present application provides methods for the synthesis of highly pure compounds of Formula (A) which is safe and which produces compounds of Formula (A) on a large scale. In one embodiment, the method of the present application produces compounds of Formula (A) in high yield (>80%) and with limited impurities.

Oral Formulation and Administration

The present application provides compounds of Formula (A) for oral administration. In one embodiment, the formulation is oral administration for the prevention and treatment of FXR and/or TGR5 mediated diseases and conditions.

Formulations suitable for oral administration may be provided as discrete units, such as tablets, capsules, cachets (wafer capsule used by pharmacists for presenting a drug), lozenges, each containing a predetermined amount of one or more compounds of Formula (A); as powders or granules; as solutions or suspensions in aqueous or non-aqueous liquids; or as oil-in-water or water-in-oil emulsions.

Formulations of the present application may be prepared by any suitable method, typically by uniformly and intimately admixing one or more compounds of Formula (A) with liquids or finely divided solid carriers or both, in the required proportions and then, if necessary, shaping the resulting mixture into the desired shape.

For example a tablet may be prepared by compressing an intimate mixture comprising a powder or granules of one or more compounds of Formula (A) and one or more optional ingredients, such as a binder, lubricant, inert diluent, or surface active dispersing agent, or by molding an intimate mixture of powdered active ingredient and inert liquid diluent.

For example, one or more tablets may be administered to get to a target dose level based on the subject's weight, e.g., a human between about 30 kg to about 70 kg.

In addition to the ingredients specifically mentioned above, the oral formulations of the present application may include other agents known to those skilled in the art of pharmacy, having regard for the type of formulation in issue. Oral formulations suitable may include flavoring agents.

In one embodiment, the present application relates to a pharmaceutical formulation of one or more compounds of Formula (A), or a pharmaceutically acceptable salt, solvate, or amino acid conjugate thereof, wherein one or more compounds of Formula (A) is produced by a process of the application. In another embodiment, the formulation is administered orally.

In one embodiment, the formulation is in tablet form. In another embodiment, the formulation comprises one or more compounds of Formula (A) and one or more components selected from microcrystalline cellulose, sodium starch glycolate, magnesium stearate, coating material, or colloidal silicon dioxide. In one embodiment, the coating material is an Opadry® coating material.

All percentages and ratios used herein, unless otherwise indicated, are by weight. The percent dimeric impurity is on an area percent basis, typically as quantified by analytical HPLC.

Pharmaceutical Compositions

Compounds of Formula (A), or pharmaceutically acceptable salts, solvates, or amino acid conjugates thereof, are useful for a variety of medicinal purposes. Compounds of Formula (A) may be used in methods for the prevention or treatment of FXR and/or TGR5 mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesteremia, and hyperlipidemia. In one embodiment, the compounds of Formula (A) may be used in methods for lowering triglycerides and/or increasing HDL. Other effects of compounds of Formula (A) include lowering alkaline phosphatase (ALP), bilirubin, ALT, AST, and GGT. In one embodiment, the present application relates to a pharmaceutical composition comprising one or more compounds of Formula (A) and a pharmaceutically acceptable carrier, wherein the one or more compounds of Formula (A), or a pharmaceutically acceptable salt, solvate, or amino acid conjugate thereof, is produced by a method of the present application.

In one embodiment, the compound or pharmaceutical composition is administered orally, parenterally, or topically. In one embodiment, the compound or pharmaceutical composition is administered orally.

In one embodiment, the present application relates to a method for inhibiting fibrosis in a subject who is suffering from a cholestatic condition, the method comprising the step of administering to the subject an effective amount of one or more compounds of Formula (A) or a pharmaceutical composition thereof, wherein the one or more compounds of Formula (A) is produced by the method of the present application. In one embodiment, the present application relates to a method for inhibiting fibrosis in a subject who is not suffering from a cholestatic condition, the method comprising the step of administering to the subject an effective amount of one or more compounds of Formula (A) or a pharmaceutical composition thereof, wherein the one or more compounds of Formula (A) is produced by the method of the present application. In one embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In one embodiment, the subject has intestinal fibrosis associated with a disease selected from the group consisting of Crohn's disease, ulcerative colitis, post-radiation colitis, and microscopic colitis.

In one embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

Definitions

For convenience, certain terms used in the specification, examples and claims are collected here.

As used herein, "BA" means bile acid and bile acid derivatives. Bile acids are steroid carboxylic acids derived from cholesterol. The primary bile acids are cholic and chenodeoxycholic acids. In the body, these acids are conjugated with glycine or taurine before they are secreted into the bile.

"Alkyl" refers to saturated aliphatic groups, including straight chain alkyl groups (e.g., methyl, ethyl, propyl, butyl, pentyl, hexyl, heptyl, octyl, nonyl, decyl), branched chain alkyl groups (e.g., isopropyl, tert-butyl, isobutyl). In certain embodiments, a straight chain or branched chain alkyl has six or fewer carbon atoms in its backbone, referred to as "lower alkyl" (e.g., $C_1$-$C_6$ for straight chain meaning 1, 2, 3, 4, 5, or 6 carbon atoms, $C_3$-$C_6$ for branched chain meaning 3, 4, 5, or 6 carbon atoms). In some examples, a straight chain or branched chain alkyl has four or fewer carbon atoms in its backbone. In further examples, a straight chain or branched chain alkyl has three or fewer carbon atoms in its backbone. The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclopentyl, cyclohexyl, methylcyclohexyl, adamantyl, and norbornyl.

The term "substituted alkyl" refers to an alkyl moiety having a substituent replace one or more hydrogen atoms on at least one carbon of the hydrocarbon backbone. Such substituents can include, for example, halogen, hydroxyl, alkoxyl, alkylcarbonyl, alkoxycarbonyl, carboxylate, aminocarbonyl, alkylaminocarbonyl, dialkylaminocarbonyl, cyano, amino, nitro, and cyano.

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" or "alkoxyl" includes alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups.

The term "aryl" refers to a monocyclic, bicyclic, or tricyclic aromatic hydrocarbon ring system. Examples of aryl moieties include, but are not limited to, phenyl, naphthyl, and anthracenyl.

The term "ester" refers to moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "carbocyclic ring" refers to a saturated cyclic, partially saturated cyclic, or aromatic ring containing from 3 to 14 carbon ring atoms ("ring atoms" are the atoms bound together to form the ring). A carbocyclic ring typically contains from 3 to 10 carbon ring atoms. Examples include cyclopropyl, cyclobutyl, cyclopentyl, cyclopentenyl, cyclopentadienyl, cyclohexyl, cyclohexenyl, cyclohexadienyl, and phenyl. A "carbocyclic ring system" alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluorenyl, and decalinyl.

The term "heterocyclic ring" or "heterocycle" refers to a saturated cyclic, partially saturated cyclic, or aromatic ring containing from 3 to 14 ring atoms ("ring atoms" are the atoms bound together to form the ring), in which at least one of the ring atoms is a heteroatom that is oxygen, nitrogen, or sulfur, with the remaining ring atoms being independently selected from the group consisting of carbon, oxygen, nitrogen, and sulfur. Examples of heterocyclyl include, but are not limited to, tetrahydrofuranyl, tetrahydropyranyl, piperidinyl, morpholino, pyrrolinyl, pyrimidinyl, and pyrrolidinyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively). Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. The term "heteroaryl" also includes pyridyl N-oxides and groups containing a pyridine N-oxide ring.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "oxo" refers to an oxygen atom, which forms a carbonyl when attached to carbon, an N-oxide when attached to nitrogen, and a sulfoxide or sulfone when attached to sulfur.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As defined herein, the term "derivative", e.g., in the term "bile acid derivatives", refers to compounds that have a common core 4-membered ring structure, and are substituted with various groups as described herein.

As defined herein, the term "metabolite", e.g., in the term "bile acid metabolites", refers to glucuronidated and sulphated derivatives of the compounds described herein, wherein one or more glucuronic acid or sulphate moieties are linked to the bile acid compounds described herein. Glucuronic acid moieties may be linked to the bile acid compounds through glycosidic bonds with the hydroxyl groups of the bile acid compounds (e.g., 3-hydroxyl, 7-hydroxyl, 12-hydroxyl, and/or 15-hydroxyl). Sulphated derivatives of the bile acid compounds may be formed through sulfation of the hydroxyl groups (e.g., 3-hydroxyl, 7-hydroxyl, 12-hydroxyl, and/or 15-hydroxyl). Examples of bile acid metabolites include, but are not limited to, 3-O-glucuronide, 7-O-glucuronide, 12-O-glucuronide, 15-O-glucuronide, 3-O-7-O-glucuronide, 3-O-12-O-glucuronide, 3-O-15-O-glucuronide, 7-O-12-0-glucuronide, 7-O-15-O-glucuronide, 12-O-15-O-glucuronide, 3-O-7-O-12-O-glucuronide, 3-O-7-O-15-O-glucuronide, and 7-O-12-O-15-O-glucuronide, of the bile acid compounds described herein, and 3-sulphate, 7-sulphate, 12-sulphate, 15-sulphate, 3,7-bisulphate, 3,12-bisulphate, 3,15-bisulphate, 7,12-bisulphate, 7,15-bisulphate, 3,7,12-trisulphate, 3,7,15-trisulphate, 7,12,15-trisulphate, of the bile acid compounds described herein.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, *Chem. Rev.* 96, 3147-3176 (1996).

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

As used herein, the term "about" or "approximately", or the like, when used together with a numeric value, may include a range of numeric values which is more or less than the numeric value to which the term refers or relate. For example, the range can include numeric values that are from 10% less to 10% more, from 9% less to 9% more, from 8% less to 8% more, from 7% less to 7% more, from 6% less to 6% more, from 5% less to 5% more, from 4% less to 4% more, from 3% less to 3% more, from 2% less to 2% more, or from 1% less to 1% more, than the numeric value to which the term refers or relate. For example, "about 5" can include numeric values from 4.5 to 5.5, from 4.55 to 5.45, from 4.6 to 5.4, from 4.65 to 5.35, from 4.7 to 5.3, from 4.75 to 5.25, from 4.8 to 5.2, from 4.85 to 5.15, from 4.9 to 5.1, or from 4.95 to 5.05.

The term "effective amount" as used herein refers to an amount of one or more compounds of Formula (A) (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of one or more compounds of Formula (A) that, when administered to a mammal for treating a disease, is sufficient to effect such treatment for the disease. The "therapeutically effective amount" will vary depending on the disease and its severity and the age, weight, etc., of the mammal to be treated.

A therapeutically effective amount of a compound of Formula (A) can be formulated with a pharmaceutically acceptable carrier for administration to a human or an animal. Accordingly, the compounds of Formula (A) or their formulations can be administered, for example, via oral, parenteral, or topical routes, to provide an effective amount of the compound. In alternative embodiments, the compounds of Formula (A) are prepared in accordance with the present application can be used to coat or impregnate a medical device, e.g., a stent.

The application also comprehends isotopically-labeled compounds of Formula (A), or pharmaceutically acceptable salts, solvates, or amino acid conjugates thereof, which are identical to those recited in formulae of the application and following, but for the fact that one or more atoms are replaced by an atom having an atomic mass or mass number different from the atomic mass or mass number most commonly found in nature. Examples of isotopes that can be incorporated into compounds of Formula (A), or pharmaceutically acceptable salts, solvate, or amino acid conjugates thereof include isotopes of hydrogen, carbon, nitrogen, fluorine, such as $^3$H, $^{11}$C, $^{14}$C and $^{18}$F.

Tritiated, i.e., $^3$H, and carbon-14, i.e., $^{14}$C, isotopes are particularly may be used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances, isotopically labeled compounds of Formula (A), or pharmaceutically acceptable salts, solvates, or amino acid conjugates thereof can generally be prepared by carrying out the procedures disclosed in the Schemes and/or in the Examples of the application, by substituting a readily available isotopically labeled reagent for a non-isotopically labeled reagent. In one embodiment, compounds of Formula (A), or pharmaceutically acceptable salts, solvates, or amino acid conjugates thereof are not isotopically labelled. In one embodiment, deuterated compounds of Formula (A) are useful for bioanalytical assays. In another embodiment, compounds of Formula (A), or pharmaceutically acceptable salts, solvates, or amino acid conjugates thereof are radiolabelled.

"Solvates" means solvent addition forms that contain either stoichiometric or non-stoichiometric amounts of solvent. Compounds of Formula (A) may have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate. Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable salts" refer to derivatives of the compounds of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The pharmaceutically acceptable salts of the present application can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, page 1445 (1990).

As used herein, the term "metabolite", e.g., in the term "bile acid metabolites", refers to glucuronidated and sulphated derivatives of the compounds described herein, wherein one or more glucuronic acid or sulphate moieties are linked to the bile acid compounds described herein. Glucuronic acid moieties may be linked to the bile acid compounds through glycosidic bonds with the hydroxyl groups of the bile acid compounds (e.g., 3-hydroxyl and/or 7-hydroxyl). Sulphated derivatives of the bile acid compounds may be formed through sulfation of the hydroxyl groups (e.g., 3-hydroxy and/or, 7-hydroxyl, 12-hydroxyl, and/or 15-hydroxyl). Examples of bile acid metabolites include, but are not limited to, 3-O-glucuronide, 7-O-glucuronide, 3-O-7-O-glucuronide, of the bile acid compounds described herein, and 3-sulphate, 7-sulphate and 3,7-bisulphate, of the bile acid compounds described herein.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present application, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers" or "diastereomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

As used herein, the term "amino acid conjugates" refers to conjugates of the compounds of the application with any suitable amino acid. Taurine ($NH(CH_2)_2SO_3H$), glycine ($NHCH_2CO_2H$), and sarcosine ($N(CH_3)CH_2CO_2H$) are examples of amino acid conjugates. Suitable amino acid conjugates of the compounds have the added advantage of enhanced integrity in bile or intestinal fluids. Suitable amino acids are not limited to taurine, glycine, and sarcosine. The application encompasses amino acid conjugates of the compounds of the application.

A "pharmaceutical composition" is a formulation containing one or more compounds of Formula (A) in a form suitable for administration to a subject. In one embodiment, the pharmaceutical composition is in bulk or in unit dosage form. It is can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the application are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity of one or more compounds of Formula (A) obeticholic acid (e.g., a formulation of CDCA, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, compounds of Formula (A) are mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is human child (e.g., between about 30 kg to about 70 kg). In one embodiment, the human child has had a Kasai procedure, where the Kasai procedure effectively gives them a functional bile duct when they are born either without a bile duct or one that is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" of a compound means a salt that is pharmaceutically acceptable and that possesses the desired pharmacological activity of the parent compound.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

While it is possible to administer compounds of the application directly without any formulation, compounds of Formula (A) are usually administered in the form of pharmaceutical formulations comprising a pharmaceutically acceptable excipient and one or more compounds of Formula (I). These formulations can be administered by a variety of routes including oral, buccal, rectal, intranasal, transdermal, subcutaneous, intravenous, intramuscular, and intranasal.

In one embodiment, compounds of Formula (A) can be administered transdermally. In order to administer transdermally, a transdermal delivery device ("patch") is needed. Such transdermal patches may be used to provide continuous or discontinuous infusion of a compound of the present application in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this application belongs. In the case of conflict, the present specification will control.

EXAMPLES

The following examples are intended to illustrate certain embodiments of the present invention, but do not exemplify the full scope of the invention.

Example 1: Synthesis of CDCA from β-Sitosterol

Synthesis of Compound Ia from β-Sitosterol

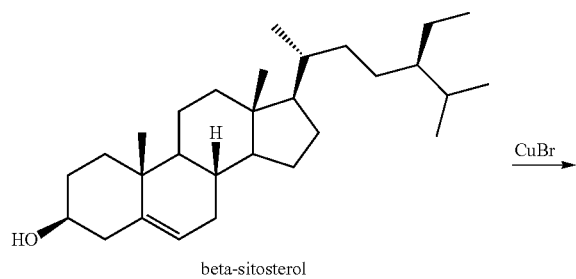

A solution of β-sitosterol in acetonitrile is contacted with CuBr and t-BuOOH and heated to reflux. The mixture is then contacted with $Na_2SO_3$ (10% aqueous solution) and extracted with tert-butyl methyl ether. The extracts are combined and washed with $NaHCO_3$ (10% aqueous solution), dried over $Na_2SO_4$ and evaporated to afford Compound Ia.

Synthesis of Compound 2b from Compound Ia

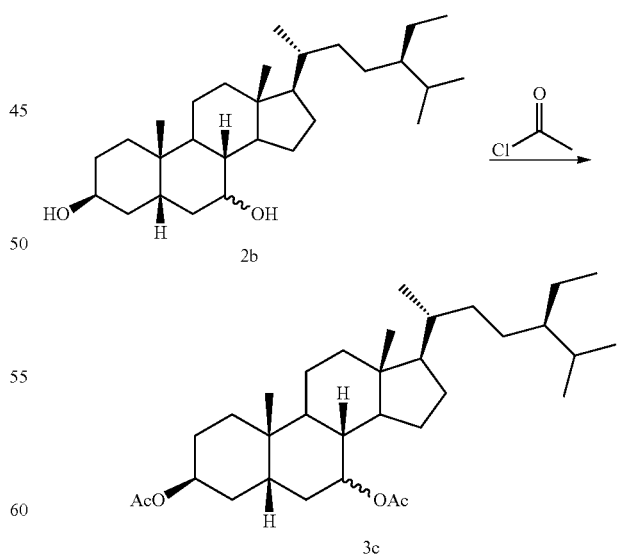

The reduction of the C5-C6 olefin of Compound Ia to afford Compound 2b is conducted via hydrogenation. A solution of Compound Ia in a mixture of EtOH and AcOH is contacted with Pd/C catalyst and pressurized with hydrogen up to 100 psi with heating. The mixture is filtered through Celite, diluted with water and extracted with tert-butyl methyl ether. The extracts are combined and washed with $NaHCO_3$ (10% aqueous solution), dried over $Na_2SO_4$ and evaporated to afford Compound 2b.

Synthesis of Compound 3c from Compound 2b

A solution of Compound 2b in $CH_2Cl_2$ is treated with trimethylamine followed by acetyl chloride. The mixture is diluted with water and the organic layer is separated and washed with dilute aqueous HCl. The organic layer is dried over Na$_2$SO$_4$ and evaporated to afford Compound 3c in which the two hydroxyl groups are protected.

Synthesis of Compound 4c' from Compound 3c

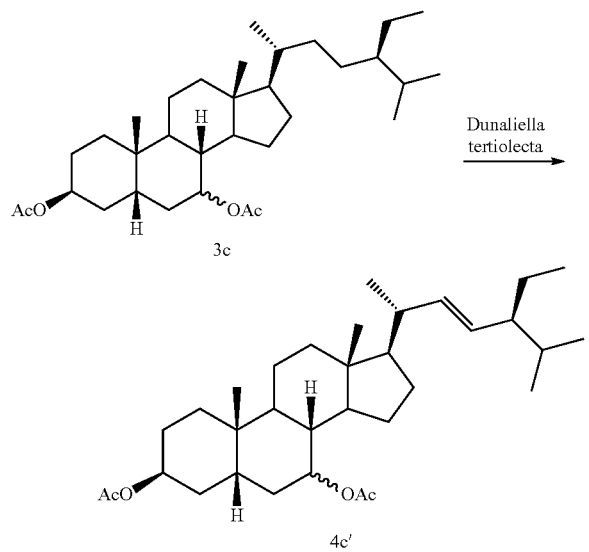

Dunaliella tertiolecta cells are grown photoautotrophically in three folded f/2 medium except vitamin solution at 21° C. and irradiated with fluorescent lamps at 50 µE/m$^2$s. A constant nitrate concentration is maintained by supplying NO$_3$ stock solution after measuring the NO$_3$ concentration. Dunaliella tertiolecta cultures are set up in bubble-column photoreactors. Compound 3c is contacted with the cells in an aqueous solution. Purification by centrifugation and chromatography is used to afford Compound 4c'.

Synthesis of Compound 4a1 from Compound 4c'

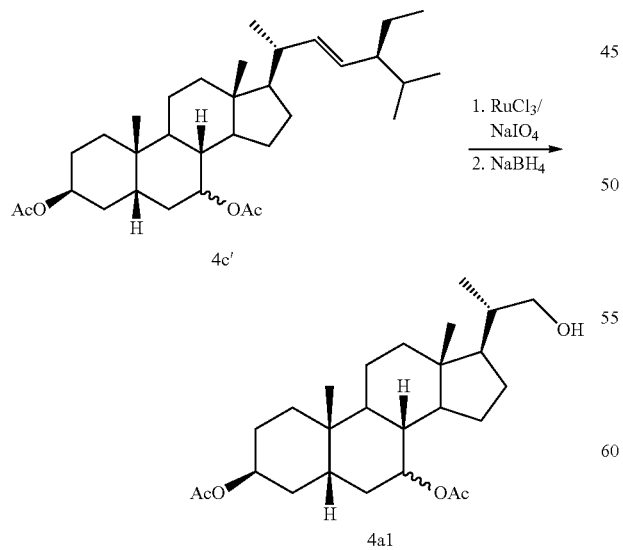

A solution of Compound 4c' in chloroform is contacted with RuCl$_3$ and NaIO$_4$ (aqueous solution). The mixture is filtered through Celite and the organic layer is separated and washed with Na$_2$SO$_3$ (10% aqueous solution). The organic layer is then contacted with NaBH$_4$ (aqueous solution) followed by addition of dilute aqueous HCl. The organic layer is washed with NaHCO$_3$ (10% aqueous solution), dried over Na$_2$SO$_4$ and evaporated to afford Compound 4a1.

Synthesis of Compound 5c from Compound 4a1

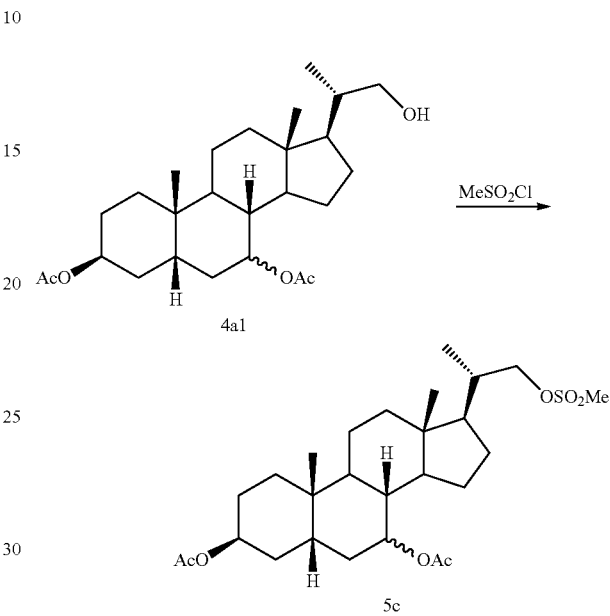

A solution of Compound 4a1 and trimethylamine is contacted with MeSO$_2$Cl. The reaction mixture is quenched with water and the organic layer is separated. The organic layer is washed with NaHCO$_3$ (10% aqueous solution), dried over Na$_2$SO$_4$ and evaporated to afford Compound 5c.

Synthesis of Compound 7c from Compound 5c

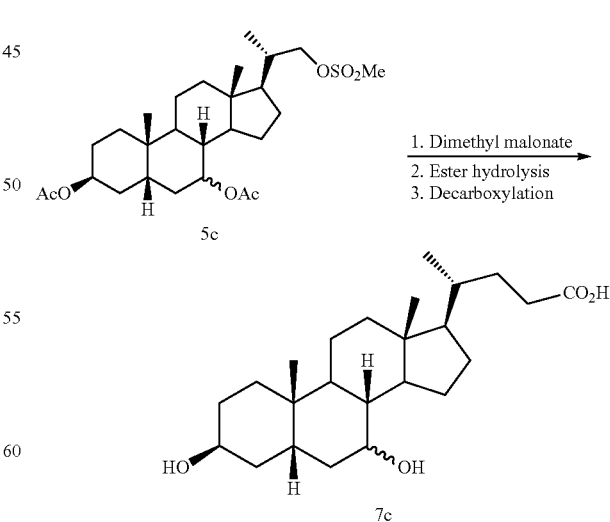

A solution of Compound 5c in DMF is contacted with a DMF solution of dimethyl malonate sodium salt. The mixture is quenched with water and extracted with ethyl acetate.

The extract is evaporated and the residue is diluted with isopropanol and contacted with KOH. After heating, the mixture is concentrated, diluted with xylenes and acidified with dilute aqueous HCl. The organic layer is contacted with pyridine and the mixture is heated to reflux. After cooling the organic layer is washed with dilute aqueous HCl, then washed with water. The organic layer is concentrated to afford Compound 7c.

Synthesis of Compound 8a from Compound 7c

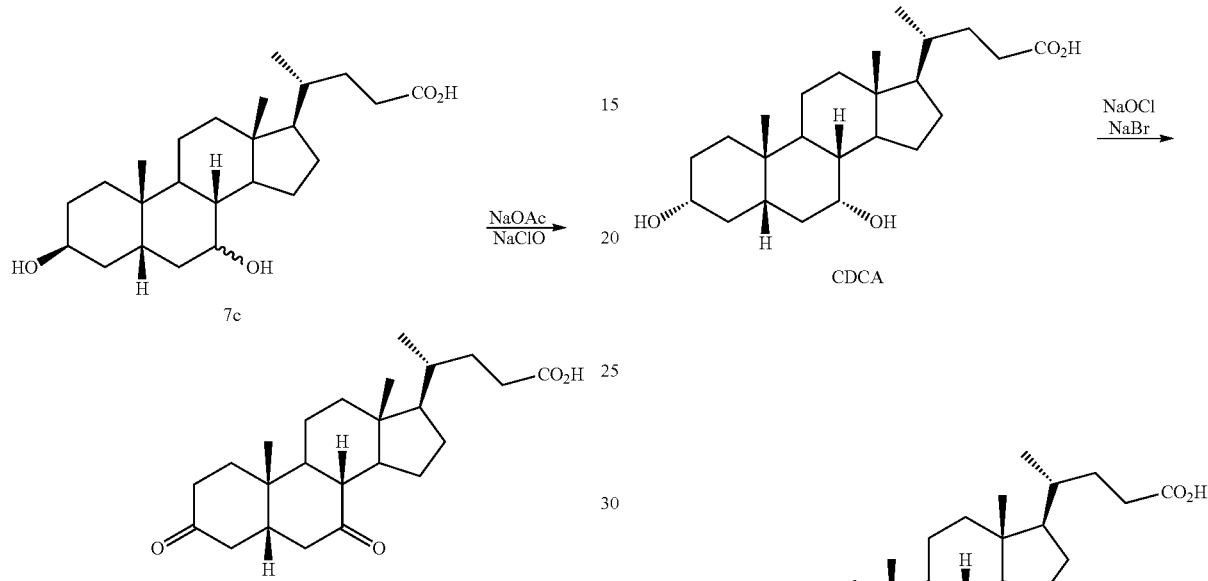

A solution of Compound 7c in acetic acid is contacted with an aqueous solution of sodium acetate and sodium hypochlorite. The mixture is diluted with water and the resulting solids are filtered to afford Compound 8a.

Synthesis of CDCA from Compound 8a

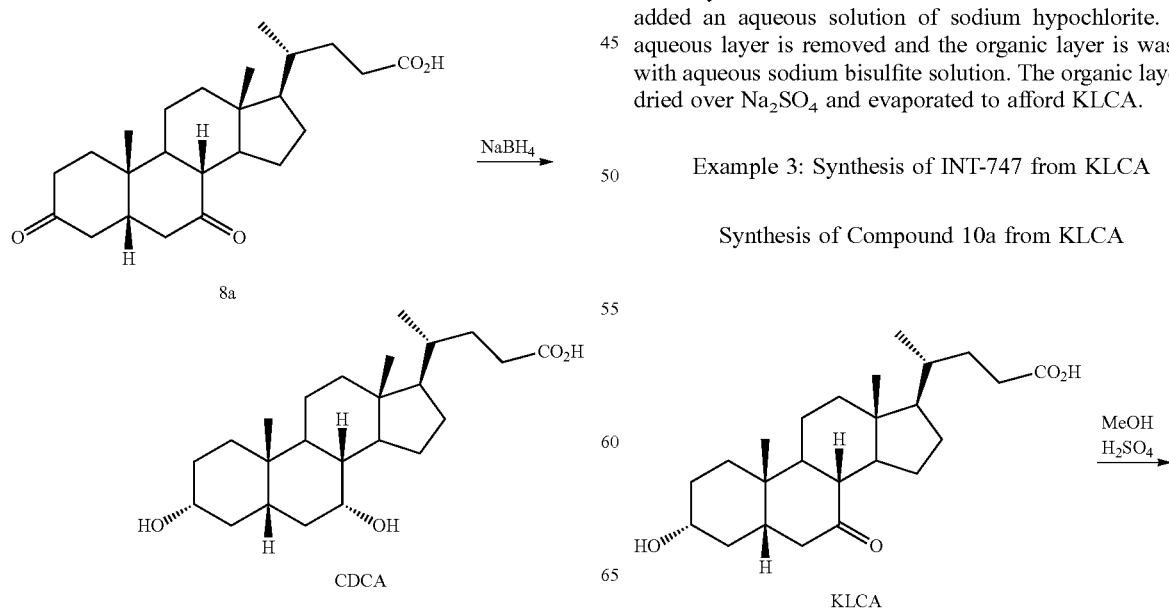

A solution of Compound 8a in aqueous sodium hydroxide is contacted with sodium borohydride at elevated temperature. The solution is treated with aqueous HCl and extracted with ethyl acetate. The organic layer is separated and concentrated to afford CDCA.

Example 2: Synthesis of KLCA from CDCA

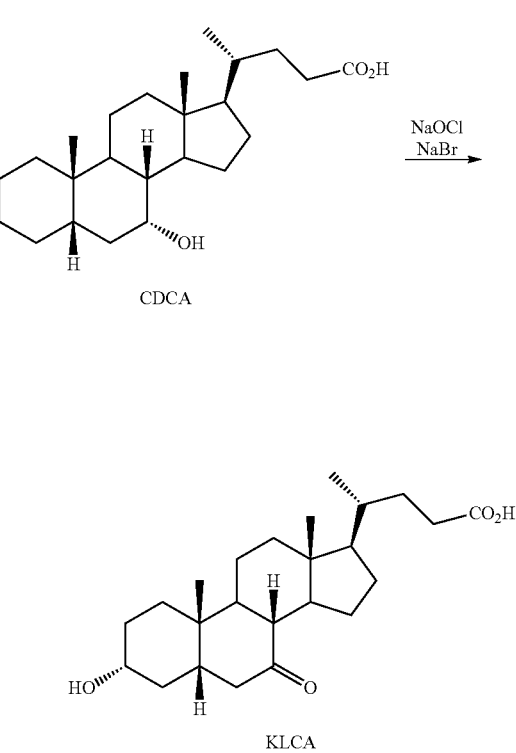

A solution of CDCA in ethyl acetate, acetic acid and methanol is contacted with an aqueous solution of NaBr and tetrabutylammonium bromide. To the well stirred solution is added an aqueous solution of sodium hypochlorite. The aqueous layer is removed and the organic layer is washed with aqueous sodium bisulfite solution. The organic layer is dried over $Na_2SO_4$ and evaporated to afford KLCA.

Example 3: Synthesis of INT-747 from KLCA

Synthesis of Compound 10a from KLCA

Synthesis of Compound 13a from Compound 12a

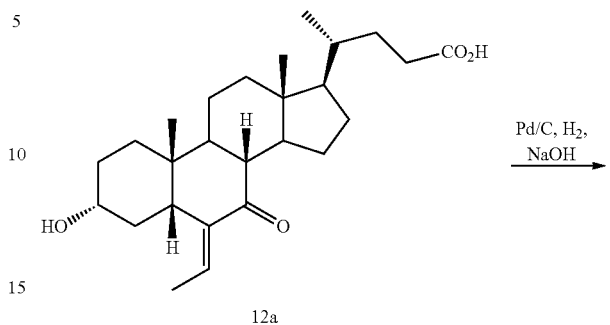

A solution of KLCA in methanol is contacted with conc. $H_2SO_4$ and heated to reflux. The solution is cooled and diluted with water to initiate crystallization. The solids are filtered and washed with a mixture of methanol and water to afford Compound 10a.

Synthesis of Compound 12a from Compound 10a

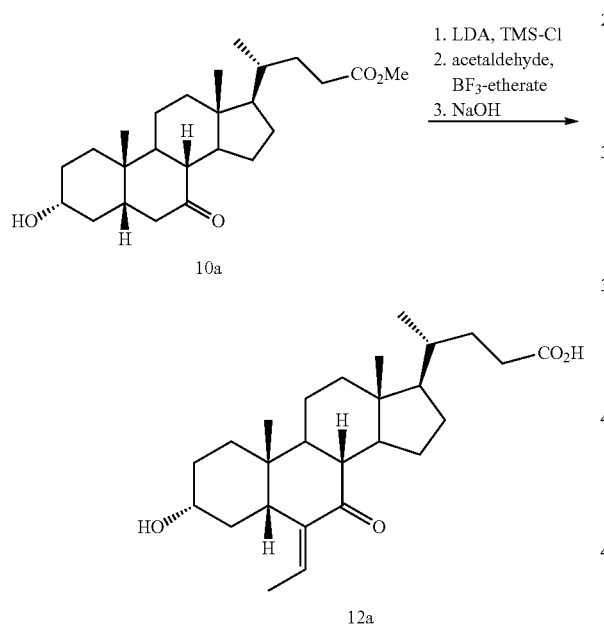

A solution of Compound 10a in dry THF in the presence of chlorotrimethylsilane is contacted with a solution of LDA at below −15° C. The mixture is quenched with aqueous citric acid solution and the organic layer is separated and concentrated to an oil. The oil is dissolved in dry dichloromethane and admixed with acetaldehyde, which is then added to a pre-cooled solution of $BF_3$-$OEt_2$ while maintaining an internal temperature of <−60° C. The mixture is warmed to ambient temperature and quenched with dilute aqueous NaOH solution. The organic layer is concentrated to an oil, diluted with methanol and contacted with an aqueous NaOH solution. The mixture is diluted with toluene and the aqueous layer is removed and acidified with citric acid in the presence of ethyl acetate. The organic layer is removed and partially evaporated to induce crystallization. The suspension is filtered and washed with ethyl acetate to afford Compound 12a.

A solution of Compound 12a in aqueous NaOH is contacted with palladium on carbon and pressurized with 2-5 bar hydrogen pressure. The mixture is vigorously stirred and heated to 95-100° C. until hydrogen uptake stops. The mixture is filtered through Celite and the aqueous layer is contacted with dilute aqueous HCl in the presence of n-butyl acetate. The organic layer is separated and partially evaporated to induce crystallization. The suspension is filtered and the solids are washed with n-butyl acetate to afford Compound 13a.

Synthesis of INT-747 from Compound 13a

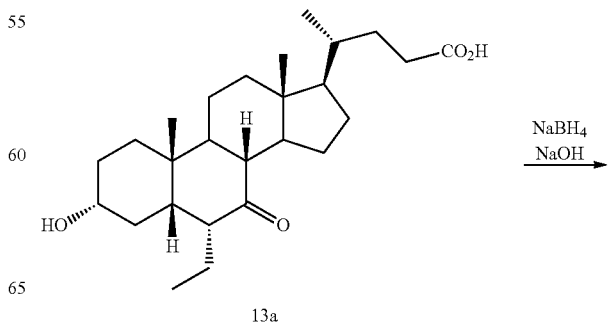

-continued

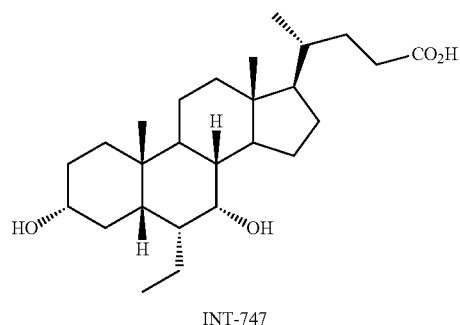

INT-747

A solution of Compound 13a in aqueous NaOH is heated to 90° C. and contacted with sodium borohydride. The mixture is cooled and quenched with an aqueous citric acid solution in the presence of n-butyl acetate. The organic layer is separated and partially evaporated to induce crystallization. The suspension is filtered and the solids are washed with n-butyl acetate to afford INT-747.

Example 4: Synthesis of 6α-ethyl-3α, 7α-23-trihydroxy-24-nor-5β-cholan-23-sulfate from Compound 7d Synthesis of Compound 10c from Compound 7d

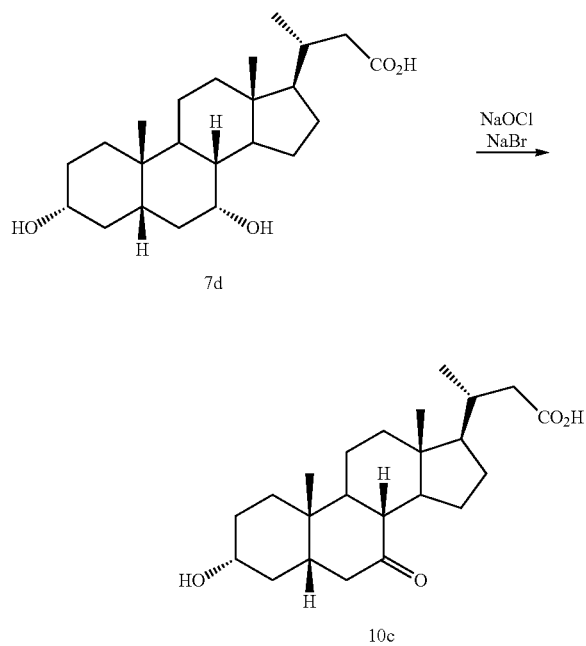

A solution of Compound 7d in ethyl acetate, acetic acid and methanol is contacted with an aqueous solution of NaBr and tetrabutylammonium bromide. To the well stirred solution is added an aqueous solution of sodium hypochlorite. The aqueous layer is removed and the organic layer is washed with aqueous sodium bisulfate solution. The organic layer is dried over $Na_2SO_4$ and evaporated to afford Compound 10c.

Synthesis of Compound 10d from Compound 10c

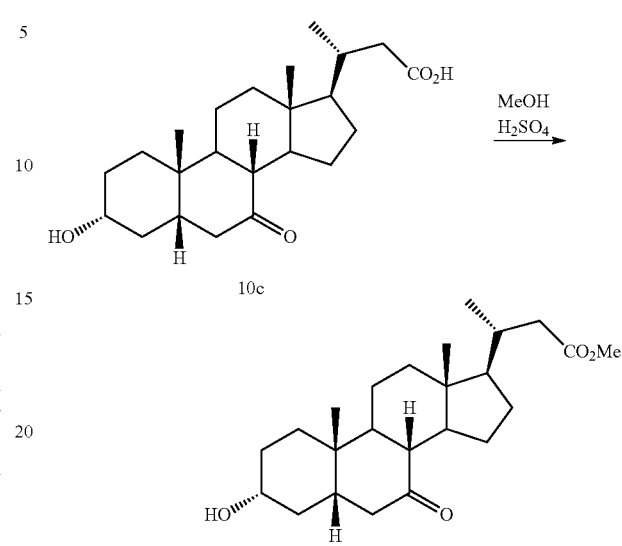

A solution of Compound 10c in methanol is contacted with conc. $H_2SO_4$ and heated to reflux. The solution is cooled and diluted with water to initiate crystallization. The solids are filtered and washed with a mixture of methanol and water to afford Compound 10d.

Synthesis of Compound 12b from Compound 10d

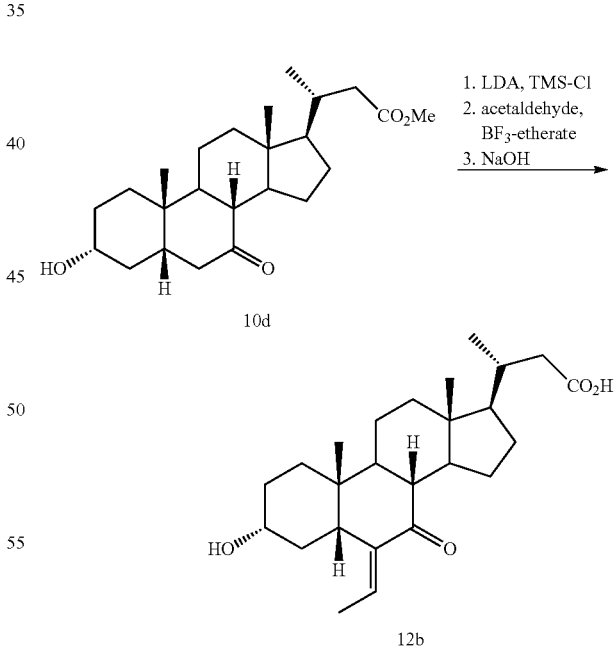

A solution of Compound 10d in dry THF in the presence of chlorotrimethylsilane is contacted with a solution of LDA at below −15° C. The mixture is quenched with aqueous citric acid solution and the organic layer is separated and concentrated to an oil. The oil is dissolved in dry dichloromethane and admixed with acetaldehyde, which is then added to a pre-cooled solution of $BF_3$-$OEt_2$ while maintaining an internal temperature of <−60° C. The mixture is warmed to ambient temperature and quenched with dilute aqueous NaOH solution. The organic layer is concentrated to an oil, diluted with methanol and contacted with an aqueous NaOH solution. The mixture is diluted with toluene and the aqueous layer is removed and acidified with citric acid in the presence of ethyl acetate. The organic layer is removed and partially evaporated to induce crystallization. The suspension is filtered and washed with ethyl acetate to afford Compound 12b.

Synthesis of Compound 13c from Compound 12b

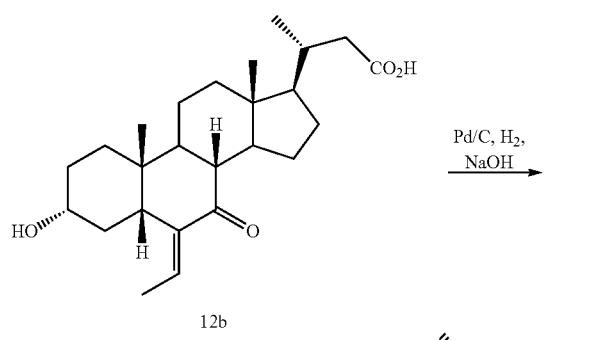

A solution of Compound 12b in aqueous NaOH is contacted with palladium on carbon and pressurized with 2-5 bar hydrogen pressure. The mixture is vigorously stirred and heated to 95-100° C. until hydrogen uptake stops. The mixture is filtered through Celite and the aqueous layer is contacted with dilute aqueous HCl in the presence of n-butyl acetate. The organic layer is separated and partially evaporated to induce crystallization. The suspension is filtered and the solids are washed with n-butyl acetate to afford Compound 13c.

Synthesis of Compound 14a from Compound 13c

A solution of Compound 13c in dichloromethane is contacted with acetic anhydride in the presence pyridine. The mixture is quenched with water and the organic layer is removed and washed with an aqueous sodium bicarbonate solution. The organic layer is separated and evaporated. The residue is dissolved in dry THF and contacted with ethyl chloroformate in the presence of trimethylamine, followed by NaBH$_4$. The mixture is diluted with dichloromethane and quenched with aqueous HCl. The organic layer is separated and concentrated to afford Compound 14a.

Synthesis of 6α-ethyl-3α, 7α-23-trihydroxy-24-nor-5β-cholan-23-sulfate from Compound 14a A solution of Compound 14a in dichloromethane is contacted with sulfur trioxide-pyridine complex at ambient temperature. The solution is concentrated and the residue is dissolved in methanol and contacted with a solution of NaOH in methanol at reflux. The solvent is evaporated and the resulting material is dissolved in a mixture of methanol and water, then passed through Dowex resin column. The effluent is evaporated to afford 6α-ethyl-3α, 7α-23-trihydroxy-24-nor-5β-cholan-23-sulfate.

Example 5. Synthesis of 6α-ethyl-23(S)-methyl-3α, 7α, 12α-trihydroxy-5β-cholan-24-oic Acid from Compound 7e Synthesis of Compound 10e from Compound 7e

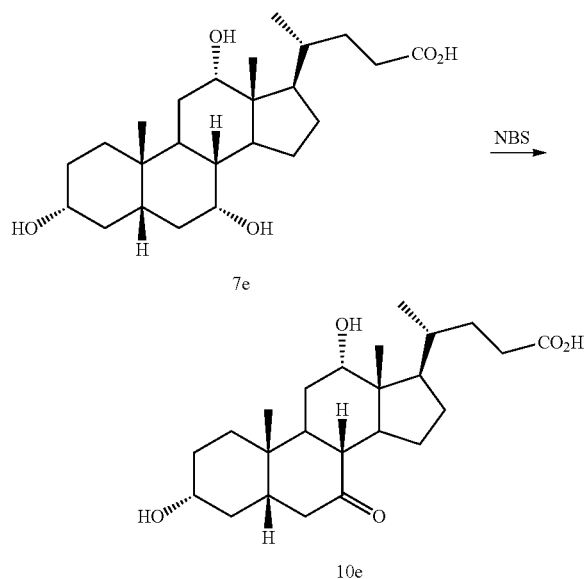

A solution of Compound 7e in ethyl acetate, acetic acid and methanol is contacted with an aqueous solution of NaBr and tetrabutylammonium bromide. To the well stirred solution is added an aqueous solution of sodium hypochlorite. The aqueous layer is removed and the organic layer is washed with aqueous sodium bisulfate solution. The organic layer is dried over $Na_2SO_4$ and evaporated to afford Compound 10e.

Synthesis of Compound 10f from Compound 10e

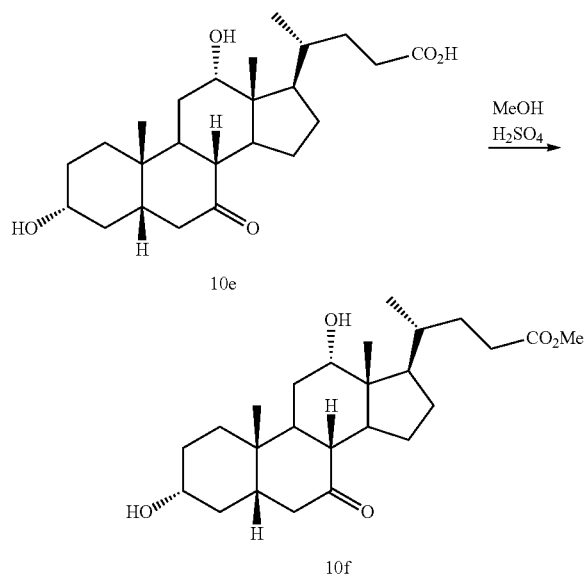

A solution of Compound 10e in methanol is contacted with conc. $H_2SO_4$ and heated to reflux. The solution is cooled and diluted with water to initiate crystallization. The solids are filtered and washed with a mixture of methanol and water to afford Compound 10f.

Synthesis of Compound 12c from Compound 10f

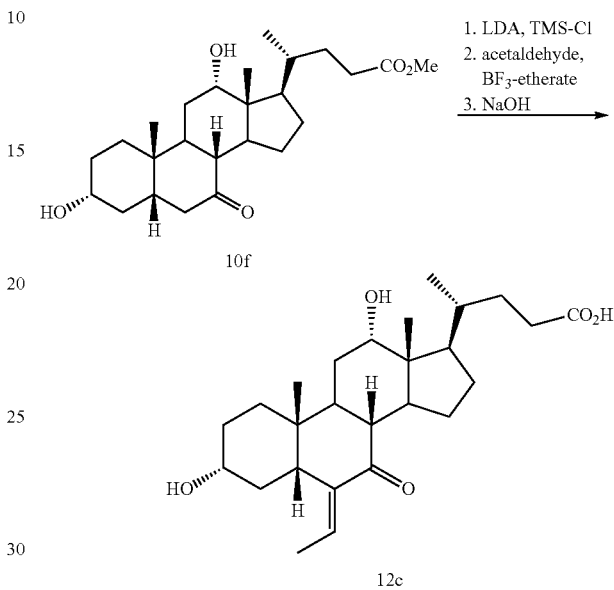

A solution of Compound 10f in dry THF in the presence of chlorotrimethylsilane is contacted with a solution of LDA at below −15° C. The mixture is quenched with aqueous citric acid solution and the organic layer is separated and concentrated to an oil. The oil is dissolved in dry dichloromethane and admixed with acetaldehyde, which is then added to a pre-cooled solution of $BF_3$-$OEt_2$ while maintaining an internal temperature of <−60° C. The mixture is warmed to ambient temperature and quenched with dilute aqueous NaOH solution. The organic layer is concentrated to an oil, diluted with methanol and contacted with an aqueous NaOH solution. The mixture is diluted with toluene and the aqueous layer is removed and acidified with citric acid in the presence of ethyl acetate. The organic layer is removed and partially evaporated to induce crystallization. The suspension is filtered and washed with ethyl acetate to afford Compound 12c.

Synthesis of Compound 13d from Compound 12c

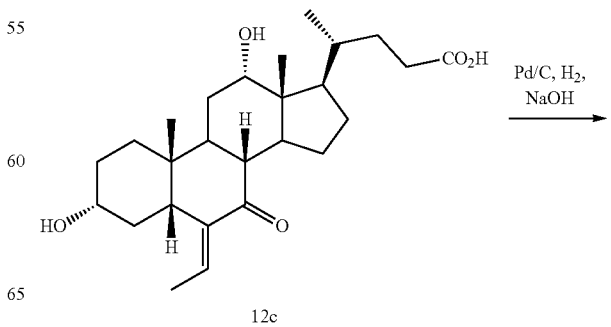

102

Synthesis of Compound 14b from Compound 15a

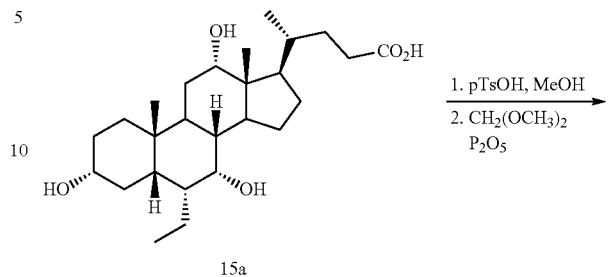

15a

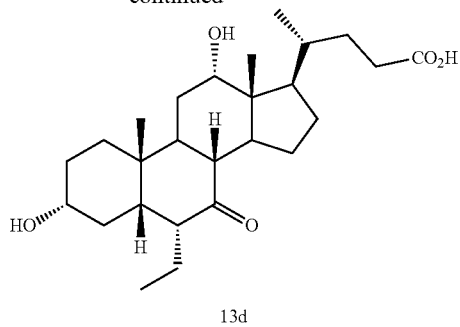

13d

A solution of Compound 12c in aqueous NaOH is contacted with palladium on carbon and pressurized with 2-5 bar hydrogen pressure. The mixture is vigorously stirred and heated to 95-100° C. until hydrogen uptake stops. The mixture is filtered through Celite and the aqueous layer is contacted with dilute aqueous HCl in the presence of n-butyl acetate. The organic layer is separated and partially evaporated to induce crystallization. The suspension is filtered and the solids are washed with n-butyl acetate to afford Compound 13d.

Synthesis of Compound 15a from Compound 13d

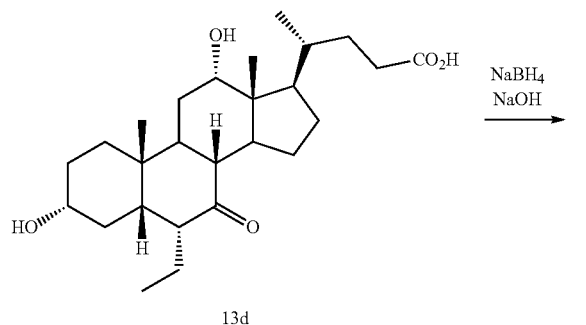

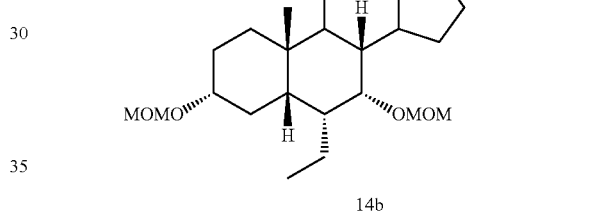

14b

A solution of Compound 15a in dry methanol is contacted with p-toluenesulfonic acid. The mixture is concentrated, diluted with ethyl acetate and washed with water. The organic layer is dried over $Na_2SO_4$ and concentrated. The concentrate is dissolved in chloroform and dimethoxymethane, then contacted with $P_2O_5$. The solvent is decanted from the solids and solids and washed with an aqueous $NaHCO_3$ solution. The organic layer is concentrated to afford Compound 14b.

Synthesis of Compound 16a (6α-ethyl-23(S)-methyl-3α, 7α, 12α-trihydroxy-5β-cholan-24-oic Acid and its Isomer) from Compound 14b

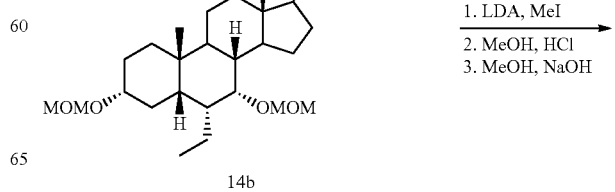

14b

A solution of Compound 13d in aqueous NaOH is heated to 90° C. and contacted with sodium borohydride. The mixture is cooled and quenched with an aqueous citric acid solution in the presence of n-butyl acetate. The organic layer is separated and partially evaporated to induce crystallization. The suspension is filtered and the solids are washed with n-butyl acetate to afford Compound 15a.

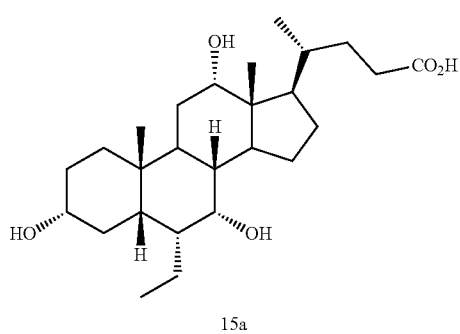

15a

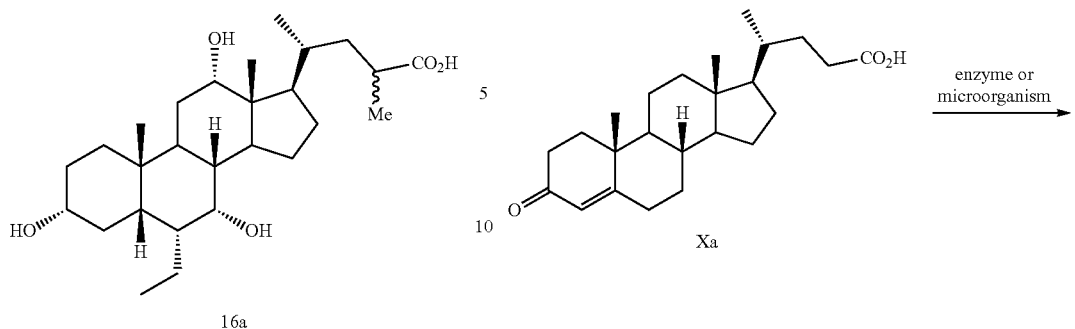

16a

A solution of Compound 16b in dry THF at −78° C. is contacted with a solution of LDA. The mixture is aged and contacted with iodomethane and gradually warmed to ambient temperature. The solvent is evaporated and the residue is dissolved with water in the presence of ethyl acetate. The organic layer is separated and concentrated to a residue. The residue is contacted with a solution of conc. HCl in methanol and warmed to 45° C., then concentrated under to a residue. The residue is dissolved with water in the presence of ethyl acetate, the organic layer is separated and concentrated to a residue. The residue is contacted with a 10% solution of NaOH in methanol. The mixture is concentrated to a residue and dissolved in a mixture of aqueous HCl and chloroform. The organic layer is separated and concentrated to afford Compound 16a.

Example 6: Synthesis of CDCA from β-sitosterol

Compound 1 is subjected to enzymatic or microbial oxidation conditions to provide C24 acid with concomitant oxidation at C3 and migration of the C5-C6 olefin to generate Compound Xa.

Compound Xa is further subjected to enzymatic or microbial oxidation conditions to affect hydroxylation at C7 to generate Compound Xb.

Compound Xb is subjected to olefin reduction conditions. Compound Xb is hydrogenated in the presence of a palladium catalyst (e.g., Pd/C), platinum catalyst (e.g., PtO₂), nickel catalyst (e.g., Raney nickel and Urushibara nickel), or copper catalyst (e.g., Cu/Al₂O₃) to generate Compound Xc.

Compound Xc is subjected to ketone reduction conditions, thus Compound Xc is contacted with a reducing agent (e.g., NaBH₄) to generate Compound 7.

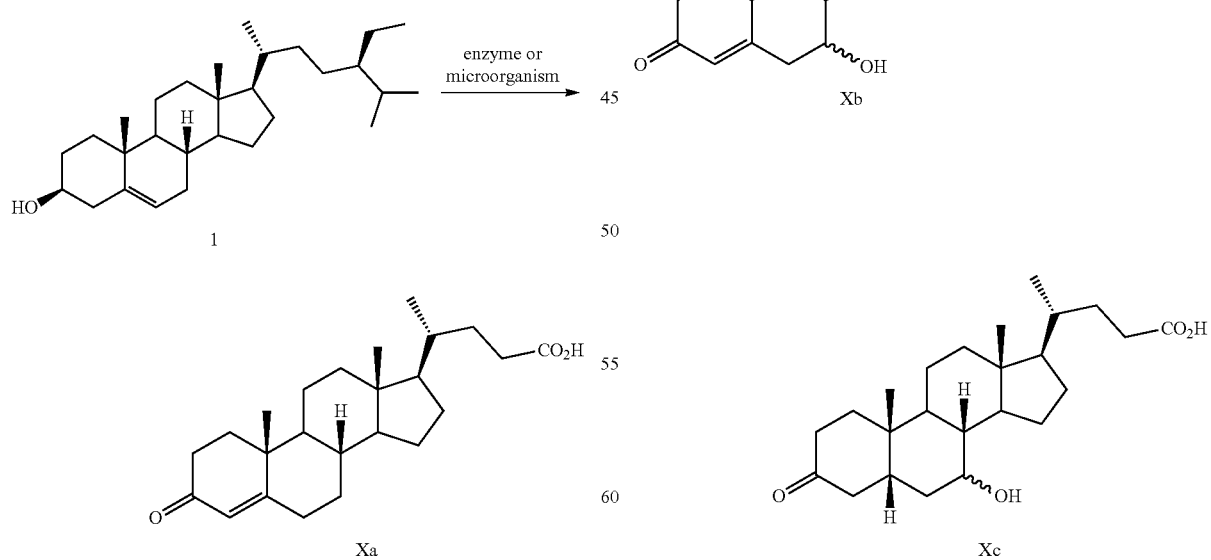

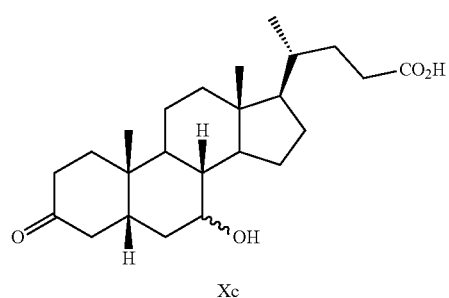

Xc

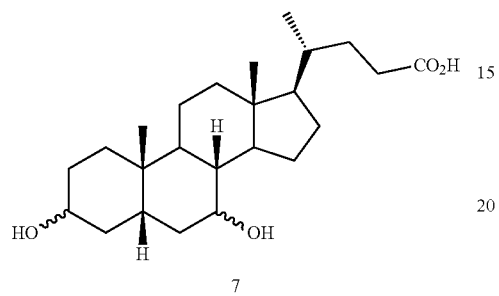

7

In an alternative scheme, protection at C3 and C7 are carried out prior to side chain degradation to the C24 acid and migration of the C5-C6 olefin.

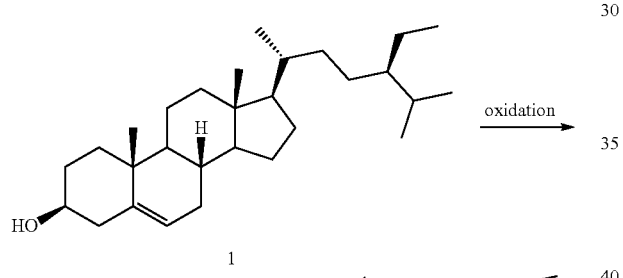

1

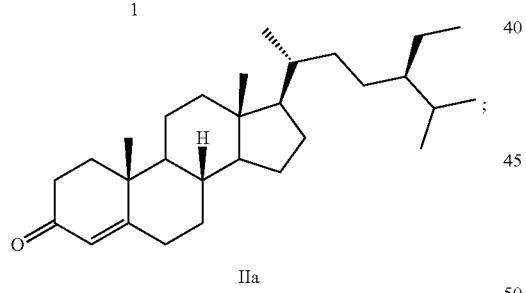

IIa

Compound 1 is oxidized at C3 to the corresponding ketone (Compound IIa). Thereafter, Compound IIa is further oxidized to Compound IIb

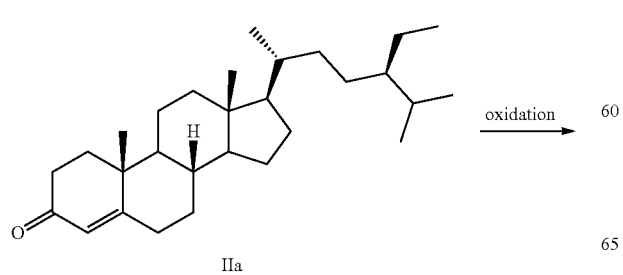

IIa

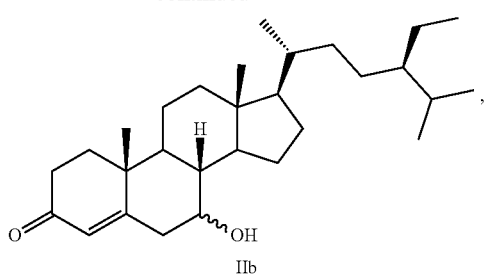

IIb

Compound IIb is then selectively reduced to Compound IIc:

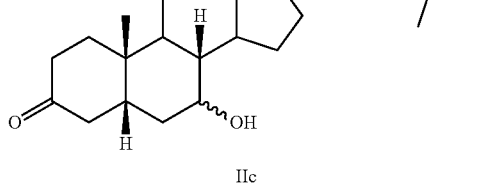

IIb

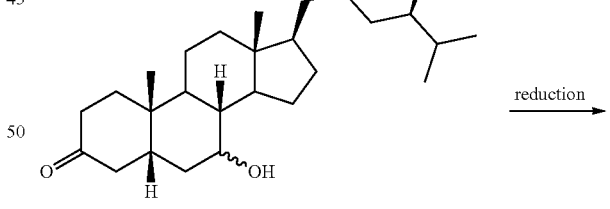

IIc and reducing Compound IIc to Compound 2a:

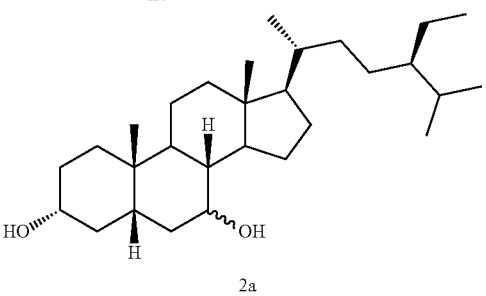

IIc

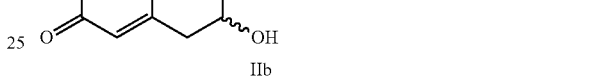

2a

The conversion of Compound 2 to Compound 5 was carried out via protection at C3 and C7. Various protecting groups are used, including acetyl.

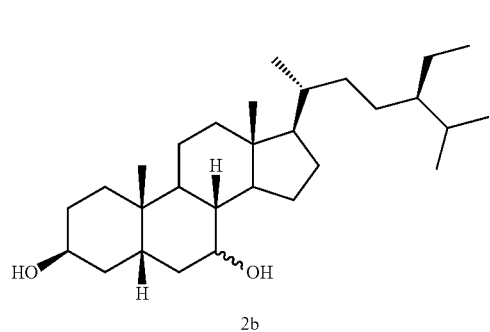

2b

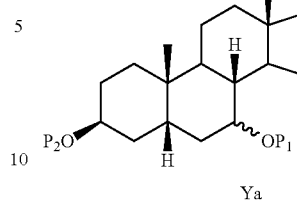

3b

Compound 3b is then subjected to enzymatic or microbial oxidation conditions to generate Compound Ya.

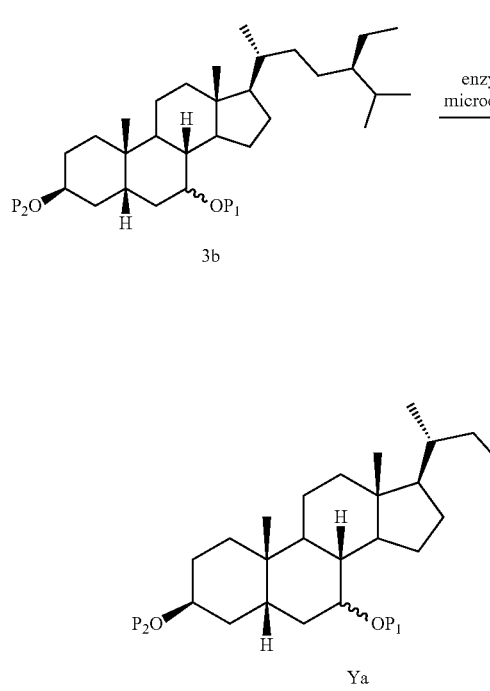

Compound Ya is subjected to deprotection conditions for removal of the $P_1$ and $P_2$ protecting groups to generate Compound 7b.

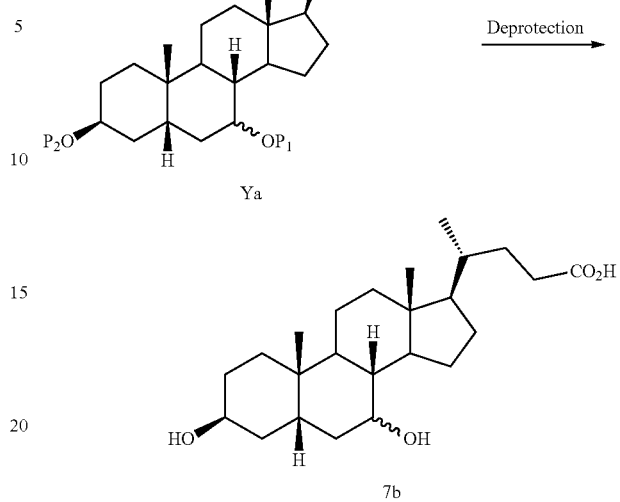

Compound 7b is subjected to oxidation conditions (e.g., NaOCl) to generate Compound 8.

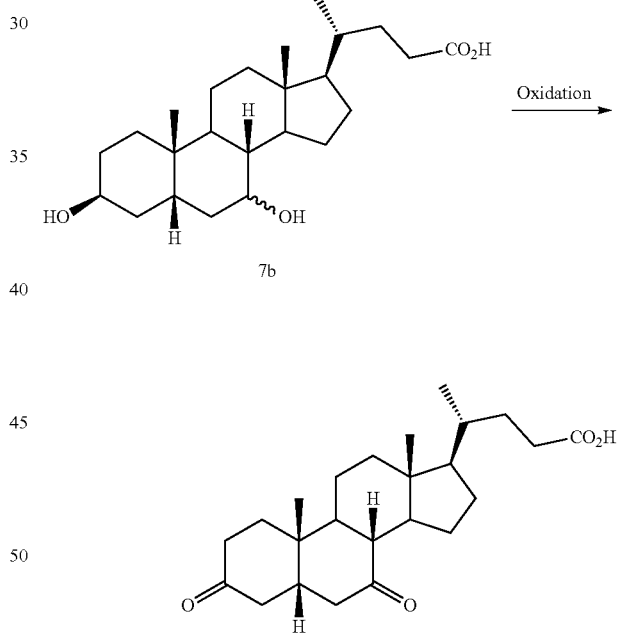

Compound 8 was subjected to ketone reduction conditions (e.g., $NaBH_4$) to generate Compound 9.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of preparing a compound of Formula (A):

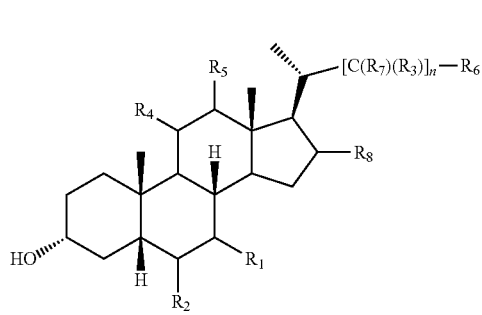

or a pharmaceutically acceptable salt, solvate, or amino acid conjugate thereof, wherein:

$R_1$ is α-OH or an oxo group;

$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;

$R_3$ and $R_7$ are each independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;

$R_4$, $R_5$ and $R_8$ are each independently H, α-OH, or β-OH;

$R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O; and n is 0, 1, 2 or 3;

comprising the steps of:

(1) converting Compound 1 to Compound 7

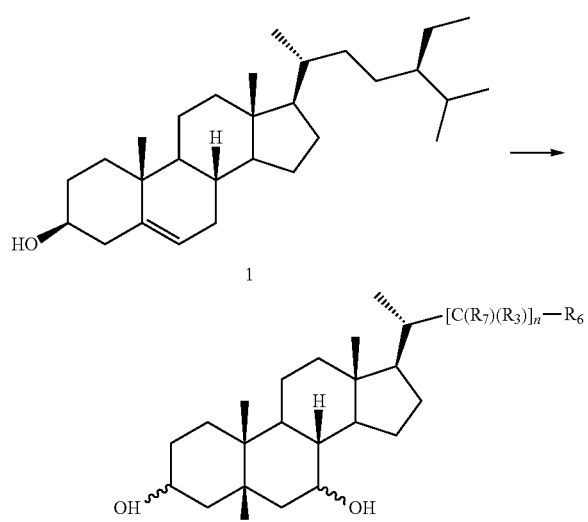

wherein "~~~" indicates that the OH at the C3-position or C7-position is in an α- or β-stereochemistry; and (2) converting Compound 7 to a compound of Formula (A),

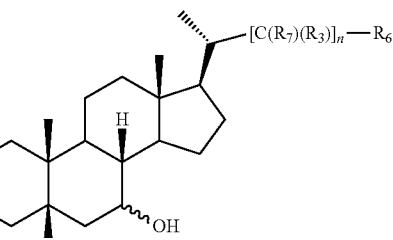

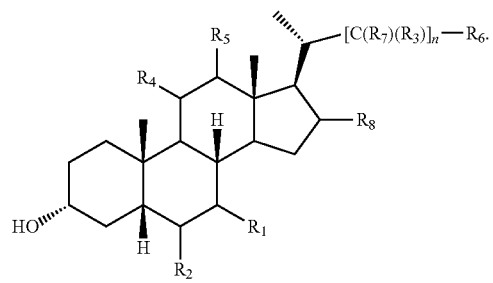

2. The method of claim 1, wherein the compound of Formula (A) is a compound of Formula (I):

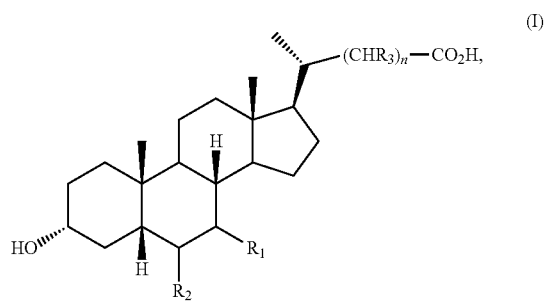

or a pharmaceutically acceptable salt, solvate, or amino acid conjugate thereof, wherein $R_3$ is H or $C_1$-$C_4$ alkyl.

3. The method of claim 1, wherein the compound of Formula (A) is a compound of Formula (Ia):

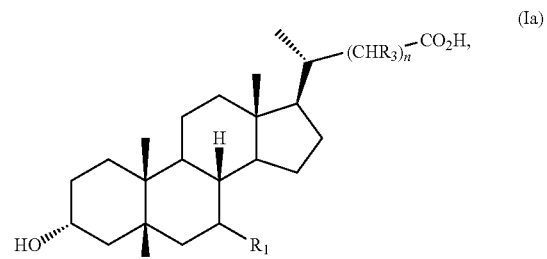

or a pharmaceutically acceptable salt, solvate, or amino acid conjugate thereof, wherein $R_3$ is H or $C_1$-$C_4$ alkyl.

4. The method of claim 1, wherein the compound of Formula (A) is a compound of Formula (Ib):

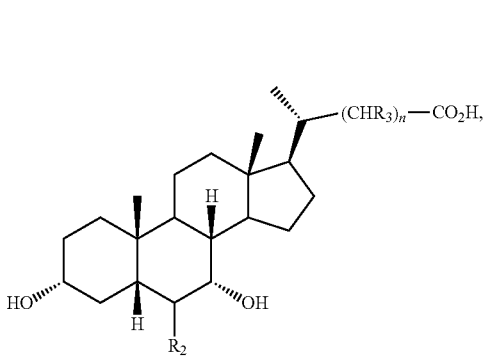

(Ib)

or a pharmaceutically acceptable salt, solvate, or amino acid conjugate thereof, wherein:
$R_2$ is α-$C_1$-$C_3$ alkyl; and
$R_3$ is H or $C_1$-$C_4$ alkyl.

5. The method of claim 1, wherein the compound of Formula (A) is a compound of Formula (II):

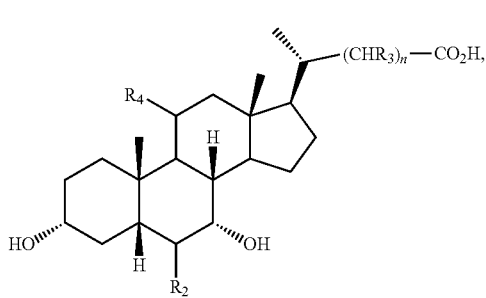

(II)

or a pharmaceutically acceptable salt, solvate, or amino acid conjugate thereof, wherein:
$R_2$ is α-$C_1$-$C_3$ alkyl;
$R_3$ is H or $C_1$-$C_4$ alkyl; and
$R_4$ is α-OH or β-OH.

6. The method of claim 1, wherein the compound of Formula (A) is a compound of Formula (III):

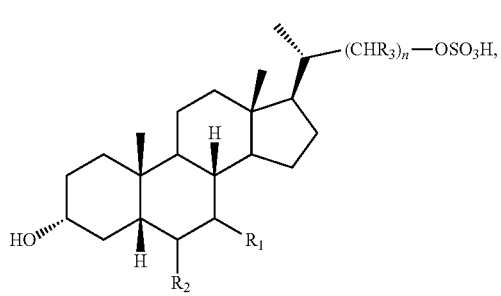

(III)

or a pharmaceutically acceptable salt or solvate thereof, wherein:
$R_1$ is α-OH or an oxo group;
$R_2$ is H, α-$C_1$-$C_3$ alkyl, cycloalkylmethylene or cycloalkyl; and
$R_3$ is H or $C_1$-$C_4$ alkyl.

7. The method of claim 1, wherein the compound of Formula (A) is a compound of Formula (IV):

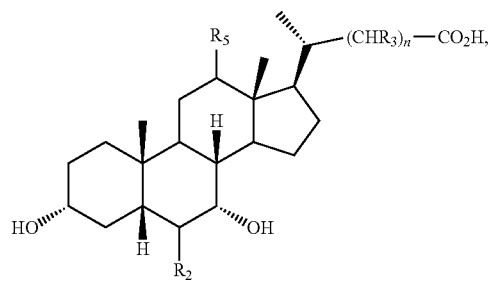

(IV)

or a pharmaceutically acceptable salt, solvate, or amino acid conjugate thereof, wherein:
$R_2$ is α-$C_1$-$C_3$ alkyl;
$R_3$ is H or $C_1$-$C_4$ alkyl; and
$R_5$ is α-OH or β-OH.

8. The method of claim 1, wherein the compound of Formula (A) is a compound of Formula (V):

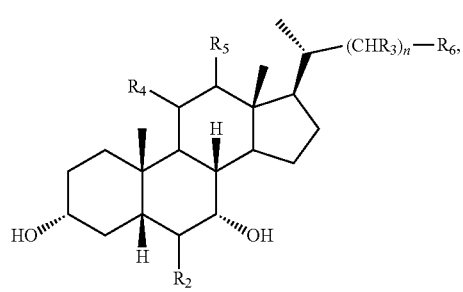

(V)

or a pharmaceutically acceptable salt, solvate, or amino acid conjugate thereof, wherein:
$R_2$ is H or α-$C_1$-$C_3$ alkyl;
$R_3$ is H or $C_1$-$C_4$ alkyl;
$R_4$ and $R_5$ are each independently H, α-OH or β-OH; and
$R_6$ is an optionally substituted 5-member heterocycle comprising 1-4 heteroatoms selected from N, S and O.

9. A method of preparing a compound of Formula (A):

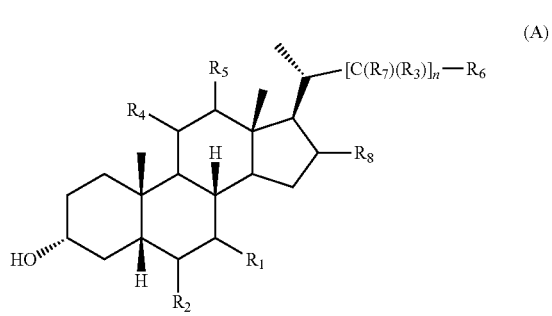

(A)

or a pharmaceutically acceptable salt, solvate, or amino acid conjugate thereof, wherein:
$R_1$ is α-OH or an oxo group;
$R_2$ is H, F, α-$C_1$-$C_3$ alkyl optionally substituted with F or OH, α-$C_1$-$C_3$ alkoxy, α-$C_2$-$C_3$ alkenyl or alkynyl, cycloalkylmethylene, or cycloalkyl;

$R_3$ and $R_7$ are each independently H, F, or $C_1$-$C_4$ alkyl optionally substituted with F or OH, or $R_3$ or $R_7$ taken together with another $R_3$ or $R_7$ on an adjacent carbon atom forms a substituted or unsubstituted $C_1$-$C_6$ carbocyclic or heterocyclic ring;

$R_4$, $R_5$ and $R_8$ are each independently H, α-OH, or β-OH;

$R_6$ is $CO_2H$, $OSO_3H$, $NH_2$, $NHCO_2(CH_2CHCH)$phenyl, $NHCO_2CH_2CH_3$, $C(O)NHOH$, $C(O)NH(CH_2)_2OH$, $CONH(CH_2)_2OSO_3H$, or an optionally substituted 5-member heterocycle comprising 1-4 heteroatoms selected from N, S and O; and n is 0, 1, 2 or 3;

comprising the steps of:

(1) converting Compound 1 to Compound 2

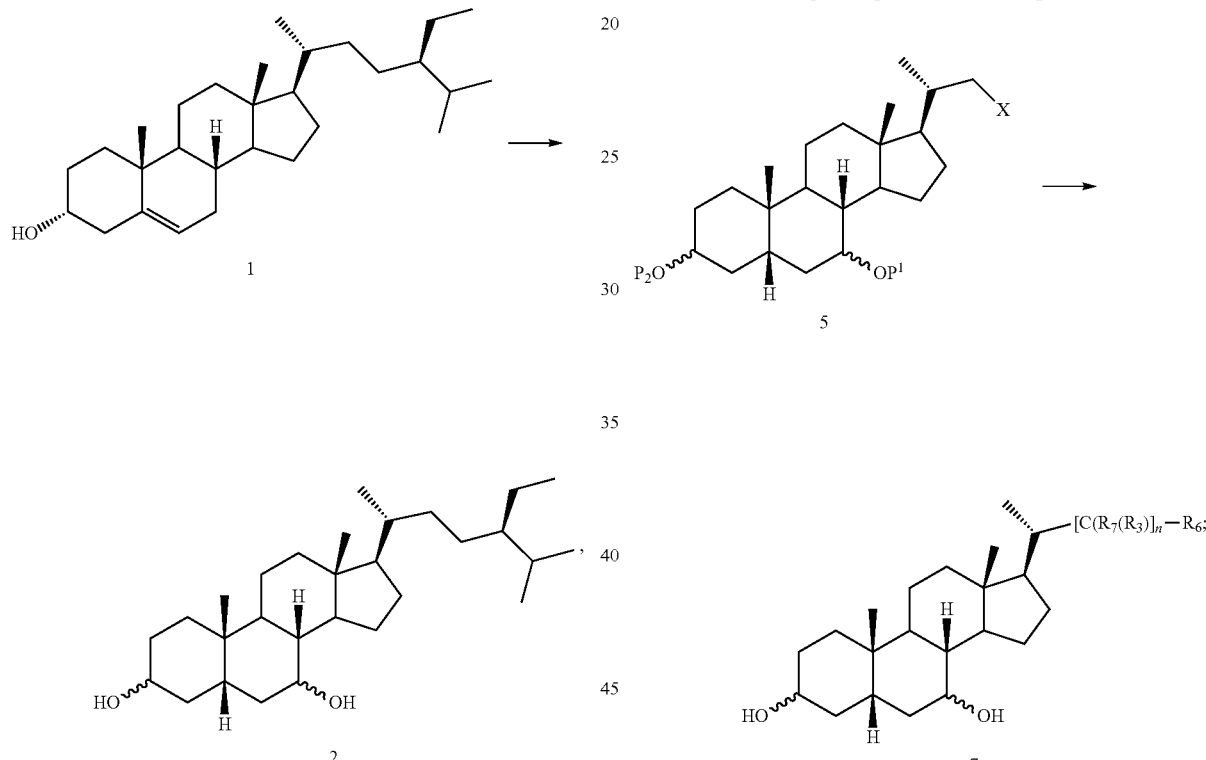

wherein "~~~" indicates that the OH at the C3-position or C7-position is in an α- or β-stereochemistry;

(2) converting Compound 2 to Compound 5

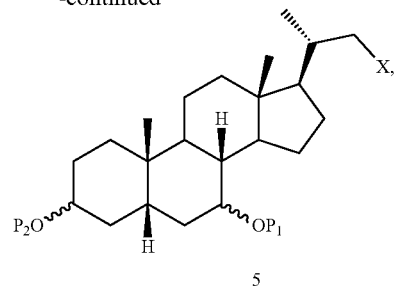

wherein:

X is a leaving group; and $P_1$ and $P_2$ are each independently a protecting group;

(3) converting Compound 5 to Compound 7

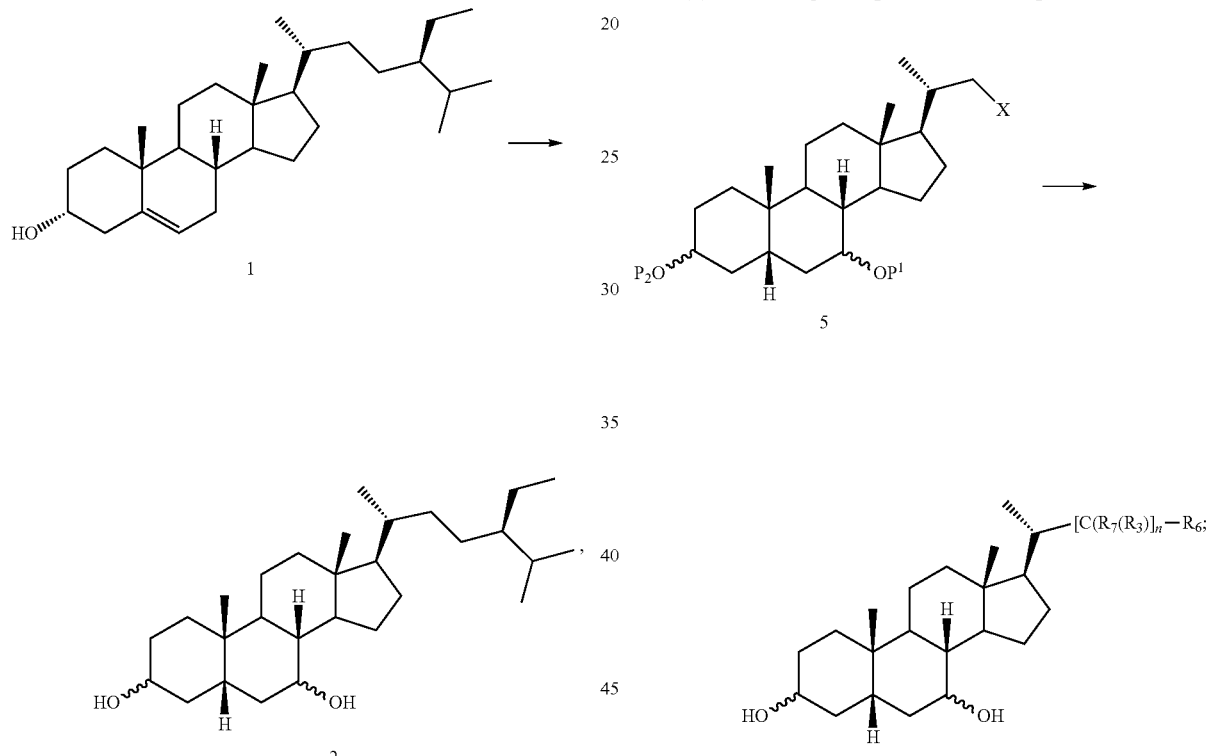

and (4) converting Compound 7 to a compound of Formula (A)

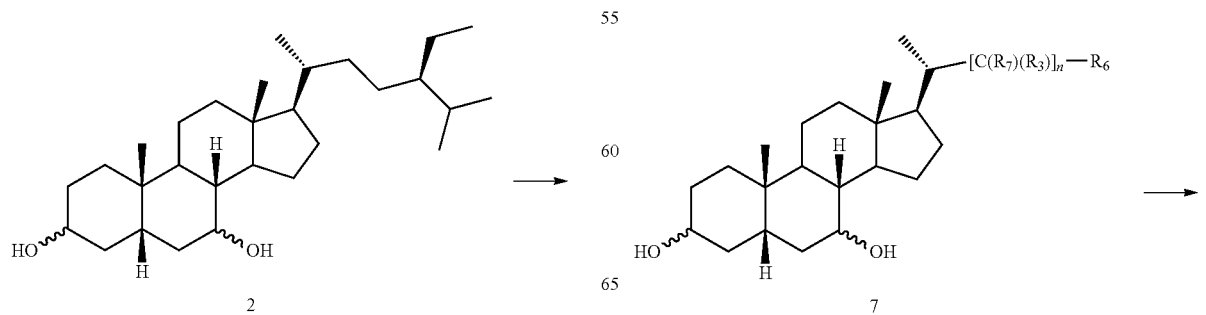

-continued

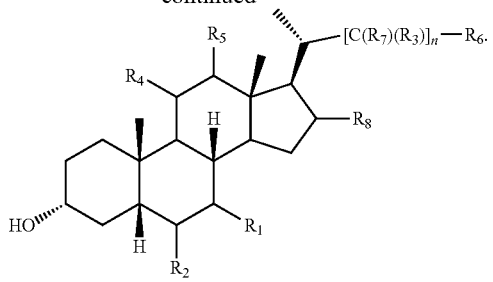

10. The method of claim 9, wherein the compound of Formula (A) is a compound Formula (I):

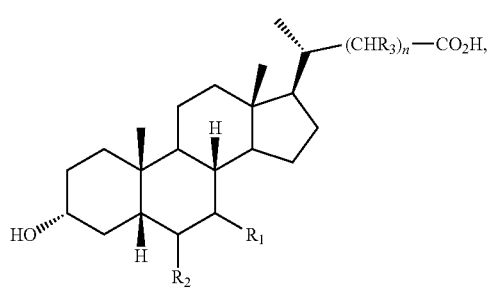

or a pharmaceutically acceptable salt, solvate, or amino acid conjugate thereof, wherein $R_3$ is H or $C_1$-$C_4$ alkyl.

11. The method of claim 9, wherein the compound of Formula (A) is a compound Formula (Ia):

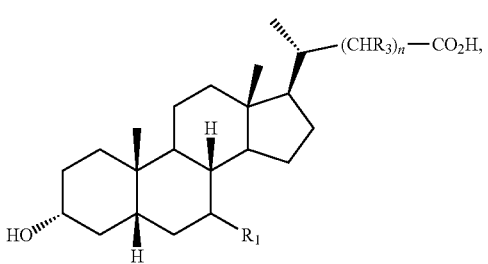

or a pharmaceutically acceptable salt, solvate, or amino acid conjugate thereof, wherein $R_3$ is H or $C_1$-$C_4$ alkyl.

12. The method of claim 9, wherein the compound of Formula (A) is a compound Formula (Ib):

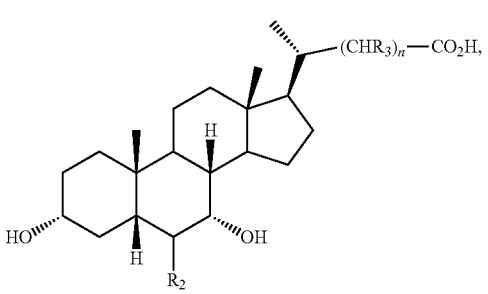

or a pharmaceutically acceptable salt, solvate, or amino acid conjugate thereof, wherein:
$R_2$ is α-$C_1$-$C_3$ alkyl; and
$R_3$ is H or $C_1$-$C_4$ alkyl.

13. The method of claim 9, wherein the compound of Formula (A) is a compound of Formula (II):

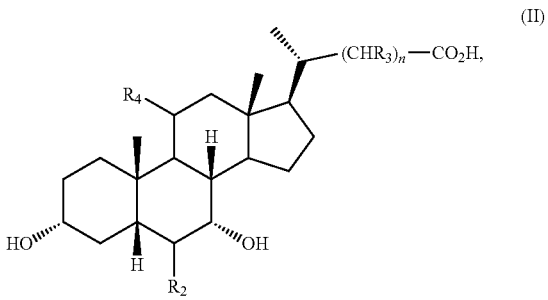

or a pharmaceutically acceptable salt, solvate, or amino acid conjugate thereof, wherein:
$R_2$ is α-$C_1$-$C_3$ alkyl;
$R_3$ is H or $C_1$-$C_4$ alkyl; and
$R_4$ is α-OH or β-OH.

14. The method of claim 9, wherein the compound of Formula (A) is a compound Formula (III):

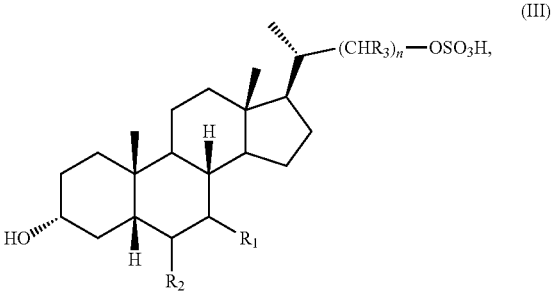

or a pharmaceutically acceptable salt or solvate thereof, wherein:
$R_1$ is α-OH or an oxo group;
$R_2$ is H, α-$C_1$-$C_3$ alkyl, cycloalkylmethylene, or cycloalkyl; and
$R_3$ is H or $C_1$-$C_4$ alkyl.

15. The method of claim 9, wherein the compound of Formula (A) is a compound of Formula (IV):

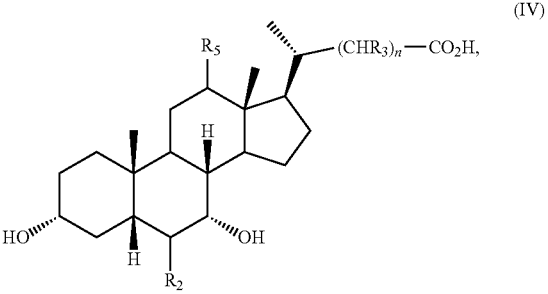

or a pharmaceutically acceptable salt, solvate, or amino acid conjugate thereof, wherein:

$R_2$ is $\alpha$-$C_1$-$C_3$ alkyl;

$R_3$ is H or $C_1$-$C_4$ alkyl; and $R_5$ is $\alpha$-OH or $\beta$-OH.

16. The method of claim 9, wherein the compound of Formula (A) is a compound of Formula (V):

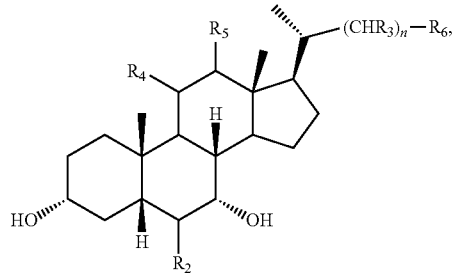

(V)

or a pharmaceutically acceptable salt, solvate, or amino acid conjugate thereof, wherein:

$R_2$ is H, or $\alpha$-$C_1$-$C_3$ alkyl;

$R_3$ is H or $C_1$-$C_4$ alkyl;

$R_4$ and $R_5$ are each independently H, $\alpha$-OH or $\beta$-OH; and $R_6$ is an optionally substituted 5-member heterocycle comprising 1-4 heteroatoms selected from N, S and O.

17. The method of claim 1, wherein $R_2$ is cycloalkylmethylene or cycloalkyl.

18. The method of claim 17, wherein $R_2$ is cyclopropylmethylene.

19. The method of claim 18, wherein the compound of Formula A is a compound

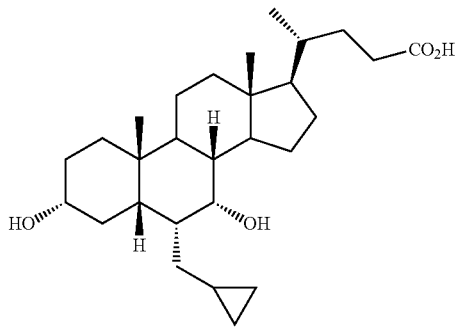

or a pharmaceutically acceptable salt, solvate, or amino acid conjugate thereof.

* * * * *